(12) United States Patent
Pirozhkova et al.

(10) Patent No.: US 10,954,515 B2
(45) Date of Patent: Mar. 23, 2021

(54) THERAPEUTIC METHODS, PRODUCTS AND COMPOSITIONS INHIBITING ZNF555

(71) Applicant: INSTITUT GUSTAVE ROUSSY, Villejuif (FR)

(72) Inventors: Iryna Pirozhkova, Arcueil (FR); Vasily Ogryzko, Fontenay-aux-Roses (FR)

(73) Assignee: INSTITUT GUSTAVE ROUSSY, Villejuif (FR)

( * ) Notice: Subject to any disclaimer, the term of this patent is extended or adjusted under 35 U.S.C. 154(b) by 0 days.

(21) Appl. No.: 15/568,009

(22) PCT Filed: Apr. 21, 2016

(86) PCT No.: PCT/EP2016/058828
§ 371 (c)(1),
(2) Date: Oct. 20, 2017

(87) PCT Pub. No.: WO2016/170022
PCT Pub. Date: Oct. 27, 2016

(65) Prior Publication Data
US 2018/0119143 A1 May 3, 2018

(30) Foreign Application Priority Data
Apr. 21, 2015 (EP) .................................. 15305599

(51) Int. Cl.
| | | |
|---|---|---|
| *C12N 15/113* | (2010.01) | |
| *A61K 31/7088* | (2006.01) | |
| *A61P 35/00* | (2006.01) | |
| *C07K 14/47* | (2006.01) | |
| *A61P 21/00* | (2006.01) | |
| *A61P 19/00* | (2006.01) | |
| *A61K 38/48* | (2006.01) | |
| *C07K 16/18* | (2006.01) | |
| *G01N 33/50* | (2006.01) | |

(52) U.S. Cl.
CPC ........ *C12N 15/113* (2013.01); *A61K 31/7088* (2013.01); *A61K 38/4886* (2013.01); *A61P 19/00* (2018.01); *A61P 21/00* (2018.01); *A61P 35/00* (2018.01); *C07K 14/4705* (2013.01); *C07K 16/18* (2013.01); *G01N 33/5061* (2013.01); *C12N 2310/11* (2013.01); *C12N 2310/14* (2013.01); *C12N 2310/531* (2013.01); *C12N 2330/50* (2013.01); *C12N 2740/16043* (2013.01)

(58) Field of Classification Search
None
See application file for complete search history.

(56) References Cited

U.S. PATENT DOCUMENTS

| | | | |
|---|---|---|---|
| 2009/0269774 A1 | 10/2009 | Rothenberg et al. | |
| 2012/0251523 A1* | 10/2012 | Unutmaz | G01N 33/56972 424/130.1 |
| 2013/0347136 A1* | 12/2013 | Emerson, Jr. | C12N 15/111 800/9 |

FOREIGN PATENT DOCUMENTS

WO    WO 2010/0048670    *    5/2010

OTHER PUBLICATIONS

Kempf et al. (2006, Cir. Res. 98:351-350).*
Feldman, 2002, Molecular Pharmacology. 61(4): 707-709.*
Janigro (2008, Epilepsy Currents 8(1): 23-24).*
Breit et al. (2012, Nephrol. Dial. Transplant. 27:70-75).*
Ho et al. (2013, Clin. Chem. 59:1613-1620).*
Abulizi et al. (2017, Sci. Rep. 7(1):1037; pp. 1-10).*
Zimmers et al. (2005, Shock 23(6):543-548).*
Mazagova et al. (2013, Am. J. Physiol. Renal Physiol. 305:F1249-F1264).*
Gura (Science, v278, 1997, pp. 1041-1042).*
Freshney (Culture of Animal Cells, A Manual of Basic Technique, Alan R. Liss, Inc., 1983, New York, p. 4).*
Dermer (Bio/Technology, 1994, 12:320).*
Zips et al. (2005, in Vivo 19:1-8).*
2013, Nature Biotechnology 31:85.*
Kronqvist et al., 2002, Am. J. Pathol. 161:1535-1540.*
Cabianca, D. S. et al. "A Long ncRNA Links Copy Number Variation to a Polycomb/Trithorax Epigenetic Switch in FSHD Muscular Dystrophy" *Cell*, May 11, 2012, pp. 819-831, vol. 149, No. 4.
Cox, H. C. et al. "A genome-wide analysis of 'Bounty' descendants implicates several novel variants in migraine susceptibility" *Neurogenetics*, Jun. 8, 2012, pp. 261-266, vol. 13, No. 3.

(Continued)

*Primary Examiner* — Elizabeth C. Kemmerer
(74) *Attorney, Agent, or Firm* — Saliwanchik, Lloyd & Eisenschenk

(57) ABSTRACT

The present invention relates to products and compositions as well as their therapeutic uses in human or veterinary medicine. In particular, the invention provides ZNF555 as a new therapeutic target for the prevention or treatment of a musculoskeletal disease in a subject. Particular embodiments include wherein the musculoskeletal disease is selected from Facioscapulohumeral Dystrophy (FSHD), a myopathy, musculoskeletal fibromatosis and muscular cachexia. Also disclosed is a method for identifying and selecting a compound inhibiting or decreasing the expression or activity of ZNF555, the method comprising a step of detecting and/or measuring the level of expression of ZNF555 or ANTI in a muscle cell in the presence of a test compound, wherein an absent or decreased expression of ZNF555 or ANTI in comparison with a control muscle cell that has not been exposed to or contacted with the test compound, is indicative of the capacity of said compound to inhibit or decrease the expression or activity of ZNF555 in said cell.

2 Claims, 23 Drawing Sheets
Specification includes a Sequence Listing.

(56) References Cited

OTHER PUBLICATIONS

Database EMBL [Online] Accession No. EU832270, "Synthetic construct *Homo sapiens* clone HAIB:100067299; DKFZo004H0826 zinc finger protein 555 protein (ZNF555) gene, encodes complete protein" Jun. 27, 2008, pp. 1-2, XP-002746827.
Kim, E. et al. "ZNF555 protein binds to transcriptional activator site of 4qA allele and ANT1: potential implication in Facioscapulohumeral dystrophy" *Nucleic Acids Research*, Jul. 15, 2015, pp. 8227-8242, vol. 43, No. 17.
Wiemann, S. et al. "Toward a Catalog of Human Genes and Proteins: Sequencing and Analysis of 500 Novel Complete Protein Coding Human cDNAs" *Genome Research*, Mar. 1, 2001, pp. 422-435, vol. 11, No. 3.
Written Opinion in International Application No. PCT/EP2016/058828, dated Jul. 5, 2016, pp. 1-10.
Galliano M.-F. et al. "Binding of ADAM12, a Marker of Skeletal Muscle Regeneration, to the Muscle-specific Actin-binding Protein, α-Actinin-2, is Required for Myoblast Fusion" *The Journal of Biological Chemistry*, May 5, 2000, pp. 13933-13939, vol. 275, No. 18.
Kronqvist, P. et al. "Short Communication: ADAM12 Alleviates the Skeletal Muscle Pathology in mdx Dystrophic Mice" *American Journal of Pathology*, Nov. 2002, pp. 1535-1540, vol. 161, No. 5.
Nakatani, Y. et al. "Immunoaffinity Purification of Mammalian Protein Complexes" *Methods in Enzymology*, 2003, pp. 430-444, vol. 370.

\* cited by examiner

Figure 6:
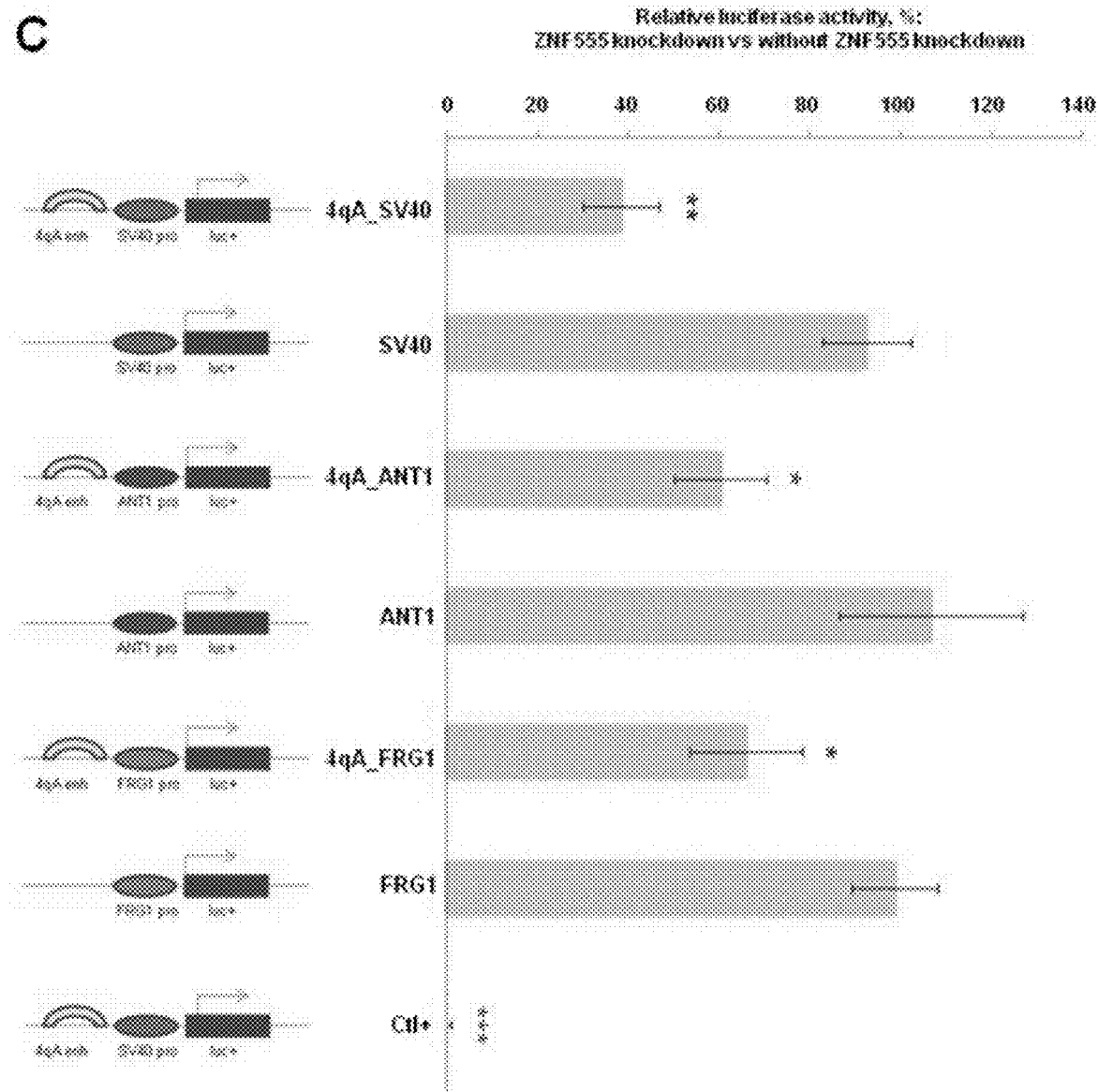

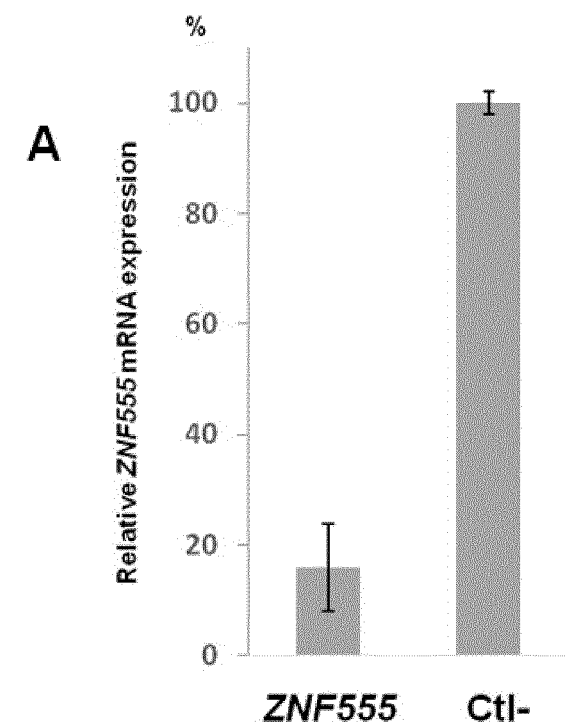
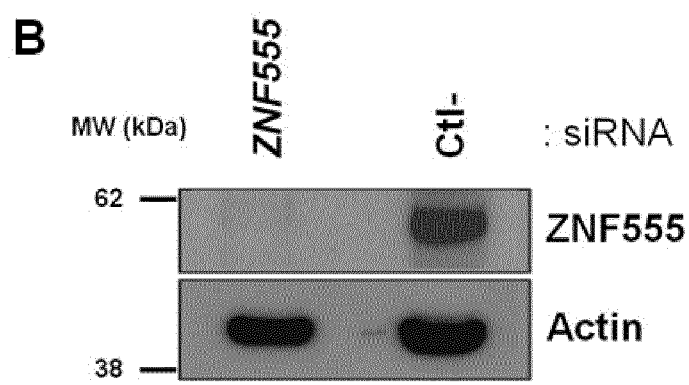
FIGURE 6

```
               Sau3AI (5' GATC)
                      ↓
Bsr1  :  catcacctgggtgatcattgcagagatacgtcacaataccccctgtaggtggggcctagacaagag--g   67
Bsr2  :  catcacttaggtgatcagtgcagatgtgtttcagaactccata-gtagactgaacctagagaatggtta   68
Bsr3  :  cataacttcggtgatcagtgcagagatatgtcacaatatccctgtagaaaaagcctgaaattgattta    69
Bsr4  :  catcacctag-tgatcagtgtagagatatgtta-aaattctcgtgtagacagagcctagacaattgtta   67
Bsr5  :  aatcacctcagagatcagtgcagagatatgtaccagtgtccctgtaggcagtgcctagacaagagttg    69
Bsr6  :  catcacctgtttgatcagtgcagagatatctcacaaagcccc-tataagccaaaccttgacaagggtta   68
Bsr7  :  cttcacctgggtgatcagtgcagtgatatgtcacaaaaatccctgtagacagagcctagacaagagtta   69
Bsr8  :  cctgcctgggctgatcagtgcagggataagtcataaagcctcctgtaggcagagtgtaggcaagtgttc   69
Bsr9  :  catcacctgggtgatcagtgcagagatatgtcacaaatcccctctaggcagagtatagagaagagtcc   69
Bsr10 :  catcacctggggatcagtgcagagatatgtca-aaacgctcctgtaggctgaacctagacaggagtta   68
Bsr11 :  catcacctgggtgatctgtgcagagctatgtca-aaacgccctgtaggcagagcctagatgagtgtta   68
Bsr12 :  catcacctgggtgatcagtgcagatatttgacacaatgccccc-atagacagagcctaggcaagacttc   68
Bsr13 :  catcacctgggtgatcagtgcagatatttgacacaatgccccc-atagacagagcctaggcaagacttc   68
Bsr14 :  catcacctgggtgatcagtgcagatatttgacacaatgccccc-atagacagagcctaggcaagacttc   68
```

FIGURE 10

A

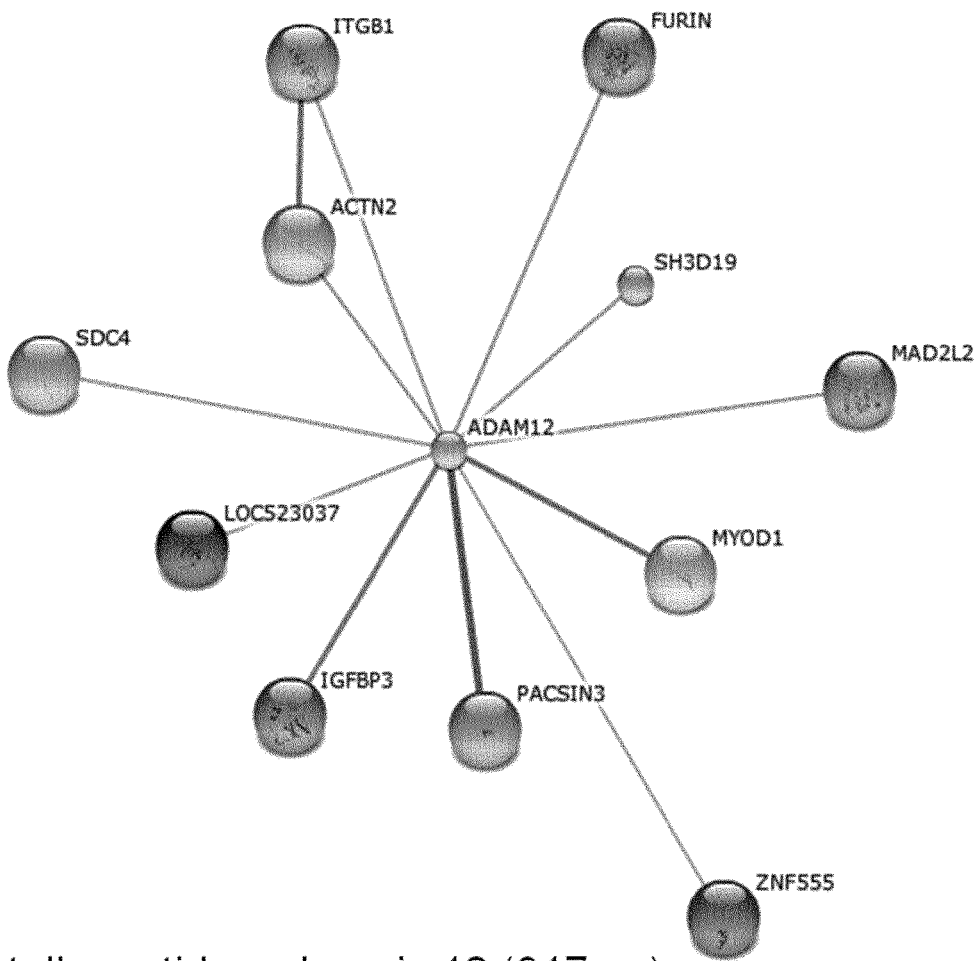

ADAM metallopeptidase domain 12 (917 aa)

- PACSIN3 - PREDICTED- Bos taurus misc_RNA (PACSIN3), miscRNA (426 aa)
- MYOD1 - Myoblast determination protein 1; Involved in muscle differentiation (myogenic factor) (318 aa)
- IGFBP3 - Insulin-like growth factor-binding protein 3 Precursor (IGF-binding protein 3)(IGFBP-3) (IBP-3) (291 aa)
- ACTN2 - Alpha-actinin-2 (Alpha-actinin skeletal muscle isoform 2)(F-actin cross-linking protein) (853 aa)
- FURIN - Furin Precursor (EC 3.4.21.75)(Paired basic amino acid residue-cleaving enzyme)(PACE) (797 aa)
- SH3D19 - SH3 domain containing 19 (784 aa)
- LOC5230 - SH3 multiple domains 1 (449 aa)
- MAD2L2 - MAD2 mitotic arrest deficient-like 2 (211 aa)
- ITGB1 - Integrin beta-1 Precursor (Fibronectin receptor subunit beta)(Integrin VLA-4 subunit beta) (801 aa)
- SDC4 - syndecan 4 (199 aa)

FIGURE 13

| Vector | Insertion Fragment | Size, bp | Chromosome Start/End, + Strand |
|---|---|---|---|
| p4qA | 4qA | 1464 | Pirozhkova I et al., PLoS One, 2008 |
| p4qA_1 | Fr1 | 564 | Un_gl000228 : 115554 / 116117 |
| p4qA_2 | Fr2 | 435 | Un_gl000228 : 115119 / 115553 |
| p4qA_3 | Fr3 | 468 | Un_gl000228 : 114650 / 115117 |
| p4qA_4 | Fr4=4qAe | 67 | Un_gl000228 : 116051 / 116117 |
| p4qA_5 | Fr5 | 203 | Un_gl000228 : 115915 / 116117 |
| p4qA_6 | Fr6 | 63 | Un_gl000228 : 115553 / 115615 |
| p4qA_7 | Fr7 | 106 | Un_gl000228 : 114650 / 114749 |
| pANT1 | ANT1 promoter | 715 | 4q : 186063741 / 186064455 |
| pFRG1 | FRG1 promoter | 588 | Petrov A et al., Genome Res, 2008 |
| p4qAe_ANT1 | 4qAe<br>ANT1 promoter | 67<br>715 | Un_gl000228 : 116051 / 116117<br>4q : 186063741 / 186064455 |
| p4qAe_FRG1 | 4qAe<br>FRG1 promoter | 67<br>577 | Un_gl000228 : 116051 / 116117<br>Petrov A et al., Genome Res, 2008 |

FIGURE 14

| Sequence ID | Forward | Reverse |
|---|---|---|
| *ANT1* promoter | ACCCAAGCATCGATATGG | TTGACTACTGCTGGAGTG |
| *FRG1* promoter | GCTTGATATTGTTGGTGAGT | GACAACCGACTTCTACAAT |
| *FRG2* promoter | GTTGTTGTTGAGCCCTGG | CCTAGAAGGTCACCGAA |
| *DUX4* | ACGGAGACTCGTTTGGA | TGGCCCTTCGATTCTGA |
| *DUX4c* | TGGCCCTTCGATTCTGA | GTGGAGGTGGTAGGTCTTT |
| *4qA* | TCCCCTGTAGGCAGAGA | CACTGATAACCAGGTGA |
| *ZNF555* | CCGCCTCCCCTAGGGTCC | TGAGCAGAATCCAGCAAAGCCCA |
| *ANT1* | GCCAGCAAACAGATCAGTGC | CCCCTCCAGAAGGAGGAA |
| *FRG1* | GGAAGTGGAACTCT | CCTGACAGCCTACGTCTCTG |
| *GAPDH* | ACCACAGTCCATGCCATCAC | CCAGTGAGCTTCCGTTCAG |

FIGURE 15

| MW | ID Swissprot | Entry Name |
|---|---|---|
| 70898 | P11142 | Heat shock cognate 71 kDa protein – Homo sapiens |
| 84660 | P07900 | Heat shock protein HSP 90-alpha – Homo sapiens |
| 121371 | A5A3E0 | ANKRD26-like family C member 1B – Homo sapiens |
| 42911 | P49903 | Selenide, water dikinase 1 – Homo sapiens |
| 38170 | O75436 | Vacuolar protein sorting-associated protein 26A – Homo sapiens |
| 73063 | Q8NEP9 | Zinc finger protein 555 – Homo sapiens |

FIGURE 16

| MW | ID Swissprot | Entry Name |
|---|---|---|
| 84660,2 | P07900 | Heat shock protein HSP 90- 75 –Homo sapiens |
| 70898,4 | P11142 | Heat shock cognate 71kDa protein – Homo sapiens |
| 51804,8 | Q02790 | FK506-binding protein 4 – Homo sapiens |
| 32575,2 | P06748 | Nucleophosmin – Homo sapiens |
| 36053,4 | P04406 | Glyceraldehyde-3-phosphate dehydrogenase – Homo sapiens |
| 121371,3 | A5A3E0 | ANKDRD26-like family C member 1B – Homo sapiens |
| 94300,5 | P34932 | Heat shock 70kDa protein 4 – Homo sapiens |
| 164940,4 | P31327 | Carbamoyl-phosphate synthase [ammonia], mitochondrial precursor – Homo sapiens |
| 27692,8 | P30048 | Thioredoxin-dependent peroxide reductase, mitochondrial precursor – Homo sapiens |
| 50151,9 | P68363 | Tubulin alpha-1B chain – Homo sapiens |
| 61055 | P10809 | 60 kDa heat shock protein, mitochondrial precursor – Homo sapiens |

FIGURE 17

SEQUENCE LISTING

<160> NUMBER OF SEQ ID NOS: 51

<210> SEQ ID NO 1
<211> LENGTH: 1884
<212> TYPE: DNA
<213> ORGANISM: Homo sapiens

<400> SEQUENCE: 1

```
atggactcag tggtctttga ggatgtggct gtggacttca ccctggagga gtgggctttg      60
ctggattctg ctcagaggga cctctacaga gatgtgatgc tggagacctt tcagaacctg     120
gcctcagtag atgatgaaac tcaatttaag gccagtgggt cagtttctca gcaggatatt     180
```

-continued

```
tatggagaga aaatacccaa ggaatctaaa atagccacgt tcaccagaaa tgtttcctgg      240
gcctctgttt taggaaaaat ttgggacagt cttagcatcg aagatcaaac cacaaaccag      300
gggagaaatc tcagtagaga tcatgggttg gagagactct gtgaaagtaa tgatcaatgt      360
ggagaagccc tcagccagat tccacatctt aatctgtaca agaaaattcc acctggagta      420
aaacagtatg aatacaacac gtacggaaaa gtcttcatgc atcgccgcac atccctcaag      480
agtcccatca cagttcacac tggacacaaa ccatatcagt gccaggaatg tgggcaggcc      540
tacagttgtc gttcacacct aagaatgcat gtgagaacca caatggaga gagaccctat       600 gtgtgtaaat tatgtgggaa aacctttcct cgtacttcct ccctcaatcg gcatgtaagg      660
attcacactg ctgagaaaac ctacgaatgt aagcaatgtg ggaaagcctt tattgacttc      720
tcaagtctta ctagtcatct cagaagtcac accggagaga agccatataa gtgtaaggaa      780
tgtgggaaag ctttcagtta ttcctcaacg tttcgaagac acacaataac acacactggc      840
gagaagccat ataaatgtaa ggaatgtgcg gaagccttta gttattcctc aacttttcga      900
agacatatga tttcacacac tggagagaag ccacataaat gtaaagaatg tggggaggcc      960
ttcagttatt cttcggcttt tcgaagacac atgataacac acactggaga gaaaccctac     1020
gaatgcaaac aatgtgggaa aaccttcatt tatctccagt cctttcgaag acatgaaagg     1080
attcacactg gagagaaacc ctacgaatgc aaacagtgtg ggaagacctt catttatccc     1140
cagtcctttc gaagacatga aaggactcat ggtggagaga aaccctatga atgcaaccag     1200
tgcgggaaag cattcagtca cccctcctcc tttcgaggac acatgagggt gcacactgga     1260
gagaaaccct atgagtgcaa gcaatgtggg aaaactttca attggcccat atctttacga     1320
aaacatatga gaacacatac tagagagaaa ccctatgaat gtaagcagtg tgggaaagcc     1380
ttcagcttgt ctgcttgctt tcgagaacat gtgagaatgc accctgaaga caaatccctat     1440 gaatgcaagc tatgtgggaa agctttctat tgccacatat ccttacaaaa acatatgaga     1500
agacataccg cagagaaact ctataaatgc aagcagtgtg gacagctttt cagttggcct      1560 gaactttgc aacaacatgt gagaacgcac actgtagaga agcccatga atgtaaggaa       1620 tgtgggaagg tcttcaaatg gccatcatct ttaccaatac atatgagact gcacactgga     1680 gagaacctt atcaatgtaa gcattgtggg aaagcattca attgttcctc atccttaagg      1740
cgacatgtga aatacacac tacagaaaaa cagtataagt gtaatgtagg acatcctcct       1800
gcaaatgaat tcatgtgcag tgcttcagaa aagtcacacc aggagagaga tctgatcaaa     1860
gttgtaaata tggtgttgcc ttta                                            1884
```

```
<210> SEQ ID NO 2
<211> LENGTH: 628
<212> TYPE: PRT
<213> ORGANISM: Homo sapiens
<220> FEATURE:
<221> NAME/KEY: DOMAIN
<222> LOCATION: (4)..(77)
<223> OTHER INFORMATION: Krab DOMAIN
<220> FEATURE:
<221> NAME/KEY: ZN_FING
<222> LOCATION: (172)..(194)
<223> OTHER INFORMATION: Zinc finger
<220> FEATURE:
<221> NAME/KEY: ZN_FING
<222> LOCATION: (200)..(222)
<223> OTHER INFORMATION: Zinc finger
<220> FEATURE:
<221> NAME/KEY: ZN_FING
<222> LOCATION: (228)..(250)
<223> OTHER INFORMATION: Zinc finger
```

```
<220> FEATURE:
<221> NAME/KEY: ZN_FING
<222> LOCATION: (256)..(278)
<223> OTHER INFORMATION: Zinc finger
<220> FEATURE:
<221> NAME/KEY: ZN_FING
<222> LOCATION: (284)..(306)
<223> OTHER INFORMATION: Zinc finger
<220> FEATURE:
<221> NAME/KEY: ZN_FING
<222> LOCATION: (312)..(334)
<223> OTHER INFORMATION: Zinc finger
<220> FEATURE:
<221> NAME/KEY: ZN_FING
<222> LOCATION: (340)..(362)
<223> OTHER INFORMATION: Zinc finger
<220> FEATURE:
<221> NAME/KEY: ZN_FING
<222> LOCATION: (368)..(390)
<223> OTHER INFORMATION: Zinc finger
<220> FEATURE:
<221> NAME/KEY: ZN_FING
<222> LOCATION: (396)..(418)
<223> OTHER INFORMATION: Zinc finger
<220> FEATURE:
<221> NAME/KEY: ZN_FING
<222> LOCATION: (424)..(446)
<223> OTHER INFORMATION: Zinc finger
<220> FEATURE:
<221> NAME/KEY: ZN_FING
<222> LOCATION: (452)..(474)
<223> OTHER INFORMATION: Zinc finger
<220> FEATURE:
<221> NAME/KEY: ZN_FING
<222> LOCATION: (480)..(502)
<223> OTHER INFORMATION: Zinc finger
<220> FEATURE:
<221> NAME/KEY: ZN_FING
<222> LOCATION: (508)..(530)
<223> OTHER INFORMATION: Zinc finger
<220> FEATURE:
<221> NAME/KEY: ZN_FING
<222> LOCATION: (536)..(558)
<223> OTHER INFORMATION: Zinc finger
<220> FEATURE:
<221> NAME/KEY: ZN_FING
<222> LOCATION: (564)..(586)
<223> OTHER INFORMATION: Zinc finger

<400> SEQUENCE: 2

Met Asp Ser Val Val Phe Glu Asp Val Ala Val Asp Phe Thr Leu Glu
1               5                   10                  15

Glu Trp Ala Leu Leu Asp Ser Ala Gln Arg Asp Leu Tyr Arg Asp Val
                20                  25                  30

Met Leu Glu Thr Phe Gln Asn Leu Ala Ser Val Asp Asp Glu Thr Gln
            35                  40                  45

Phe Lys Ala Ser Gly Ser Val Ser Gln Gln Asp Ile Tyr Gly Glu Lys
        50                  55                  60

Ile Pro Lys Glu Ser Lys Ile Ala Thr Phe Thr Arg Asn Val Ser Trp
65                  70                  75                  80

Ala Ser Val Leu Gly Lys Ile Trp Asp Ser Leu Ser Ile Glu Asp Gln
                85                  90                  95

Thr Thr Asn Gln Gly Arg Asn Leu Ser Arg Asn His Gly Leu Glu Arg
            100                 105                 110

Leu Cys Glu Ser Asn Asp Gln Cys Gly Glu Ala Leu Ser Gln Ile Pro
        115                 120                 125

His Leu Asn Leu Tyr Lys Lys Ile Pro Pro Gly Val Lys Gln Tyr Glu
    130                 135                 140
```

-continued

```
Tyr Asn Thr Tyr Gly Lys Val Phe Met His Arg Thr Ser Leu Lys
145                 150                 155                 160

Ser Pro Ile Thr Val His Thr Gly His Lys Pro Tyr Gln Cys Gln Glu
            165                 170                 175

Cys Gly Gln Ala Tyr Ser Cys Arg Ser His Leu Arg Met His Val Arg
                180                 185                 190

Thr His Asn Gly Glu Arg Pro Tyr Val Cys Lys Leu Cys Gly Lys Thr
        195                 200                 205

Phe Pro Arg Thr Ser Ser Leu Asn Arg His Val Arg Ile His Thr Ala
    210                 215                 220

Glu Lys Thr Tyr Glu Cys Lys Gln Cys Gly Lys Ala Phe Ile Asp Phe
225                 230                 235                 240

Ser Ser Leu Thr Ser His Leu Arg Ser His Thr Gly Glu Lys Pro Tyr
            245                 250                 255

Lys Cys Lys Glu Cys Gly Lys Ala Phe Ser Tyr Ser Ser Thr Phe Arg
                260                 265                 270

Arg His Thr Ile Thr His Thr Gly Glu Lys Pro Tyr Lys Cys Lys Glu
        275                 280                 285

Cys Ala Glu Ala Phe Ser Tyr Ser Ser Thr Phe Arg Arg His Met Ile
    290                 295                 300

Ser His Thr Gly Glu Lys Pro His Lys Cys Lys Glu Cys Gly Glu Ala
305                 310                 315                 320

Phe Ser Tyr Ser Ser Ala Phe Arg Arg His Met Ile Thr His Thr Gly
            325                 330                 335

Glu Lys Pro Tyr Glu Cys Lys Gln Cys Gly Lys Thr Phe Ile Tyr Leu
                340                 345                 350

Gln Ser Phe Arg Arg His Glu Arg Ile His Thr Gly Glu Lys Pro Tyr
        355                 360                 365

Glu Cys Lys Gln Cys Gly Lys Thr Phe Ile Tyr Pro Gln Ser Phe Arg
    370                 375                 380

Arg His Glu Arg Thr His Gly Gly Glu Lys Pro Tyr Glu Cys Asn Gln
385                 390                 395                 400

Cys Gly Lys Ala Phe Ser His Pro Ser Ser Phe Arg Gly His Met Arg
            405                 410                 415

Val His Thr Gly Glu Lys Pro Tyr Glu Cys Lys Gln Cys Gly Lys Thr
                420                 425                 430

Phe Asn Trp Pro Ile Ser Leu Arg Lys His Met Arg Thr His Thr Arg
        435                 440                 445

Glu Lys Pro Tyr Glu Cys Lys Gln Cys Gly Lys Ala Phe Ser Leu Ser
    450                 455                 460

Ala Cys Phe Arg Glu His Val Arg Met His Pro Glu Asp Lys Ser Tyr
465                 470                 475                 480

Glu Cys Lys Leu Cys Gly Lys Ala Phe Tyr Cys His Ile Ser Leu Gln
            485                 490                 495

Lys His Met Arg Arg His Thr Ala Glu Lys Leu Tyr Lys Cys Lys Gln
                500                 505                 510

Cys Gly Lys Ala Phe Ser Trp Pro Glu Leu Leu Gln Gln His Val Arg
        515                 520                 525

Thr His Thr Val Glu Lys Pro Tyr Glu Cys Lys Glu Cys Gly Lys Val
    530                 535                 540

Phe Lys Trp Pro Ser Ser Leu Pro Ile His Met Arg Leu His Thr Gly
545                 550                 555                 560
```

-continued

Glu Lys Pro Tyr Gln Cys Lys His Cys Gly Lys Ala Phe Asn Cys Ser
                565                 570                 575

Ser Ser Leu Arg Arg His Val Arg Ile His Thr Thr Glu Lys Gln Tyr
            580                 585                 590

Lys Cys Asn Val Gly His Pro Pro Ala Asn Glu Phe Met Cys Ser Ala
        595                 600                 605

Ser Glu Lys Ser His Gln Glu Arg Asp Leu Ile Lys Val Val Asn Met
    610                 615                 620

Val Leu Pro Leu
625

<210> SEQ ID NO 3
<211> LENGTH: 543
<212> TYPE: PRT
<213> ORGANISM: Homo sapiens
<220> FEATURE:
<221> NAME/KEY: DOMAIN
<222> LOCATION: (4)..(77)
<223> OTHER INFORMATION: Krab DOMAIN
<220> FEATURE:
<221> NAME/KEY: ZN_FING
<222> LOCATION: (185)..(208)
<223> OTHER INFORMATION: Zinc finger
<220> FEATURE:
<221> NAME/KEY: ZN_FING
<222> LOCATION: (213)..(236)
<223> OTHER INFORMATION: Zinc finger
<220> FEATURE:
<221> NAME/KEY: ZN_FING
<222> LOCATION: (241)..(266)
<223> OTHER INFORMATION: Zinc finger
<220> FEATURE:
<221> NAME/KEY: ZN_FING
<222> LOCATION: (270)..(294)
<223> OTHER INFORMATION: Zinc finger
<220> FEATURE:
<221> NAME/KEY: ZN_FING
<222> LOCATION: (298)..(322)
<223> OTHER INFORMATION: Zinc finger
<220> FEATURE:
<221> NAME/KEY: ZN_FING
<222> LOCATION: (325)..(350)
<223> OTHER INFORMATION: Zinc finger
<220> FEATURE:
<221> NAME/KEY: ZN_FING
<222> LOCATION: (353)..(378)
<223> OTHER INFORMATION: Zinc finger
<220> FEATURE:
<221> NAME/KEY: ZN_FING
<222> LOCATION: (381)..(406)
<223> OTHER INFORMATION: Zinc finger
<220> FEATURE:
<221> NAME/KEY: ZN_FING
<222> LOCATION: (409)..(433)
<223> OTHER INFORMATION: Zinc finger
<220> FEATURE:
<221> NAME/KEY: ZN_FING
<222> LOCATION: (437)..(461)
<223> OTHER INFORMATION: Zinc finger
<220> FEATURE:
<221> NAME/KEY: ZN_FING
<222> LOCATION: (469)..(490)
<223> OTHER INFORMATION: Zinc finger

<400> SEQUENCE: 3

Met Asp Ser Val Val Phe Glu Asp Val Ala Val Asp Phe Thr Leu Glu
1               5                   10                  15

Glu Trp Ala Leu Leu Asp Ser Ala Gln Arg Asp Leu Tyr Arg Asp Val
            20                  25                  30

Met Leu Glu Thr Phe Gln Asn Leu Ala Ser Val Asp Asp Glu Thr Gln
        35                  40                  45

-continued

```
Phe Lys Ala Ser Gly Ser Val Ser Gln Gln Asp Ile Tyr Gly Glu Lys
     50                  55                  60
Ile Pro Lys Glu Ser Lys Ile Ala Thr Phe Thr Arg Asn Val Ser Trp
 65                  70                  75                  80
Ala Ser Val Leu Gly Lys Ile Trp Asp Ser Leu Ser Ile Glu Asp Gln
                 85                  90                  95
Thr Thr Asn Gln Gly Arg Asn Leu Arg Asn His Gly Leu Glu Arg Leu
            100                 105                 110
Cys Glu Ser Asn Asp Gln Cys Gly Glu Ala Leu Ser Gln Ile Pro His
        115                 120                 125
Leu Asn Leu Tyr Lys Lys Ile Pro Pro Gly Val Lys Gln Tyr Glu Tyr
130                 135                 140
Asn Thr Tyr Gly Lys Val Phe Met His Arg Arg Thr Ser Leu Lys Ser
145                 150                 155                 160
Pro Ile Thr Val His Thr Gly His Lys Pro Tyr Gln Cys Gln Glu Cys
                165                 170                 175
Gly Gln Ala Tyr Ser Cys Arg Ser His Leu Arg Met His Val Arg Thr
            180                 185                 190
His Asn Gly Glu Arg Pro Tyr Val Cys Lys Leu Cys Gly Lys Thr Phe
        195                 200                 205
Pro Arg Thr Ser Ser Leu Asn Arg His Val Arg Ile His Thr Ala Glu
210                 215                 220
Lys Thr Tyr Glu Cys Lys Gln Cys Gly Lys Ala Phe Ile Asp Phe Ser
225                 230                 235                 240
Ser Leu Thr Ser His Leu Arg Ser His Thr Gly Glu Lys Pro Tyr Lys
                245                 250                 255
Cys Lys Glu Cys Gly Lys Ala Phe Ser Tyr Ser Ser Thr Phe Arg Arg
            260                 265                 270
His Thr Ile Thr His Thr Gly Glu Lys Pro Tyr Lys Cys Lys Glu Cys
        275                 280                 285
Ala Glu Ala Phe Ser Tyr Ser Ser Thr Phe Arg Arg His Met Ile Ser
290                 295                 300
His Thr Gly Glu Lys Pro His Lys Cys Lys Glu Cys Gly Glu Ala Phe
305                 310                 315                 320
Ser Tyr Ser Ser Ala Phe Arg Arg His Met Ile Thr His Thr Gly Glu
                325                 330                 335
Lys Pro Tyr Glu Cys Lys Gln Cys Gly Lys Thr Phe Ile Tyr Leu Gln
            340                 345                 350
Ser Phe Arg Arg His Glu Arg Ile His Thr Gly Glu Lys Pro Tyr Glu
        355                 360                 365
Cys Lys Gln Cys Gly Lys Thr Phe Ile Tyr Pro Gln Ser Phe Arg Arg
370                 375                 380
His Glu Arg Thr His Gly Gly Glu Lys Pro Tyr Glu Cys Asn Gln Cys
385                 390                 395                 400
Gly Lys Ala Phe Ser His Pro Ser Ser Phe Arg Gly His Met Arg Val
                405                 410                 415
His Thr Gly Glu Lys Pro Tyr Cys Lys Gln Cys Gly Lys Thr Phe
            420                 425                 430
Asn Trp Pro Ile Ser Leu Arg Lys His Met Arg Thr His Thr Arg Glu
        435                 440                 445
Lys Leu Tyr Lys Cys Lys Gln Cys Gly Lys Val Phe Lys Trp Pro Ser
450                 455                 460
```

```
Ser Leu Pro Ile His Met Arg Leu His Thr Gly Glu Lys Pro Tyr Gln
465                 470                 475                 480

Cys Lys His Cys Gly Lys Ala Phe Asn Cys Ser Ser Ser Leu Arg Arg
                485                 490                 495

His Val Arg Ile His Thr Thr Glu Lys Gln Tyr Lys Cys Asn Val Gly
                500                 505                 510

His Pro Pro Ala Asn Glu Phe Met Cys Ser Ala Ser Glu Lys Ser His
        515                 520                 525

Gln Glu Arg Asp Leu Ile Lys Val Val Asn Met Val Leu Pro Leu
        530                 535                 540

<210> SEQ ID NO 4
<211> LENGTH: 627
<212> TYPE: PRT
<213> ORGANISM: Homo sapiens
<220> FEATURE:
<221> NAME/KEY: DOMAIN
<222> LOCATION: (4)..(77)
<223> OTHER INFORMATION: Krab DOMAIN
<220> FEATURE:
<221> NAME/KEY: ZN_FING
<222> LOCATION: (171)..(193)
<223> OTHER INFORMATION: Zinc finger
<220> FEATURE:
<221> NAME/KEY: ZN_FING
<222> LOCATION: (199)..(221)
<223> OTHER INFORMATION: Zinc finger
<220> FEATURE:
<221> NAME/KEY: ZN_FING
<222> LOCATION: (227)..(249)
<223> OTHER INFORMATION: Zinc finger
<220> FEATURE:
<221> NAME/KEY: ZN_FING
<222> LOCATION: (255)..(277)
<223> OTHER INFORMATION: Zinc finger
<220> FEATURE:
<221> NAME/KEY: ZN_FING
<222> LOCATION: (283)..(305)
<223> OTHER INFORMATION: Zinc finger
<220> FEATURE:
<221> NAME/KEY: ZN_FING
<222> LOCATION: (311)..(333)
<223> OTHER INFORMATION: Zinc finger
<220> FEATURE:
<221> NAME/KEY: ZN_FING
<222> LOCATION: (339)..(361)
<223> OTHER INFORMATION: Zinc finger
<220> FEATURE:
<221> NAME/KEY: ZN_FING
<222> LOCATION: (367)..(389)
<223> OTHER INFORMATION: Zinc finger
<220> FEATURE:
<221> NAME/KEY: ZN_FING
<222> LOCATION: (395)..(417)
<223> OTHER INFORMATION: Zinc finger
<220> FEATURE:
<221> NAME/KEY: ZN_FING
<222> LOCATION: (423)..(445)
<223> OTHER INFORMATION: Zinc finger
<220> FEATURE:
<221> NAME/KEY: ZN_FING
<222> LOCATION: (451)..(473)
<223> OTHER INFORMATION: Zinc finger
<220> FEATURE:
<221> NAME/KEY: ZN_FING
<222> LOCATION: (479)..(501)
<223> OTHER INFORMATION: Zinc finger
<220> FEATURE:
<221> NAME/KEY: ZN_FING
<222> LOCATION: (507)..(529)
<223> OTHER INFORMATION: Zinc finger
```

```
<220> FEATURE:
<221> NAME/KEY: ZN_FING
<222> LOCATION: (535)..(557)
<223> OTHER INFORMATION: Zinc finger
<220> FEATURE:
<221> NAME/KEY: ZN_FING
<222> LOCATION: (563)..(585)
<223> OTHER INFORMATION: Zinc finger

<400> SEQUENCE: 4
```

| | | | | | | | | | | | | | | |
|---|---|---|---|---|---|---|---|---|---|---|---|---|---|---|
| Met | Asp | Ser | Val | Val | Phe | Glu | Asp | Val | Ala | Val | Asp | Phe | Thr | Leu | Glu |
| 1 | | | | 5 | | | | | 10 | | | | | 15 | |

| Glu | Trp | Ala | Leu | Leu | Asp | Ser | Ala | Gln | Arg | Asp | Leu | Tyr | Arg | Asp | Val |
| | | | 20 | | | | | 25 | | | | | 30 | | |

| Met | Leu | Glu | Thr | Phe | Gln | Asn | Leu | Ala | Ser | Val | Asp | Asp | Glu | Thr | Gln |
| | | | 35 | | | | | 40 | | | | | 45 | | |

| Phe | Lys | Ala | Ser | Gly | Ser | Val | Ser | Gln | Gln | Asp | Ile | Tyr | Gly | Glu | Lys |
| | 50 | | | | | 55 | | | | | 60 | | | | |

| Ile | Pro | Lys | Glu | Ser | Lys | Ile | Ala | Thr | Phe | Thr | Arg | Asn | Val | Ser | Trp |
| 65 | | | | | 70 | | | | | 75 | | | | | 80 |

| Ala | Ser | Val | Leu | Gly | Lys | Ile | Trp | Asp | Ser | Leu | Ser | Ile | Glu | Asp | Gln |
| | | | | 85 | | | | | 90 | | | | | 95 | |

| Thr | Thr | Asn | Gln | Gly | Arg | Asn | Leu | Arg | Asn | His | Gly | Leu | Glu | Arg | Leu |
| | | | | 100 | | | | | 105 | | | | | 110 | |

| Cys | Glu | Ser | Asn | Asp | Gln | Cys | Gly | Glu | Ala | Leu | Ser | Gln | Ile | Pro | His |
| | | | 115 | | | | | 120 | | | | | 125 | | |

| Leu | Asn | Leu | Tyr | Lys | Lys | Ile | Pro | Pro | Gly | Val | Lys | Gln | Tyr | Glu | Tyr |
| | | 130 | | | | | 135 | | | | | 140 | | | |

| Asn | Thr | Tyr | Gly | Lys | Val | Phe | Met | His | Arg | Arg | Thr | Ser | Leu | Lys | Ser |
| 145 | | | | | 150 | | | | | 155 | | | | | 160 |

| Pro | Ile | Thr | Val | His | Thr | Gly | His | Lys | Pro | Tyr | Gln | Cys | Gln | Glu | Cys |
| | | | | 165 | | | | | 170 | | | | | 175 | |

| Gly | Gln | Ala | Tyr | Ser | Cys | Arg | Ser | His | Leu | Arg | Met | His | Val | Arg | Thr |
| | | | 180 | | | | | 185 | | | | | 190 | | |

| His | Asn | Gly | Glu | Arg | Pro | Tyr | Val | Cys | Lys | Leu | Cys | Gly | Lys | Thr | Phe |
| | | | 195 | | | | | 200 | | | | | 205 | | |

| Pro | Arg | Thr | Ser | Ser | Leu | Asn | Arg | His | Val | Arg | Ile | His | Thr | Ala | Glu |
| | 210 | | | | | 215 | | | | | 220 | | | | |

| Lys | Thr | Tyr | Glu | Cys | Lys | Gln | Cys | Gly | Lys | Ala | Phe | Ile | Asp | Phe | Ser |
| 225 | | | | | 230 | | | | | 235 | | | | | 240 |

| Ser | Leu | Thr | Ser | His | Leu | Arg | Ser | His | Thr | Gly | Glu | Lys | Pro | Tyr | Lys |
| | | | | 245 | | | | | 250 | | | | | 255 | |

| Cys | Lys | Glu | Cys | Gly | Lys | Ala | Phe | Ser | Tyr | Ser | Ser | Thr | Phe | Arg | Arg |
| | | | 260 | | | | | 265 | | | | | 270 | | |

| His | Thr | Ile | Thr | His | Thr | Gly | Glu | Lys | Pro | Tyr | Lys | Cys | Lys | Glu | Cys |
| | | 275 | | | | | 280 | | | | | 285 | | | |

| Ala | Glu | Ala | Phe | Ser | Tyr | Ser | Ser | Thr | Phe | Arg | Arg | His | Met | Ile | Ser |
| | | 290 | | | | | 295 | | | | | 300 | | | |

| His | Thr | Gly | Glu | Lys | Pro | His | Lys | Cys | Lys | Glu | Cys | Gly | Glu | Ala | Phe |
| 305 | | | | | 310 | | | | | 315 | | | | | 320 |

| Ser | Tyr | Ser | Ser | Ala | Phe | Arg | Arg | His | Met | Ile | Thr | His | Thr | Gly | Glu |
| | | | | 325 | | | | | 330 | | | | | 335 | |

| Lys | Pro | Tyr | Glu | Cys | Lys | Gln | Cys | Gly | Lys | Thr | Phe | Ile | Tyr | Leu | Gln |
| | | | 340 | | | | | 345 | | | | | 350 | | |

| Ser | Phe | Arg | Arg | His | Glu | Arg | Ile | His | Thr | Gly | Glu | Lys | Pro | Tyr | Glu |
| | | 355 | | | | | 360 | | | | | 365 | | | |

```
Cys Lys Gln Cys Gly Lys Thr Phe Ile Tyr Pro Gln Ser Phe Arg Arg
370                 375                 380

His Glu Arg Thr His Gly Gly Glu Lys Pro Tyr Glu Cys Asn Gln Cys
385                 390                 395                 400

Gly Lys Ala Phe Ser His Pro Ser Ser Phe Arg Gly His Met Arg Val
            405                 410                 415

His Thr Gly Glu Lys Pro Tyr Glu Cys Lys Gln Cys Gly Lys Thr Phe
            420                 425                 430

Asn Trp Pro Ile Ser Leu Arg Lys His Met Arg Thr His Thr Arg Glu
            435                 440                 445

Lys Pro Tyr Glu Cys Lys Gln Cys Gly Lys Ala Phe Ser Leu Ser Ala
        450                 455                 460

Cys Phe Arg Glu His Val Arg Met His Pro Glu Asp Lys Ser Tyr Glu
465                 470                 475                 480

Cys Lys Leu Cys Gly Lys Ala Phe Tyr Cys His Ile Ser Leu Gln Lys
                485                 490                 495

His Met Arg Arg His Thr Ala Glu Lys Leu Tyr Lys Cys Lys Gln Cys
            500                 505                 510

Gly Lys Ala Phe Ser Trp Pro Glu Leu Leu Gln Gln His Val Arg Thr
            515                 520                 525

His Thr Val Glu Lys Pro Tyr Glu Cys Lys Glu Cys Gly Lys Val Phe
            530                 535                 540

Lys Trp Pro Ser Ser Leu Pro Ile His Met Arg Leu His Thr Gly Glu
545                 550                 555                 560

Lys Pro Tyr Gln Cys Lys His Cys Gly Lys Ala Phe Asn Cys Ser Ser
                565                 570                 575

Ser Leu Arg Arg His Val Arg Ile His Thr Thr Glu Lys Gln Tyr Lys
            580                 585                 590

Cys Asn Val Gly His Pro Pro Ala Asn Glu Phe Met Cys Ser Ala Ser
            595                 600                 605

Glu Lys Ser His Gln Glu Arg Asp Leu Ile Lys Val Val Asn Met Val
    610                 615                 620

Leu Pro Leu
625

<210> SEQ ID NO 5
<211> LENGTH: 25
<212> TYPE: DNA
<213> ORGANISM: artificial sequence
<220> FEATURE:
<223> OTHER INFORMATION: Inhibitory nucleic acid molecule

<400> SEQUENCE: 5
tgtgagaatg caccctgaag acaaa                                          25

<210> SEQ ID NO 6
<211> LENGTH: 25
<212> TYPE: DNA
<213> ORGANISM: Artificial sequence
<220> FEATURE:
<223> OTHER INFORMATION: Inhibitory nucleic acid molecule

<400> SEQUENCE: 6
tcctatgaat gcaagctatg tggga                                          25
```

```
<210> SEQ ID NO 7
<211> LENGTH: 25
<212> TYPE: DNA
<213> ORGANISM: Artificial sequence
<220> FEATURE:
<223> OTHER INFORMATION: Inhibitory nucleic acid molecule

<400> SEQUENCE: 7
aagctttcta ttgccacata tcctt                                 25

<210> SEQ ID NO 8
<211> LENGTH: 25
<212> TYPE: DNA
<213> ORGANISM: Artificial sequence
<220> FEATURE:
<223> OTHER INFORMATION: Inhibitory nucleic acid molecule

<400> SEQUENCE: 8
acaaaaacat atgagaagac atacc                                 25

<210> SEQ ID NO 9
<211> LENGTH: 25
<212> TYPE: DNA
<213> ORGANISM: Artificial sequence
<220> FEATURE:
<223> OTHER INFORMATION: Inhibitory nucleic acid molecule

<400> SEQUENCE: 9
gcagagaaac tctataaatg caagc                                 25

<210> SEQ ID NO 10
<211> LENGTH: 25
<212> TYPE: DNA
<213> ORGANISM: Artificial sequence
<220> FEATURE:
<223> OTHER INFORMATION: Inhibitory nucleic acid molecule

<400> SEQUENCE: 10
agtgtgggaa agctttcagt tggcc                                 25

<210> SEQ ID NO 11
<211> LENGTH: 25
<212> TYPE: DNA
<213> ORGANISM: Artificial sequence
<220> FEATURE:
<223> OTHER INFORMATION: Inhibitory nucleic acid molecule

<400> SEQUENCE: 11
tgaacttttg caacaacatg tgaga                                 25

<210> SEQ ID NO 12
<211> LENGTH: 25
<212> TYPE: DNA
<213> ORGANISM: Artificial sequence
<220> FEATURE:
<223> OTHER INFORMATION: Inhibitory nucleic acid molecule

<400> SEQUENCE: 12
acgcacactg tagagaagcc ctatg                                 25

<210> SEQ ID NO 13
<211> LENGTH: 25
<212> TYPE: DNA
<213> ORGANISM: Artificial sequence
<220> FEATURE:
<223> OTHER INFORMATION: Inhibitory nucleic acid molecule
```

<400> SEQUENCE: 13
aatgtaagga atgtgggaag gtctt                                      25

<210> SEQ ID NO 14
<211> LENGTH: 25
<212> TYPE: DNA
<213> ORGANISM: Artificial sequence
<220> FEATURE:
<223> OTHER INFORMATION: Inhibitory nucleic acid molecule

<400> SEQUENCE: 14
caaatggcca tcatctttac caata                                      25

<210> SEQ ID NO 15
<211> LENGTH: 25
<212> TYPE: DNA
<213> ORGANISM: Artificial sequence
<220> FEATURE:
<223> OTHER INFORMATION: Inhibitory nucleic acid molecule

<400> SEQUENCE: 15
catatgagac tgcacactgg agaga                                      25

<210> SEQ ID NO 16
<211> LENGTH: 25
<212> TYPE: DNA
<213> ORGANISM: Artificial sequence
<220> FEATURE:
<223> OTHER INFORMATION: Inhibitory nucleic acid molecule

<400> SEQUENCE: 16
aaccttatca atgtaagcat tgtgg                                      25

<210> SEQ ID NO 17
<211> LENGTH: 25
<212> TYPE: DNA
<213> ORGANISM: Artificial sequence
<220> FEATURE:
<223> OTHER INFORMATION: Inhibitory nucleic acid molecule

<400> SEQUENCE: 17
gaaagcattc aattgttcct catcc                                      25

<210> SEQ ID NO 18
<211> LENGTH: 25
<212> TYPE: DNA
<213> ORGANISM: Artificial sequence
<220> FEATURE:
<223> OTHER INFORMATION: Inhibitory nucleic acid molecule

<400> SEQUENCE: 18
ttaaggcgac atgtgagaat acaca                                      25

<210> SEQ ID NO 19
<211> LENGTH: 25
<212> TYPE: DNA
<213> ORGANISM: Artificial sequence
<220> FEATURE:
<223> OTHER INFORMATION: Inhibitory nucleic acid molecule

<400> SEQUENCE: 19
ctacagaaaa acagtataag tgtaa                                      25

```
<210> SEQ ID NO 20
<211> LENGTH: 29
<212> TYPE: DNA
<213> ORGANISM: Artificial sequence
<220> FEATURE:
<223> OTHER INFORMATION: Inhibitory nucleic acid molecule

<400> SEQUENCE: 20
tgtaggacat cctcctgcaa atgaattca                                       29

<210> SEQ ID NO 21
<211> LENGTH: 50
<212> TYPE: PRT
<213> ORGANISM: Artificial sequence
<220> FEATURE:
<223> OTHER INFORMATION: Target site

<400> SEQUENCE: 21

Ser Ser Ser Leu Arg Arg His Val Arg Ile His Thr Thr Glu Lys Gln
1               5                   10                  15

Tyr Lys Cys Asn Val Gly His Pro Pro Ala Asn Glu Phe Met Cys Ser
            20                  25                  30

Ala Ser Glu Lys Ser His Gln Glu Arg Asp Leu Ile Lys Val Val Asn
        35                  40                  45

Met Val
    50

<210> SEQ ID NO 22
<211> LENGTH: 27
<212> TYPE: DNA
<213> ORGANISM: Artificial sequence
<220> FEATURE:
<223> OTHER INFORMATION: Primer

<400> SEQUENCE: 22
gctagatctg aattcaccta gtggccc                                         27

<210> SEQ ID NO 23
<211> LENGTH: 23
<212> TYPE: DNA
<213> ORGANISM: Artificial sequence
<220> FEATURE:
<223> OTHER INFORMATION: Primer

<400> SEQUENCE: 23
tctaagcttc gcgcagtccc cga                                             23

<210> SEQ ID NO 24
<211> LENGTH: 17
<212> TYPE: DNA
<213> ORGANISM: Artificial sequence
<220> FEATURE:
<223> OTHER INFORMATION: Primer

<400> SEQUENCE: 24
acccaagcat gatatgg                                                    17

<210> SEQ ID NO 25
<211> LENGTH: 18
<212> TYPE: DNA
<213> ORGANISM: Artificial sequence
<220> FEATURE:
<223> OTHER INFORMATION: Primer
```

```
<400> SEQUENCE: 25
ttgactactg ctggagtg                                                 18

<210> SEQ ID NO 26
<211> LENGTH: 20
<212> TYPE: DNA
<213> ORGANISM: artificial sequence
<220> FEATURE:
<223> OTHER INFORMATION: Primer

<400> SEQUENCE: 26
gcttgatatt gttggtgagt                                               20

<210> SEQ ID NO 27
<211> LENGTH: 19
<212> TYPE: DNA
<213> ORGANISM: Artificial sequence
<220> FEATURE:
<223> OTHER INFORMATION: Primer

<400> SEQUENCE: 27
gacaaccgac ttctacaat                                                19

<210> SEQ ID NO 28
<211> LENGTH: 17
<212> TYPE: DNA
<213> ORGANISM: Artificial sequence
<220> FEATURE:
<223> OTHER INFORMATION: Primer

<400> SEQUENCE: 28
gttgttgttg agcctgg                                                  17

<210> SEQ ID NO 29
<211> LENGTH: 17
<212> TYPE: DNA
<213> ORGANISM: Artificial sequence
<220> FEATURE:
<223> OTHER INFORMATION: Artificial sequence

<400> SEQUENCE: 29
cctagaaggt caccgaa                                                  17

<210> SEQ ID NO 30
<211> LENGTH: 17
<212> TYPE: DNA
<213> ORGANISM: Artificial sequence
<220> FEATURE:
<223> OTHER INFORMATION: Primer

<400> SEQUENCE: 30
acggagactc gtttgga                                                  17

<210> SEQ ID NO 31
<211> LENGTH: 17
<212> TYPE: DNA
<213> ORGANISM: Artificial sequence
<220> FEATURE:
<223> OTHER INFORMATION: Primer

<400> SEQUENCE: 31
tggcccttcg attctga                                                  17
```

```
<210> SEQ ID NO 32
<211> LENGTH: 17
<212> TYPE: DNA
<213> ORGANISM: Artificial sequence
<220> FEATURE:
<223> OTHER INFORMATION: Primer

<400> SEQUENCE: 32
tggcccttcg attctga                                                  17

<210> SEQ ID NO 33
<211> LENGTH: 19
<212> TYPE: DNA
<213> ORGANISM: Artificial sequence
<220> FEATURE:
<223> OTHER INFORMATION: Primer

<400> SEQUENCE: 33
gtggaggtgg taggtcttt                                                19

<210> SEQ ID NO 34
<211> LENGTH: 17
<212> TYPE: DNA
<213> ORGANISM: Artificial sequence
<220> FEATURE:
<223> OTHER INFORMATION: Primer

<400> SEQUENCE: 34
tcccctgtag gcagaga                                                  17

<210> SEQ ID NO 35
<211> LENGTH: 18
<212> TYPE: DNA
<213> ORGANISM: Artificial sequence
<220> FEATURE:
<223> OTHER INFORMATION: Primer

<400> SEQUENCE: 35
cactgataac ccaggtga                                                 18

<210> SEQ ID NO 36
<211> LENGTH: 20
<212> TYPE: DNA
<213> ORGANISM: Artificial sequence
<220> FEATURE:
<223> OTHER INFORMATION: Primer

<400> SEQUENCE: 36
ccgcctgccc ctagcggtcc                                               20

<210> SEQ ID NO 37
<211> LENGTH: 23
<212> TYPE: DNA
<213> ORGANISM: Artificial sequence
<220> FEATURE:
<223> OTHER INFORMATION: Primer

<400> SEQUENCE: 37
tgagcagaat ccagcaaagc cca                                           23

<210> SEQ ID NO 38
<211> LENGTH: 20
<212> TYPE: DNA
<213> ORGANISM: Artificial sequence
<220> FEATURE:
<223> OTHER INFORMATION: Primer
```

-continued

<400> SEQUENCE: 38
gccagcaaac agatcagtgc                                              20

<210> SEQ ID NO 39
<211> LENGTH: 20
<212> TYPE: DNA
<213> ORGANISM: Artificial sequence
<220> FEATURE:
<223> OTHER INFORMATION: Primer

<400> SEQUENCE: 39
cccctccaga aggagaggaa                                              20

<210> SEQ ID NO 40
<211> LENGTH: 21
<212> TYPE: DNA
<213> ORGANISM: Artificial sequence
<220> FEATURE:
<223> OTHER INFORMATION: Primer

<400> SEQUENCE: 40
gaaacccgga agtggaactc t                                            21

<210> SEQ ID NO 41
<211> LENGTH: 20
<212> TYPE: DNA
<213> ORGANISM: Artificial sequence
<220> FEATURE:
<223> OTHER INFORMATION: Primer

<400> SEQUENCE: 41
cctgacagcc tacgtctctg                                              20

<210> SEQ ID NO 42
<211> LENGTH: 20
<212> TYPE: DNA
<213> ORGANISM: Artificial sequence
<220> FEATURE:
<223> OTHER INFORMATION: Primer

<400> SEQUENCE: 42
accacagtcc atgccatcac                                              20

<210> SEQ ID NO 43
<211> LENGTH: 20
<212> TYPE: DNA
<213> ORGANISM: Artificial sequence
<220> FEATURE:
<223> OTHER INFORMATION: Primer

<400> SEQUENCE: 43
ccagtgagct tcccgttcag                                              20

<210> SEQ ID NO 44
<211> LENGTH: 21
<212> TYPE: DNA
<213> ORGANISM: Artificial Sequence
<220> FEATURE:
<223> OTHER INFORMATION: shRNA

<400> SEQUENCE: 44
ccttcagtta ttcttcggct t                                            21

```
<210> SEQ ID NO 45
<211> LENGTH: 21
<212> TYPE: DNA
<213> ORGANISM: Artificial Sequence
<220> FEATURE:
<223> OTHER INFORMATION: shRNA

<400> SEQUENCE: 45
cctgaagaca aatcctatga a                                              21

<210> SEQ ID NO 46
<211> LENGTH: 21
<212> TYPE: DNA
<213> ORGANISM: Artificial Sequence
<220> FEATURE:
<223> OTHER INFORMATION: shRNA

<400> SEQUENCE: 46
ccatcatctt taccaataca t                                              21

<210> SEQ ID NO 47
<211> LENGTH: 8544
<212> TYPE: DNA
<213> ORGANISM: Homo sapiens

<400> SEQUENCE: 47
cgagctctgt ctaatcaggc ccctgggacg ggacgcctct gtcctagccg tgagtgcccc      60
gcctgcccct agcggtccct ggcgtcccgg ttcctgtcgc gctcacctgc gccggtagcg     120
aagaaatcgc cccgggacat ggactcagtg gtctttgagg atgtggctgt ggacttcacc     180
ctggaggagt gggctttgct ggattctgct cagagggacc tctacagaga tgtgatgctg     240
gagacctttc agaacctggc ctcagtagat gatgaaactc aatttaaggc cagtgggtca     300
gtttctcagc aggatatttta tggagagaaa atacccaagg aatctaaaat agccacgttc     360
accagaaatg tttcctggc ctctgtttta ggaaaaattt gggacagtct tagcatcgaa     420
gatcaaacca caaccaggg agaaaatctc agaaatcatg ggttggagag actctgtgaa     480
agtaatgatc aatgtggaga agccctcagc cagattccac atcttaatct gtacaagaaa     540
attccacctg gagtaaaaca gtatgaatac aacacgtacg gaaaagtctt catgcatcgc     600
cgcacatccc tcaagagtcc catcacagtt cacactggac acaaaccata tcagtgccag     660
gaatgtgggc aggcctacag ttgtcgttca cacctaagaa tgcatgtgag aacccacaat     720
ggagagagac cctatgtgtg taaattatgt gggaaaacct ttcctcgtac ttcctccctc     780
aatcggcatg taaggattca cactgctgag aaaacctacg aatgtaagca atgtgggaaa     840
gcctttattg acttctcaag tcttactagt catctcagaa gtcacaccgg agagaagcca     900
tataagtgta aggaatgtgg gaaagctttc agttattcct caacgtttcg aagacacaca     960
ataacacaca ctggcgagaa gccatataaa tgtaaggaat gtgcggaagc ctttagttat    1020
tcctcaactt ttcgaagaca tatgatttca cacactggag agaagccaca taatgtaaa    1080 gaatgtgggg aggccttcag ttattcttcg gcttttcgaa gacacatgat aacacacact    1140
ggagagaaac cctacgaatg caaacaatgt gggaaaacct tcatttatct ccagtccttt    1200
cgaagacatg aaaggattca cactggagag aaaccctacg aatgcaaaca gtgtgggaag    1260
accttcattt atcccagtc ctttcgaaga catgaaagga ctcatggtgg agagaaaccc    1320
tatgaatgca accagtgcgg gaaagcattc agtcacccct cctcctttcg aggacacatg    1380
agggtgcaca ctggagagaa accctatgag tgcaagcaat gtgggaaaac tttcaattgg    1440
```

```
cccatatctt tacgaaaaca tatgagaaca catactagag agaaaccctaa tgaatgtaag    1500 cagtgtggga aagccttcag cttgtctgct tgctttcgag aacatgtgag aatgcaccct    1560
gaagacaaat cctatgaatg caagctatgt gggaaagctt tctattgcca catatcctta    1620
caaaaacata tgagaagaca taccgcagag aaactctata aatgcaagca gtgtgggaaa    1680
gctttcagtt ggcctgaact tttgcaacaa catgtgagaa cgcacactgt agagaagccc    1740
tatgaatgta aggaatgtgg gaaggtcttc aaatggccat catctttacc aatacatatg    1800
agactgcaca ctggagagaa accttatcaa tgtaagcatt gtgggaaagc attcaattgt    1860
tcctcatcct taaggcgaca tgtgagaata cacactacag aaaaacagta taagtgtaat    1920
gtaggacatc ctcctgcaaa tgaattcatg tgcagtgctt cagaaaagtc acaccaggag    1980
agagatctga tcaaagttgt aaatatggtg ttgcctttat gagttcctta tcctgaaagt    2040
ggacactcaa ggagtgtgtc tgtagttcat ttgcaaataa acatttagtt gaaaaataat    2100
tctccaaata ctctcagcta tcctacatga atttgaacag gtagtttctt acgattcagt    2160
aaataaaact ttcatcttag agtgttttgg actcatggat gatttgaagt gtattttaa    2220 tatgcaagta ggttcaagtt ttatttaatt tcttaaattg taactgactt agtgtgacag    2280
gtattggata ttacgtatct attatatttt ccacctttt tactgggagt attttattg     2340 tttggccaga ggagccttat tccatttttt aagaagtagt tggcagaatt ttgtaattat    2400
gcaaagttgt ttaaggagta tagcctcaaa tgaattgtaa ttttttaatgt ttgcccattg   2460 ctgtttgtct ttgcttgtga ttgtgaattg dacagtaggc tttgacttgt gatgtgacgg    2520
agaaatccag agttgcagat agttcttctg cattgttgtc agtgtgggta gtgttaggaa    2580
cttcatttgc tggaatgcat ttcctttatg gttccatgtc caaatttacc aatagcaata    2640
acttgaatga aatttagaat gaagaagaag taagtcatcg ctgagctttt ggggtcacat    2700
taaatggaga tggacagatg catagggct ttgtgaacat caaccttcag cttatttccc     2760
agattcttat tcctgccaat caagagtacc atcaaaagaa acacttaagt gcttgatttc    2820
cactgtgtca gaggtgtagt cttcctcaga catctccatt aacttgatat tagggatatt    2880
cctgtgtggt cagtcaccta gagtctggat ttttctcaaa accctgcatg acctcttgac    2940
cactgattca gactgtcttg tttggcagtc tctgagcttc tgattctccc gttctgtaga    3000
tcttaacata tttgcatggg gtctaattta tatagtgaac accttgttat cttaatactt    3060
ccagtggctc tgtgatcctg attccaccac gaaagccaca gtgttgcagt caaagaagaa    3120
aaacaacaca tgggactttg taccctattg cattttaag tgtgcctgcc gagtcctatg     3180
tgagaacaaa taccttcctc atatattaga tttagggaga tttctgttac tcagaactaa    3240
atgcagtttc ttgatatagg ttaaattatt aggtttgatt atgtatcatt aaaaataatg    3300
tggattttgt ttcaaggaaa accttctgta gatatttctt agaaatatcc tgtttagctg    3360
ggcacagtag ctcatgcctg taatccctgc actttgggag gcttgaggtc aggagtttga    3420
gaccagcctg gttaacatgg tgaaaccctg tctctactaa aaacacaaaa attagccagg    3480
catggtggtg agtacctgta accccagcta cttgggaggc tgagacagga gaagtgcttg    3540
aacctaggag gcggaggttg cagtgagcca agatcacacc actgcactcc agcctgggag    3600
acggggaaag actccatcac acaagcaaga aaagaaaaaa aaatcctatt tactgtgctt    3660
tcaaattagt tgtttagaga ctatattaat ttcccagggc tgccataaca agtacaaaa    3720 actgggtgac ataggaaaac aaactttttg tttctcagtt ctggacccag aaatccagaa    3780
acaaggcatt ggcaggacca tgcttttct gaagatgcta gggaaggatc tgtttcagaa    3840
```

```
ctcacctagc ttctggtagt tccttagctt gtggcagcat aactctaatt ttcacatggc    3900
attctccctg tgtgtgtgtc tctccatgtg acaatatttt tatacataca caccactcat    3960
tgggttaggc cccactctac ttcagtatga ttttacctta actaattaca ttggcaacag    4020
ctctcttttc gcatactgag gcaccgcgaa ttaagatttc aacgtaaaaa ttttaggaga    4080
cccaattcaa cccataacac taagaaatgt tattttttgt ttaccgagag aattacagat    4140
ttcaaatcaa ctttgtaatt ttgataattt aagcatgtta cattttgaat cagtattacc    4200
aagtatatac aaatacaggt attttttcat ataaatgtta tttttaattg ctgtatactt    4260
aacatttgcc attaaaatga ttttttttt ttgagacaga gtctcgctct gtcacccagg    4320
ctggagtgca gtggcacgac cttagctcac tgcaaccttc atctcccagg ttcagttgat    4380
tctcctgcct cagcctcccg agtagttggg attacaggca tgcaccacca cacccagcta    4440 attttttat ttttggtaga gatggggttt caccatgttg gccaggctgg tcttgaactc    4500
ctgacctcag gtgatctgcc caccttggcc tcccaaagtg ttgggattac aggcatgagc    4560
caccacaccc ggcctaaaat gatttcttat ttgtggttaa taacaattaa aaagcggaaa    4620
taatggtttt gtcaaggccc tctacccaga aaccaccagg atcacactgg tagtcaaaga    4680
aaatttgctg tgttgagttg aagtttgaac acatgatcaa gaaagggctg tggcttgtat    4740
cagagggtgt ttaaaaggat ttactatcag atttggcctt gtgttctgtg attttggtga    4800
gcgttcaagg aagccaggct ttggtctgga ttggatgttc tcaggtcatg aatataattc    4860
tctgggaact cccaaagttc tcatctacaa agcagaagtt aattggagct gaaaactaat    4920
cagtaaagcc acagcagcca gtcatatggg ggagaagagg ggaatgtttg atggtttttg    4980
tggtttagag gtgagttccg gaaaaaaaga agacatgttt gacatcctca acgagaaaa    5040 tttttcatgt gttttatagg ccaaggaggc agaagctttt gttttaatga gccagaaagc    5100
cccaaaagcc tatttaagtt ttctcaggta tcatttcaac ctctgaactt ccagaattaa    5160
ctagggaaga ggaaaaacat gtaacacctt agagttttat taaagagcaa acaatatcca    5220
gtaatctcca ttactttcca tgttaacata gttttcata acgctctata gatgaatgtg    5280
atttggcagt cacttgtatt tcttaacacc cacttaccca tcattccctc ttagatgaaa    5340
aaagttaagc acggggacaa cagagtcttg tatattcatg tagctcatga tgatggaatc    5400
aagtttgaag gcttaacctg tgcttaacct atattgggca ttgtcaagac ttaaatttag    5460
aacactggaa agcaagtata attaatttta caaatagggc atcaaatttt acaaagactc    5520
ctaaggctat atggtattcc ttttataaga catggaaaag gcaaagataa gggaaacgaa    5580
caaatcgctg gttagaagta ggggatttga gtacatatgg gcttaagagt gttctgtcat    5640
gattgtagtg gtgaaaacaa gcatttgcaa aaactcataa ggctactctt aaaatagcaa    5700
attttgttgt atgtatattt taaagttaaa caataaaaat gctttcagtt tattaaagaa    5760
ctcaagacca ggtgcagtgg ctcatgccta atcccagc actttgggaa gctgaggcgg    5820
gaggattgct tgtggccagg aggttgaggc tgcagtgaac tatgatcatg cactgcactc    5880
tacactgggc gacagagcaa gaccctgtct caaaaaaaa ggaatacaaa acattcctga    5940
aacttgacat gtaagttcgc aataagactt ttccctagct gggcgcggtg actcatgcct    6000
gtaatctcaa cattttggga gactgaggca agaggatcac ttgaagtcag gagctagaca    6060
ccagtctggg caacatagcg agaccctcaac tctaccaaaa aattaaaaag tgagccaggc    6120
ggggtggtgc acgtctgtgg tcccagctac ttggcaggct gaagcaggag gatcacttga    6180
ggccttgagg agccatgatc gtgccactgc actccagctt gggtgacaga gcaagactgt    6240
```

```
ctcaaaaaat aaaaataaaa aaacaagact tcccccacca tcttggaatt ctctggagga    6300
aatgtagggc tggttgacaa ggacttgtgc ctcgtcagac cctgtttgaa acccagtctg    6360
aagttttgaa acacccacaa gggccatacc tgactttatc tcacgcacat aacaggagag    6420
aagaaggagg tcttccagaa tctgtctttg agtttacacc aggttcttcc catctgatct    6480
ttgggaatgc tgtggttctg aaacataaaa cggggaccct acacttcttc ccaggaatat    6540
cctgcctggg agcatcctga tcctgtcttc agacaagggg catccgcatc ttgttttcta    6600
gggccttttcc tgaggccact tccagctcca aagttctcat ctcaagctca gctctgtgtc    6660
ttcatgctgg gaaacgtctt tatggatccc caaactcctc ttgctgttgg aacacgtgg     6720
cagccctgcg ttgtgaggtg agagaagagg cagtggcaga acccatgcca tggagacacg    6780
cccatcagcc acagcagctc ctgctactgc ataaatccat aggcacaatc acacgcctca    6840
cggtgtcaac atctcccatg acatcacaaa gatgcccagc tgggacccac ctacagtgat    6900
ggggtgatgg ggtttcacct ataagcgggc aaacaggcac tcctcctcac tgtccagtca    6960
cctgacgtgc ttttctgcg cactcaggtc gtgacacccc aggaggtgcc tatcgcgccc    7020
caagctcctc acgtgcctcc tccccacagt ccaggacgcg tcttactaac gcctcaccag    7080
agcgcatgcg ccctcctcag gagcagcctc aaagcgcgca gcctcagccc attggcctgc    7140
gggaagtgga gttcccgaac agaagcccct cagtctccgg aagccccgcc cggcagactg    7200
ttcccaggat gcaacacggg ctcgcgtcta aaagagctgt gctttgttgg ggctatctgg    7260
gagtttccgc cttccatgaa gtgcgcaggc gcacttaggc gaggcggggc gactctagga    7320
agtggagaca tcaagagtgg tactggaagt ggcggaagct ctcctcttgc cctcttcagc    7380
ttccggtgtg gtgggtcccg gatatcgcgt ggctgtggca ggtagacagc ccgtgctcca    7440
gaggccttca tcttgtgatg gcagatgtac ttgagtagac acgacagacg gggaaggacc    7500
ctgatggtcc gagggacctt ccacagcaag tagaaggcac tgctgtgaat atgatggcgt    7560
cagaggtgac tgcaaaaaag gacagggcag ctgggcgagg aagagatacc agtgatgtcc    7620
taactgagct ccctgggtct ggtagtgagg agctcagtct tagaatatga gccgtgtcag    7680
gggctacagc atcatcactc ttgtcctgtc gcagactcag gctccctgtt ctcaggttct    7740
tatgtagaca gtgagggctc agggaggctc ccaccaccac caccaccagc accaccactc    7800
catcaaaacg gctgaaggac cttcctttag ggttcggggg atctcctcct tccacaaggg    7860
atggatgtga agacaactca ttctttgatg ttcagatggt tgtggccctc tgatgagatg    7920
tgtgcacacc ttgccaaatg catatgtctg ttgagcctgg acattaagta tttcttgatg    7980
ttcttctgtg taacaggtga tgtcctaggt gctgcagtga acagaagaga caaaatatcc    8040
ttgttccctt gaagctaatg tcgtaggggc ccaaaacaaa gcaaacaaac aaaaaaaagg    8100
aatgcaagtc aagtacactt tgtatggaca gtggtaattc ctaagaagga aaacaaagat    8160
ggacttaagg ggtgcagagg gcctggacta tgtgtgtctg tgggatagtc tgttactacc    8220
tctgggactc tcatctcttg agtgtgcttg ggtgtgtcca accgttttc ctagtgacaa      8280
agtctgggta attctgtggg gacatatatt ggtgtatctg ggaggtccca tgtgtctcag    8340
tggtggtccc tgttttcagg aaagagtgtc tgtgaatgtc catgtgtctc actgcacagc    8400
tgtgattttt ctgtgtctct gtgttttcca gtctttgtgt gatgaaatat aaaggcctag    8460
caggctcaga gttattaatg aattgtactt aagcgttgag aggcatatat ttattgcact    8520
attaaattct tccaaaatat agtt                                           8544
```

<210> SEQ ID NO 48
<211> LENGTH: 8547
<212> TYPE: DNA
<213> ORGANISM: Homo sapiens

<400> SEQUENCE: 48

| | | | | | |
|---|---|---|---|---|---|
| cgagctctgt | ctaatcaggc | ccctgggacg | ggacgcctct | gtcctagccg | tgagtgcccc | 60 |
| gcctgcccct | agcggtccct | ggcgtcccgg | ttcctgtcgc | gctcacctgc | gccggtagcg | 120 |
| aagaaatcgc | cccgggacat | ggactcagtg | gtctttgagg | atgtggctgt | ggacttcacc | 180 |
| ctggaggagt | gggctttgct | ggattctgct | cagagggacc | tctacagaga | tgtgatgctg | 240 |
| gagacctttc | agaacctggc | ctcagtagat | gatgaaactc | aatttaaggc | cagtgggtca | 300 |
| gtttctcagc | aggatatttta | tggagagaaa | atacccaagg | aatctaaaat | agccacgttc | 360 |
| accagaaatg | tttcctggc | ctctgtttta | ggaaaaattt | gggacagtct | tagcatcgaa | 420 |
| gatcaaacca | caaaccaggg | gagaaatctc | agtagaaatc | atgggttgga | gagactctgt | 480 |
| gaaagtaatg | atcaatgtgg | agaagccctc | agccagattc | cacatcttaa | tctgtacaag | 540 |
| aaaattccac | ctggagtaaa | acagtatgaa | tacaacacgt | acggaaaagt | cttcatgcat | 600 |
| cgccgcacat | ccctcaagag | tcccatcaca | gttcacactg | gacacaaacc | atatcagtgc | 660 |
| caggaatgtg | ggcaggccta | cagttgtcgt | tcacacctaa | gaatgcatgt | gagaacccac | 720 |
| aatggagaga | gaccctatgt | gtgtaaatta | tgtgggaaaa | cctttcctcg | tacttcctcc | 780 |
| ctcaatcggc | atgtaaggat | tcacactgct | gagaaaacct | acgaatgtaa | gcaatgtggg | 840 |
| aaagccttta | ttgacttctc | aagtcttact | agtcatctca | gaagtcacac | cggagagaag | 900 |
| ccatataagt | gtaaggaatg | tgggaaagct | ttcagttatt | cctcaacgtt | tcgaagacac | 960 |
| acaataacac | acactggcga | gaagccatat | aaatgtaagg | aatgtgcgga | agcctttagt | 1020 |
| tattcctcaa | cttttcgaag | acatatgatt | tcacacactg | gagagaagcc | acataaatgt | 1080 |
| aaagaatgtg | gggaggcctt | cagttattct | tcggcttttc | gaagacacat | gataacacac | 1140 |
| actggagaga | aaccctacga | atgcaaacaa | tgtgggaaaa | ccttcattta | tctccagtcc | 1200 |
| tttcgaagac | atgaaaggat | tcacactgga | gagaaaccct | acgaatgcaa | acagtgtggg | 1260 |
| aagaccttca | tttatcccca | gtcctttcga | agacatgaaa | ggactcatgg | tggagagaaa | 1320 |
| ccctatgaat | gcaaccagtg | cgggaaagca | ttcagtcacc | cctcctcctt | tcgaggacac | 1380 |
| atgagggtgc | acactggaga | gaaacccctat | gagtgcaagc | aatgtgggaa | aacttttcaat | 1440 |
| tggcccatat | ctttacgaaa | acatatgaga | acacatacta | gagagaaacc | ctatgaatgt | 1500 |
| aagcagtgtg | ggaaagcctt | cagcttgtct | gcttgctttc | gagaacatgt | gagaatgcac | 1560 |
| cctgaagaca | aatcctatga | atgcaagcta | tgtgggaaag | cttctctattg | ccacatatcc | 1620 |
| ttacaaaaac | atatgagaag | cataccgca | gagaaactct | ataaatgcaa | gcagtgtggg | 1680 |
| aaagctttca | gttggcctga | acttttgcaa | caacatgtga | aacgcacac | tgtagagaag | 1740 |
| ccctatgaat | gtaaggaatg | tgggaaggtc | ttcaaatggc | catcatcttt | accaatacat | 1800 |
| atgagactgc | acactggaga | gaaaccttat | caatgtaagc | attgtgggaa | agcattcaat | 1860 |
| tgttcctcat | ccttaaggcg | acatgtgaga | atacacacta | cagaaaaaca | gtaaagtgt | 1920 |
| aatgtaggac | atcctcctgc | aaatgaattc | atgtgcagtg | cttcagaaaa | gtcacaccag | 1980 |
| gagagagatc | tgatcaaagt | tgtaaatatg | gtgttgcctt | tatgagttcc | ttatcctgaa | 2040 |
| agtggacact | caaggagtgt | gtctgtagtt | catttgcaaa | taacatttta | gttgaaaaat | 2100 |
| aattctccaa | atactctcag | ctatcctaca | tgaatttgaa | caggtagttt | cttacgattc | 2160 |

```
agtaaataaa actttcatct tagagtgttt tggactcatg gatgatttga agtgtatttt    2220
taatatgcaa gtaggttcaa gttttattta atttcttaaa ttgtaactga cttagtgtga    2280
caggtattgg atattacgta tctattatat tttccacctt ttttactggg agtatttta    2340 ttgtttggcc agaggagcct tattccattt tttaagaagt agttggcaga attttgtaat    2400
tatgcaaagt tgtttaagga gtatagcctc aaatgaattg taattttaa tgtttgccca    2460 ttgctgtttg tctttgcttg tgattgtgaa ttggacagta ggctttgact tgtgatgtga    2520
cggagaaatc cagagttgca gatagttctt ctgcattgtt gtcagtgtgg gtagtgttag    2580
gaacttcatt tgctggaatg catttccttt atggttccat gtccaaattt accaatagca    2640
ataacttgaa tgaaatttag aatgaagaag aagtaagtca tcgctgagct tttggggtca    2700
cattaaatgg agatggacag atgcataggg gctttgtgaa catcaaccct cagcttattt    2760
tccagattct tattcctgcc aatcaagagt accatcaaaa gaaacactta agtgcttgat    2820
ttccactgtg tcagaggtgt agtcttcctc agacatctcc attaacttga tattagggat    2880
attcctgtgt ggtcagtcac ctagagtctg gattttctc aaaaccctgc atgacctctt    2940
gaccactgat tcagactgtc ttgtttggca gtctctgagc ttctgattct cccgttctgt    3000
agatcttaac atatttgcat ggggtctaat ttatatagtg aacaccttgt tatcttaata    3060
cttccagtgg ctctgtgatc ctgattccac cacgaaagcc acagtgttgc agtcaaagaa    3120
gaaaaacaac acatgggact ttgtacccta ttgcattttt aagtgtgcct gccgagtcct    3180
atgtgagaac aaataccttc ctcatatatt agatttaggg agattctgt tactcagaac    3240 taaatgcagt ttcttgatat aggttaaatt attaggtttg attatgtatc attaaaaata    3300
atgtggattt tgtttcaagg aaaaccttct gtagatattt cttagaaata tcctgtttag    3360
ctgggcacag tagctcatgc ctgtaatccc tgcactttgg gaggcttgag gtcaggagtt    3420
tgagaccagc ctggttaaca tggtgaaacc ctgtctctac taaaaacaca aaaattagcc    3480
aggcatggtg gtgagtacct gtaacccag ctacttggga ggctgagaca ggagaagtgc    3540
ttgaacctag gaggcggagg ttgcagtgag ccaagatcac accactgcac tccagcctgg    3600
gagacgggga aagactccat cacacaagca agaaaagaaa aaaaaatcct atttactgtg    3660 cttttcaaatt agttgtttag agactatatt aatttcccag ggctgccata acaaagtaca    3720
aaaactgggt gacataggaa aacaaacttt ttgtttctca gttctggacc cagaaatcca    3780
gaaacaaggc attggcagga ccatgctttt tctgaagatg ctagggaagg atctgtttca    3840
gaactcacct agcttctggt agttccttag cttgtggcag cataactcta attttcacat    3900
ggcattctcc ctgtgtgtgt gtctctccat gtgacaatat tttatacat acacaccact    3960 cattgggtta ggccccactc tacttcagta tgattttacc ttaactaatt acattggcaa    4020
cagctctctt ttcgcatact gaggcaccgc gaattaagat ttcaacgtaa aaattttagg    4080
agacccaatt caaccataa cactaagaaa tgttatttt tgtttaccga gagaattaca    4140
gatttcaaat caactttgta atttgataa ttttaagcatg ttacattttg aatcagtatt    4200
accaagtata tacaaataca ggtattttt catataaatg ttattttaa ttgctgtata    4260 cttaacattt gccattaaaa tgatttttt tttttgagac agagtctcgc tctgtcaccc    4320
aggctggagt gcagtggcac gaccttagct cactgcaacc ttcatctccc aggttcagtt    4380
gattctcctg cctcagcctc ccgagtagtt gggattacag gcatgcacca ccacacccag    4440 ctaattttt tattttggt agagatgggg tttcaccatg ttggccaggc tggtcttgaa    4500
ctcctgacct caggtgatct gcccaccttg gcctcccaaa gtgttgggat tacaggcatg    4560
```

```
agccaccaca cccggcctaa aatgatttct tatttgtggt taataacaat taaaaagcgg    4620
aaataatggt tttgtcaagg ccctctaccc agaaaccacc aggatcacac tggtagtcaa    4680
agaaaatttg ctgtgttgag ttgaagtttg aacacatgat caagaaaggg ctgtggcttg    4740
tatcagaggg tgtttaaaag gatttactat cagatttggc cttgtgttct gtgattttgg    4800
tgagcgttca aggaagccag gctttggtct ggattggatg ttctcaggtc atgaatataa    4860
ttctctggga actcccaaag ttctcatcta caaagcagaa gttaattgga gctgaaaact    4920
aatcagtaaa gccacagcag ccagtcatat gggggagaag aggggaatgt ttgatggttt    4980
ttgtggttta gaggtgagtt ccggaaaaaa agaagacatg tttgacatcc tcaaacgaga    5040 aaattttttca tgtgttttat aggccaagga ggcagaagct tttgttttaa tgagccagaa    5100
```
(Note: corrected — line at 5100 should read)
```
aaattttca tgtgttttat aggccaagga ggcagaagct tttgttttaa tgagccagaa    5100
agccccaaaa gcctatttaa gttttctcag gtatcatttc aacctctgaa cttccagaat    5160
taactaggga agaggaaaaa catgtaacac cttagagttt tattaaagag caaacaatat    5220
ccagtaatct ccattacttt ccatgttaac ataagttttc ataacgctct atagatgaat    5280
gtgatttggc agtcacttgt atttcttaac acccacttac ccatcattcc ctcttagatg    5340
aaaaaagtta agcacgggga caacagagtc ttgtatattc atgtagctca tgatgatgga    5400
atcaagtttg aaggcttaac ctgtgcttaa cctatattgg gcattgtcaa gacttaaatt    5460
tagaacactg gaaagcaagt ataattaatt ttacaaatag ggcatcaaat tttacaaaga    5520
ctcctaaggc tatatggtat tcctttata agacatggaa aaggcaaaga taagggaaac    5580
gaacaaatcg ctggttagaa gtaggggatt tgagtacata tgggcttaag agtgttctgt    5640
catgattgta gtggtgaaaa caagcatttg caaaaactca taaggctact cttaaaatag    5700
caaattttgt tgtatgtata ttttaaagtt aaacaataaa aatgctttca gtttattaaa    5760
gaactcaaga ccaggtgcag tggctcatgc ctataatccc agcactttgg gaagctgagg    5820
cgggaggatt gcttgtggcc aggaggttga ggctgcagtg aactatgatc atgcactgca    5880
ctctacactg ggcgacagag caagaccctg tctcaaaaaa aaaggaatac aaaacattcc    5940
tgaaacttga catgtaagtt cgcaataaga cttttcccta gctgggcgcg gtgactcatg    6000
cctgtaatct caacatttg ggagactgag gcaagaggat cacttgaagt caggagctag    6060
acaccagtct gggcaacata gcgagacctc aactctacca aaaaattaaa aagtgagcca    6120 ggcgggggtgg tgcacgtctg tggtcccagc tacttggcag gctgaagcag gaggatcact    6180
tgaggccttg aggagccatg atcgtgccac tgcactccag cttgggtgac agagcaagac    6240
tgtctcaaaa aataaaaata aaaaaacaag acttccccca ccatcttgga attctctgga    6300
ggaaatgtag ggctggttga caaggacttg tgcctcgtca gaccctgttt gaaacccagt    6360
ctgaagtttt gaaacaccca aagggccat acctgacttt atctcacgca cataacagga    6420
gagaagaagg aggtcttcca gaatctgtct ttgagtttac accaggttct tcccatctga    6480
tctttgggaa tgctgtggtt ctgaaacata aaacggggac cctacacttc ttcccaggaa    6540
tatcctgcct gggagcatcc tgatcctgtc ttcagacaag gggcatccgc atcttgtttt    6600
ctagggcctt tcctgaggcc acttccagct ccaaagttct catctcaagc tcagctctgt    6660
gtcttcatgc tgggaaacgt ctttatggat ccccaaactc ctcttgctgt tgggaacacg    6720
tggcagccct gcgttgtgag gtgagagaag aggcagtggc agaacccatg ccatggagac    6780
acgcccatca gccacagcag ctcctgctac tgcataaatc cataggcaca atcacacgcc    6840
tcacggtgtc aacatctccc atgacatcac aaagatgccc agctgggacc cacctacagt    6900
gatggggtga tggggtttca cctataagcg ggcaaacagg cactcctcct cactgtccag    6960
```

```
tcacctgacg tgcttttttct gcgcactcag gtcgtgacac cccaggaggt gcctatcgcg    7020 cccccaagctc ctcacgtgcc tcctccccac agtccaggac gcgtcttact aacgcctcac    7080
cagagcgcat gcgccctcct caggagcagc ctcaaagcgc gcagcctcag cccattggcc    7140
tgcgggaagt ggagttcccg aacagaagcc cctcagtctc cggaagcccc gcccggcaga    7200
ctgttcccag gatgcaacac gggctcgcgt ctaaaagagc tgtgctttgt tggggctatc    7260
tgggagtttc cgccttccat gaagtgcgca ggcgcactta ggcgaggcgg ggcgactcta    7320
ggaagtggag acatcaagag tggtactgga agtggcggaa gctctcctct tgccctcttc    7380
agcttccggt gtggtgggtc ccggatatcg cgtggctgtg caggtagac agcccgtgct     7440 ccagaggcct tcatcttgtg atggcagatg tacttgagta gacacgacag acggggaagg    7500
accctgatgg tccgagggac cttccacagc aagtagaagg cactgctgtg aatatgatgg    7560
cgtcagaggt gactgcaaaa aaggacaggg cagctgggcg aggaagagat accagtgatg    7620
tcctaactga gctccctggg tctggtagtg aggagctcag tcttagaata tgagccgtgt    7680
caggggctac agcatcatca ctcttgtcct gtcgcagact caggctccct gttctcaggt    7740
tcttatgtag acagtgaggg ctcagggagg ctcccaccac caccaccacc agcaccacca    7800
ctccatcaaa acggctgaag gaccttcctt tagggttcgg gggatctcct ccttccacaa    7860
gggatggatg tgaagacaac tcattctttg atgttcagat ggttgtggcc ctctgatgag    7920
atgtgtgcac accttgccaa atgcatatgt ctgttgagcc tggacattaa gtatttcttg    7980
atgttcttct gtgtaacagg tgatgtccta ggtgctgcag tgaacagaag agacaaaata    8040
tccttgttcc cttgaagcta atgtcgtagg ggcccaaaac aaagcaaaca aacaaaaaaa    8100
aggaatgcaa gtcaagtaca ctttgtatgg acagtggtaa ttcctaagaa ggaaaacaaa    8160
gatggactta aggggtgcag agggcctgga ctatgtgtgt ctgtgggata gtctgttact    8220
acctctggga ctctcatctc ttgagtgtgc ttgggtgtgt ccaaccgttt ttcctagtga    8280
caaagtctgg gtaattctgt ggggacatat attggtgtat ctgggaggtc ccatgtgtct    8340
cagtggtggt ccctgttttc aggaaagagt gtctgtgaat gtccatgtgt ctcactgcac    8400
agctgtgatt tttctgtgtc tctgtgtttt ccagtctttg tgtgatgaaa tataaaggcc    8460
tagcaggctc agagttatta atgaattgta cttaagcgtt gagaggcata tatttattgc    8520
actattaaat tcttccaaaa tatagtt                                        8547
```

<210> SEQ ID NO 49
<211> LENGTH: 2525
<212> TYPE: DNA
<213> ORGANISM: Homo sapiens
<400> SEQUENCE: 49

```
tagcttatgc cagccaaggg ccaactttgc aggcaggact ttctaaggtt aggggccctc      60
aggcctttgg gttggctctt cctgcgtcca ccccctagcc cactgcacag gtgtctctac     120
cacagaatta ttatgggagg cccctatgaa gtaggaggag accacactgc agtaatgatt     180
tcacttgtgc tgtttagggc tcctggactt agccaggact cagtggtctt tgaggatgtg     240
gctgtggact caccctgga ggagtgggct ttgctggatt ctgctcagag ggacctctac      300
agagatgtga tgctggagac ctttcagaac ctggcctcag tagatgatga aactcaattt     360
aaggccagtg ggtcagtttc tcagcaggat atttatggag agaaaatacc caaggaatct     420
aaaatagcca cgttcaccag aaatgttccc tgggcctctg ttttaggaaa atttgggac      480 agtcttagca tcgaagatca aaccacaaac caggggagaa atctcagtag aaatcatggg    540
```

```
ttggagagac tctgtgaaag taatgatcaa tgtggagaag ccctcagcca gattccacat    600
cttaatctgt acaagaaaat tccacctgga gtaaaacagt atgaatacaa cacgtacgga    660
aaagtcttca tgcatcgccg cacatccctc aagagtccca tcacagttca cactggacac    720
aaaccatatc agtgccagga atgtgggcag gcctacagtt gtcgttcaca cctaagaatg    780
catgtgagaa cccacaatgg agagagaccc tatgtgtgta aattatgtgg gaaaaccttt    840
cctcgtactt cctccctcaa tcggcatgta aggattcaca ctgctgagaa acctacgaa     900 tgtaagcaat gtgggaaagc ctttattgac ttctcaagtc ttactagtca tctcagaagt    960
cacaccggag agaagccata taagtgtaag gaatgtggga agctttcag ttattcctca    1020 acgtttcgaa gacacacaat aacacacact ggcgagaagc catataaatg taaggaatgt   1080
gcggaagcct ttagttattc ctcaactttt cgaagacata tgatttcaca cactggagag   1140
aagccacata aatgtaaaga atgtggggag gccttcagtt attcttcggc ttttcgaaga   1200
cacatgataa cacacactgg agagaaaccc tacgaatgca acaatgtgg gaaaaccttc    1260 atttatctcc agtcctttcg aagacatgaa aggattcaca ctggagagaa accctacgaa   1320
tgcaaacagt gtgggaagac cttcatttat ccccagtcct ttcgaagaca tgaaaggact   1380
catggtggag agaaacccta tgaatgcaac cagtgcggga agcattcag tcaccctcc    1440 tcctttcgag gacacatgag ggtgcacact ggagagaaac cctatgagtg caagcaatgt   1500
gggaaaactt tcaattggcc catatctta cgaaaacata tgagaacaca tactagagag   1560
aaaccctatg aatgtaagca gtgtgggaaa gccttcagct tgtctgcttg ctttcgagaa   1620
catgtgagaa tgcaccctga agacaaatcc tatgaatgca agctatgtgg gaaagctttc   1680
tattgccaca tatccttaca aaaacatatg agaagacata ccgcagagaa actctataaa   1740
tgcaagcagt gtgggaaagc tttcagttgg cctgaacttt tgcaacaaca tgtgagaacg   1800
cacactgtag agaagcccta tgaatgtaag gaatgtggga aggtcttcaa atggccatca   1860
tctttaccaa tacatatgag actgcacact ggagagaaac cttatcaatg taagcattgt   1920
gggaaagcat tcaattgttc ctcatcctta aggcgacatg tgagaataca cactacagaa   1980
aaacagtata gtgtaatgt aggacatcct cctgcaaatg aattcatgtg cagtgcttca   2040
gaaaagtcac accaggagag agatctgatc aaagttgtaa atatggtgtt gcctttatga   2100
gttccttatc ctgaaagtgg acactcaagg agtgtgtctg tagttcattt gcaaataaac   2160
atttagttga aaaataattc tccaaatact ctcagctatc ctacatgaat ttgaacaggt   2220
agtttcttac gattcagtaa ataaaacttt catcttagag tgttttggac tcatggatga   2280
tttgaagtgt atttttaata tgcaagtagg ttcaagtttt atttaatttc ttaaattgta   2340
actgacttag tgtgacaggt attggatatt acgtatctat tatatttcc accttttta    2400 ctgggagtat ttttattgtt tggccagagg agccttattc cattttttaa gaagtagttg   2460
gcagaatttt gtaattatgc aaagttgttt aaggagtata gcctcaaatg aattgtaatt   2520
tttaa                                                              2525
```

<210> SEQ ID NO 50
<211> LENGTH: 2523
<212> TYPE: DNA
<213> ORGANISM: Homo sapiens

<400> SEQUENCE: 50

```
ctagcttatg ccagccaagg gccaactttg caggcaggac tttctaaggt tagggggccct    60 caggcctttg ggttggctct tcctgcgtcc accccctagc ccactgcaca ggtgtctcta    120
```

```
ccacagaatt attatgggag gccctatga agtaggagga gaccacactg cagtaatgat      180
ttcacttgtg ctgtttaggg ctcctggact tagccaggac tcagtggtct ttgaggatgt      240
ggctgtggac ttcaccctgg aggagtgggc tttgctggat tctgctcaga gggacctcta      300
cagagatgtg atgctggaga cctttcagaa cctggcctca gtagatgatg aaactcaatt      360
taaggccagt gggtcagttt ctcagcagga tatttatgga gagaaaatac caaggaatc       420 taaaatagcc acgttcacca gaaatgtttc ctgggcctct gttttaggaa aaatttggga      480
cagtcttagc atcgaagatc aaaccacaaa ccaggggaga atctcagaa atcatgggtt       540 ggagagactc tgtgaaagta atgatcaatg tggagaagcc ctcagccaga ttccacatct      600
taatctgtac aagaaaattc cacctggagt aaaacagtat gaatacaaca cgtacggaaa      660
agtcttcatg catcgccgca catccctcaa gagtcccatc acagttcaca ctggacacaa      720
accatatcag tgccaggaat gtgggcaggc ctacagttgt cgttcacacc taagaatgca      780
tgtgagaacc cacaatggag agagaccta tgtgtgtaaa ttatgtggga aaaccttcc       840 tcgtacttcc tccctcaatc ggcatgtaag gattcacact gctgagaaaa cctacgaatg      900
taagcaatgt gggaaagcct ttattgactt ctcaagtctt actagtcatc tcagaagtca      960
caccggagag aagccatata agtgtaagga atgtgggaaa gctttcagtt attcctcaac     1020
gtttcgaaga cacacaataa cacacactgg cgagaagcca tataaatgta aggaatgtgc     1080
ggaagccttt agttattcct caacttttcg aagacatatg atttcacaca ctggagagaa     1140
gccacataaa tgtaaagaat gtggggaggc cttcagttat tcttcggctt ttcgaagaca     1200
catgataaca cacactggag agaaaccta cgaatgcaaa caatgtggga aaccttcat      1260 ttatctccag tcctttcgaa gacatgaaag gattcacact ggagagaaac cctacgaatg     1320
caaacagtgt gggaagacct tcatttatcc ccagtccttt cgaagacatg aaaggactca     1380
tggtggagag aaaccctatg aatgcaacca gtgcgggaaa gcattcagtc acccctcctc     1440
ctttcgagga cacatgaggg tgcacactgg agagaaaccc tatgagtgca agcaatgtgg     1500
gaaaactttc aattggccca tatctttacg aaaacatatg agaacacata ctagagagaa     1560 acctatgaa tgtaagcagt gtgggaaagc cttcagcttg tctgcttgct ttcgagaaca     1620
tgtgagaatg caccctgaag acaaatccta tgaatgcaag ctatgtggga agctttcta     1680 ttgccacata tccttacaaa aacatatgag aagacatacc gcagagaaac tctataaatg     1740
caagcagtgt gggaaagctt tcagttggcc tgaactttg caacaacatg tgagaacgca     1800
cactgtagag aagcccctatg aatgtaagga atgtgggaag gtcttcaaat ggccatcatc     1860
tttaccaata catatgagac tgcacactgg agagaaacct atcaatgta agcattgtgg      1920 gaaagcattc aattgttcct catccttaag gcgacatgtg agaatacaca ctacagaaaa     1980
acagtataag tgtaatgtag gacatcctcc tgcaaatgaa ttcatgtgca gtgcttcaga     2040
aaagtcacac caggagagag atctgatcaa agttgtaaat atggtgttgc ctttatgagt     2100
tccttatcct gaaagtggac actcaaggag tgtgtctgta gttcatttgc aaataaacat     2160
ttagttgaaa ataattctc caaatactct cagctatcct acatgaattt gaacaggtag      2220
tttcttacga ttcagtaaat aaaactttca tcttagagtg ttttggactc atggatgatt     2280
tgaagtgtat ttttaatatg caagtaggtt caagttttat ttaatttctt aaattgtaac     2340
tgacttagtg tgcaggtat tggatattac gtatctatta tattttccac cttttttact      2400
gggagtattt ttattgtttg gccagaggag ccttattcca ttttttaaga agtagttggc     2460
```

```
agaattttgt aattatgcaa agttgtttaa ggagtatagc ctcaaatgaa ttgtaatttt    2520
taa                                                                  2523

<210> SEQ ID NO 51
<211> LENGTH: 2369
<212> TYPE: DNA
<213> ORGANISM: Homo sapiens

<400> SEQUENCE: 51
ctgagtcccg gttttccttc ttgaggactt cttgtcccct ctgaccccaa gatgcctggg      60
gactcagtgg tctttgagga tgtggctgtg gacttcaccc tggaggagtg ggctttgctg     120
gattctgctc agagggacct ctacagagat gtgatgctgg agacctttca gaacctggcc     180
tcagtagatg atgaaactca atttaaggcc agtgggtcag tttctcagca ggatatttat     240
ggagagaaaa tacccaagga atctaaaata gccacgttca ccagaaatgt ttcctgggcc     300
tctgttttag gaaaaatttg gacagtctt agcatcgaag atcaaccac aaaccagggg       360 agaaatctca gtagaaatca tgggttggag agactctgtg aaagtaatga tcaatgtgga     420
gaagccctca gccagattcc acatcttaat ctgtacaaga aaattccacc tggagtaaaa     480
cagtatgaat acaacacgta cggaaaagtc ttcatgcatc gccgcacatc cctcaagagt     540
cccatcacag ttcacactgg acacaaacca tatcagtgcc aggaatgtgg gcaggcctac     600
agttgtcgtt cacacctaag aatgcatgtg agaacccaca atggagagag accctatgtg     660
tgtaaattat gtgggaaaac ctttcctcgt acttcctccc tcaatcggca tgtaaggatt     720
cacactgctg agaaaaccta cgaatgtaag caatgtggga agcctttat tgacttctca     780 agtcttacta gtcatctcag aagtcacacc ggagagaagc catataagtg taaggaatgt     840
gggaaagctt tcagttattc ctcaacgttt cgaagacaca caataacaca cactggcgag     900
aagccatata atgtaagga atgtgcggaa gcctttagtt attcctcaac ttttcgaaga     960
catatgattt cacacactgg agagaagcca cataaatgta agaatgtggg gaggccttc    1020 agttattctt cggcttttcg aagacacatg ataacacaca ctggagagaa accctacgaa    1080
tgcaaacaat gtgggaaaac cttcattat ctccagtcct ttcgaagaca tgaaggatt     1140 cacactggag agaaacccta cgaatgcaaa cagtgtggga agaccttcat ttatccccag    1200
tcctttcgaa gacatgaaag gactcatggt ggagagaaac cctatgaatg caaccagtgc    1260
gggaaagcat tcagtcaccc ctcctccttt cgaggacaca tgagggtgca cactggagag    1320
aaaccctatg agtgcaagca atgtgggaaa actttcaatt ggcccatatc tttacgaaaa    1380
catatgagaa cacatactag agagaaaccc tatgaatgta agcagtgtgg gaaagccttc    1440
agcttgtctg cttgctttcg agaacatgtg agaatgcacc ctgaagacaa atcctatgaa    1500
tgcaagctat gtgggaaagc tttctattgc cacatatcct acaaaaaca tatgagaaga    1560 cataccgcag agaaactcta taatgcaag cagtgtggga agctttcag ttggcctgaa     1620 cttttgcaac aacatgtgag aacgcacact gtagagaagc cctatgaatg taaggaatgt    1680
gggaaggtct tcaaatggcc atcatctta ccaatacata tgagactgca cactggagag    1740
aaaccttatc aatgtaagca ttgtgggaaa gcattcaatt gttcctcatc cttaaggcga    1800
catgtgagaa tacacactac agaaaaacag tataagtgta atgtaggaca tcctcctgca    1860
aatgaattca tgtgcagtgc ttcagaaaag tcacaccagg agagatct gatcaaagtt     1920 gtaaatatgg tgttgccttt atgagttcct tatcctgaaa gtggacactc aaggagtgtg    1980
tctgtagttc atttgcaaat aaacatttag ttgaaaaata attctccaaa tactctcagc    2040
```

```
tatcctacat gaatttgaac aggtagtttc ttacgattca gtaaataaaa ctttcatctt    2100
agagtgtttt ggactcatgg atgatttgaa gtgtattttt aatatgcaag taggttcaag    2160
ttttatttaa tttcttaaat tgtaactgac ttagtgtgac aggtattgga tattacgtat    2220
ctattatatt ttccacctttt tttactggga gtatttttat tgtttggcca gaggagcctt    2280
attccatttt ttaagaagta gttggcagaa ttttgtaatt atgcaaagtt gtttaaggag    2340
tatagcctca aatgaattgt aatttttaa                                      2369
```

THERAPEUTIC METHODS, PRODUCTS AND COMPOSITIONS INHIBITING ZNF555

CROSS-REFERENCE TO RELATED APPLICATION

This application is the U.S. national stage application of International Patent Application No. PCT/EP2016/058828, filed Apr. 21, 2016.

The Sequence Listing for this application is labeled "Seq-List.txt" which was created on Oct. 17, 2017 and is 61 KB. The entire content of the sequence listing is incorporated herein by reference in its entirety.

FIELD OF THE INVENTION

The present invention features products and compositions as well as their therapeutic uses in human or veterinary medicine. In particular, the invention provides ZNF555 as a new therapeutic target for the prevention or treatment of the diseases related to the ANT1 (SLC25A4) gene deregulation such as myopathy, Rett syndrome, cancer etc., and provides novel therapeutic methods and compositions based on a modulation of this factor. The invention particularly provides compositions and methods suitable to inhibit ZNF555 or ANT1 expression or activity and prevent or treat a musculoskeletal disease, typically Facioscapulohumeral Dystrophy (FSHD), in a subject. Also provided are methods to develop drugs able to specifically prevent or treat a musculoskeletal disease typically FSHD.

BACKGROUND

The myopathies are neuromuscular disorders in which the primary symptom is muscle weakness due to dysfunction of muscle fiber. Other symptoms of myopathy can include muscle cramps, stiffness, and spasms. Myopathies can be inherited (such as the muscular dystrophies, MD) or acquired (such as common muscle cramps). Currently, more than 100 diseases have similarities to MD, among them nine diseases are traditionally classified as muscular dystrophies including Facioscapulohumeral Dystrophy (FSHD).

FSHD is an autosomal dominant muscular dystrophy with an incidence of 3.2-4.6 per 100,000 throughout the world (1). FSHD is clinically characterized by a progressive muscular weakness in an up-to-down manner involving face, pectoral girdle, upper limbs, lower limbs and hips and most often begins in childhood and adolescence, between the ages of 10 and 20, and affects both sexes (2,3). The earliest cases of the disease are more severe. Loss of muscular strength limits both personal and occupational activities and could lead to the inability to walk in 20% of FSHD patients.

The FSHD has been described in 1884 by L. Landouzy and J. Dejerine (Comptes rendus de l'Académie des sciences, Paris, 1884, 98: 53-55). Since then, its molecular basis has been partially elucidated. More than 95% of the patients have a deletion in the subtelomeric region of the long arm of chromosome 4 (4q35 locus) (4). This region includes a repeated tandem sequence of 3.3 kb, named D4Z4. The number of D4Z4 repeats varies in the general population between 11 and 150, whereas it is between 1 and 10 in case of FSHD. The disease is transmitted in an autosomal dominant manner. However, 30% are sporadic cases resulting from de novo mutation.

There is still no treatment for this disorder that can halt or reverse the symptoms and muscle weakness. One ORF has been identified in the double homeobox (DUX4) present for each D4Z4 pattern (5). It encodes a transcription factor that is expressed in FSHD myoblasts. It has been shown recently that the FSHD patients carry specific nucleotide sequence creating a canonical DUX4 poly(A) signal, which stabilizes the D4Z4 transcripts and induces a toxic gain of function of the last DUX4 transcript (6). The expression of DUX4 mRNA is influenced by shortening of the telomere (7). DUX4 is currently believed to be the main candidate target for the FSHD therapy and is the main focus of research in FSHD (5,8). However, the molecular basis of FSHD and the exact mechanisms of this disease remain poorly understood.

Figure 1:
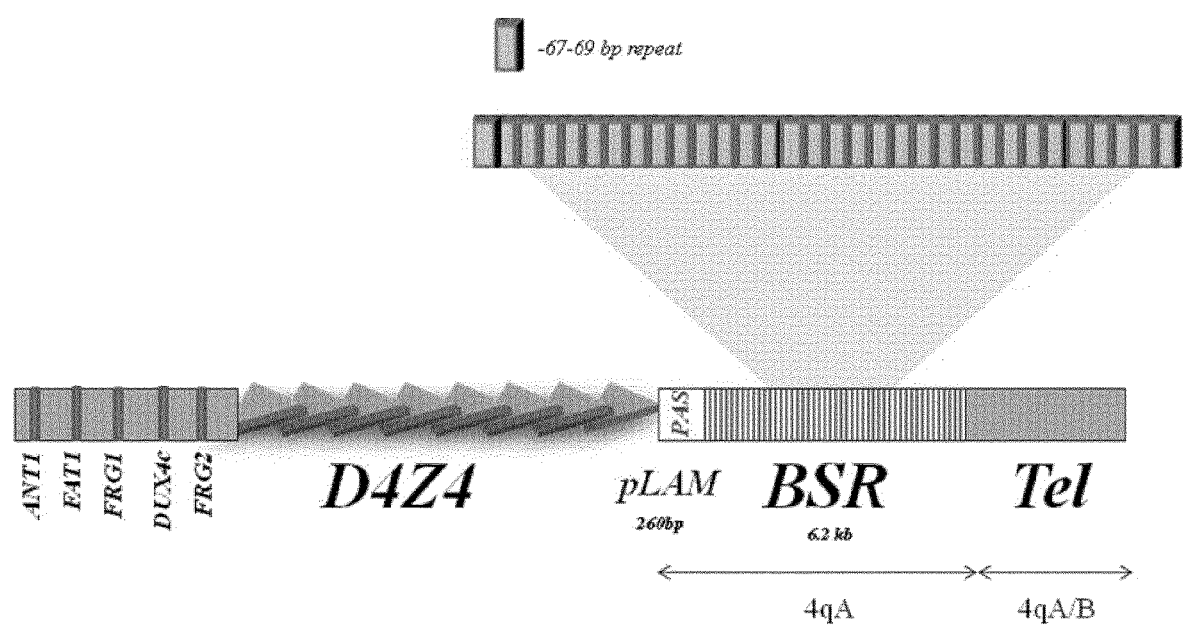

Other genes close to the D4Z4 region have been considered being responsible for observed pathology, such as FRG2, DUX4c, FRG1, FAT1 and ANT1/SLC25A4, all located in 4q35 locus (9,10) (FIG. 1). The function of FRG2 (FSH Region Gene 2) remains unknown. However, it has been shown that the induction of myoblast differentiation causes strong FRG2 overexpression (11). A truncated and inverted D4Z4, DUX4c, can inhibit myoblast differentiation (12). DUX4c protein upregulation has been reported in myoblasts of FSHD patients and in some FSHD biopsies (13). FRG1 (FSH Region Gene 1) is a highly conserved ubiquitous protein, possibly involved in RNA biogenesis and actin-binding (14). Transgenic mice overexpressing FRG1 strongly exhibit the muscle degeneration identical to human FSHD (15). FAT1 (Atypical cadherin 1) plays a role for cellular polarization, directed cell migration and cell-cell contact. FAT1-deficient mice developed an FSHD-like phenotype (16). The FAT1 defective splice variants were found in FSHD patients (a contraction-independent FSHD variant) (17). Finally, ANT1 (Adenine Nucleotide Translocator 1) is expressed primarily in the heart and muscles and encodes a carrier of ADP/ATP of mitochondrial inner membrane. Proteomics studies have shown an increase of the ANT1 expression in FSHD muscles, suggesting an early role of the protein in the development of the disease (9,10).

It has been also shown that epigenetic changes in the myoblasts of FSHD patients could play a crucial role in the FSHD development (6,18-21). The D4Z4 shortening correlates with hypomethylation of the D4Z4 repeat array and destabilizes the structure of chromatin that could lead to changes in the expression pattern of the neighbouring genes.

Another type(s) of FSHD, FSHD-like, or phenotypic FSHD, represents 5% of FSHD cases and is characterised by the high frequency of sporadic cases (70%) and the absence of macrosatellite contraction in 4q (22). This type of FSHD is associated with strong hypomethylation of the D4Z4 macrosatellites on chromosomes 4q and 10q (23,24) and could be related to the haploinsufficiency of SMCHD1 gene (24,25).

It has been shown that the canonical and phenotypic types of FSHD are associated with a permissive haplotype of the 4q subtelomere (6,22,25,26). It is an additional important condition, necessary for the FSHD manifestation, which consists of polymorphisms surrounding the D4Z4 tandem: a 4qA allele in 3' from D4Z4 (FIG. 1) is represented by (i) a pLAM sequence containing a polyadenylation sequence (PAS) of a most distal copy of DUX4 (27,28) and (ii) a beta-satellite repeat (BSR) tandem of 6.2 kb length (29), along with a 161 SNP in 5' from D4Z4 (6). Despite the recent findings demonstrating the heterogeneity of the 5' haplotype, the conservative presence of the 4qA allele in the 98,7% cases strongly supports the importance of 4qA in FSHD (30).

Although 4qA has been characterised structurally and the role of pLAM sequence has been determined, little is known about the functional role of its β-satellite repeats (BSR) part.

Previously, using 3C methodology, inventors demonstrated a transcriptional regulation activity of 4qA and its physical proximity to the promoters of the ANT1 and FRG1 genes in the nuclei of the muscles of FSHD patients (18). So far, there has been no other data concerning the 4qA-BSR function.

SUMMARY OF THE INVENTION

The present description discloses the existence and characterization of a key endogenous transcription factor, ZNF555, and provides novel therapeutic methods and compositions based on the modulation of this factor usable in human and veterinary medicine. The invention more particularly identifies ZNF555 as a new therapeutic target for the prevention or treatment of diseases associated with unwanted expression of ANT1, typically a musculoskeletal disease ("MSD") or a cancer. MSD encompasses in particular a myopathy such as Facioscapulohumeral Dystrophy (FSHD), muscular cachexia, etc.

An object of the invention relates to ZNF555, in particular to the ZNF555 protein encoded by a nucleic acid sequence selected from SEQ ID NO: 1, SEQ ID NO: 47 (NM_001172775.1), SEQ ID NO: 48 (NM_152791.4), SEQ ID NO: 49 (XM_011527714.1), SEQ ID NO: 50 (XM_011527715.1), SEQ ID NO: 51 (XM_011527716.1), and any (functional) variant thereof, typically by a sequence selected from SEQ ID NO: 1, SEQ ID NO: 47 and SEQ ID NO: 48 and any variant thereof, preferably by SEQ ID NO:1 or a variant thereof, for use as a therapeutic target, in particular in the context of the prevention or treatment of a musculoskeletal disease (typically FSHD) in a subject, for example for use as a therapeutic target for preventing or treating a musculoskeletal disease in a subject.

The invention also relates to the use of ZNF555, in particular of the ZNF555 protein encoded by a nucleic acid sequence selected from SEQ ID NO: 1, SEQ ID NO: 47 (NM_001172775.1), SEQ ID NO: 48 (NM_152791.4), SEQ ID NO: 49 (XM_011527714.1), SEQ ID NO: 50 (XM_011527715.1), SEQ ID NO: 51 (XM_011527716.1) and any (functional) variant thereof, typically by a sequence selected from SEQ ID NO: 1, SEQ ID NO: 47 and SEQ ID NO: 48 and any variant thereof, preferably by SEQ ID NO:1 or a variant thereof, as a therapeutic target, in particular in the context of the prevention or treatment of a musculoskeletal disease (typically FSHD) in a subject, for example as a therapeutic target for preventing or treating a musculoskeletal disease (typically FSHD) in a subject or for identifying a compound for use for preventing or treating a musculoskeletal disease (typically FSHD) in a subject.

A further object of the invention relates to a compound modulating, typically decreasing or inhibiting the expression or activity of ZNF555, typically a ZNF555 inhibitor, for use for modulating, typically decreasing or inhibiting, the expression or activity of ANT1 in a subject.

In a preferred embodiment, the invention comprises decreasing or inhibiting the expression or activity of ZNF555 in a subject, or exposing the subject to a ZNF555 inhibitor. Such embodiment is particularly suited to prevent or treat a subject at risk of, or who has been diagnosed with a musculoskeletal disease. In a particular embodiment, exposing the subject to an inhibitor comprises administering the inhibitor to the subject.

A further object of the invention relates to a compound that inhibits or decreases the expression or activity of ZNF555, in particular of a ZNF555 protein isoform encoded by SEQ ID NO: 1, SEQ ID NO: 47 (NM_001172775.1), SEQ ID NO: 48 (NM_152791.4), SEQ ID NO: 49 (XM_011527714.1), SEQ ID NO: 50 (XM_011527715.1), SEQ ID NO: 51 (XM_011527716.1) or any (functional) variant thereof, for use for preventing or treating a musculoskeletal disease in a subject.

Another object of the invention relates to the use of a compound that modulates the expression or activity of ZNF555 for the manufacture of a composition for modulating, typically decreasing or inhibiting, the expression or activity of ANT1 in a subject.

A further object of the invention relates to the use of a compound that inhibits or decreases the expression or activity of ZNF555 for the manufacture of a composition for preventing or treating a musculoskeletal disease in a subject.

A further object of the invention relates to a method for modulating, typically decreasing or inhibiting, the expression of ANT1 in a subject, comprising exposing the subject to a compound that modulates the expression or activity of ZNF555.

A further object of the invention relates to a method for preventing or treating a musculoskeletal disease in a subject, comprising exposing the subject to a compound that modulates the expression or activity of ZNF555.

Another object of the invention relates to the use of a compound that modulates the expression or activity of ZNF555 for use in a method for modulating, typically decreasing or inhibiting, the expression or activity of ANT1 in a subject.

A further object of the invention relates to the use of a compound that inhibits or decreases the expression or activity of ZNF555 for use in a method for preventing or treating a musculoskeletal disease in a subject.

In another aspect, the invention provides methods for identifying candidate therapeutic agents for use for preventing or treating a musculoskeletal disease, typically a MSD involving an unwanted expression of ANT1. Herein described is more particularly a method for identifying and selecting a compound inhibiting or decreasing the expression or activity of ZNF555, preferably of a ZNF555 protein encoded by a nucleic acid sequence selected from SEQ ID NO: 1, SEQ ID NO: 47 (NM_001172775.1), SEQ ID NO: 48 (NM_152791.4), SEQ ID NO: 49 (XM_011527714.1), SEQ ID NO: 50 (XM_011527715.1), SEQ ID NO: 51 (XM_011527716.1) and any (functional) variant thereof, typically selected from SEQ ID NO: 1, SEQ ID NO: 47 and SEQ ID NO: 48 and any variant thereof, and which is preferably SEQ ID NO:1 or a variant thereof, the method comprising a step of detecting and/or measuring the level of expression of ZNF555 or ANT1 in a muscle cell in the presence of a test compound, wherein an absent or decreased expression of ZNF555 or ANT1 in comparison with a control muscle cell that has not been exposed to or contacted with the test compound, is indicative of the capacity of said compound to inhibit or decrease the expression or activity of ZNF555 in said cell.

In another aspect, the invention relates to a pharmaceutical composition comprising a compound modulating, typically decreasing or inhibiting the expression or activity of ZNF555 and a pharmaceutically acceptable carrier or excipient.

In a further aspect, the present disclosure provides kits comprising (i) any one or more of the herein-described products and (ii) at least one container. Typically, the kit also comprises written instructions for using the kit, in particular the herein described product according to the disclosed methods.

DETAILED DESCRIPTION OF THE INVENTION

The present invention reveals the functional role of 4qA β-satellite repeats (BSR) in the muscular genetic disease FSHD. Inventors demonstrate that an individual β-satellite repeat (BSR) act as an active unit participating in the transcriptional regulation of 4q35 genes. Moreover, they show that the intrinsic sequence differences between BSR reveal a variable transcriptional activity and can interact with different protein partners. This has implications for understanding the differences in the severity of the disease. Inventors in particular demonstrate that the BSR 4qAe enhancer regulates the transcriptional activity of the Adenine Nucleotide Translocator 1 gene (ANT1) promoter.

ANT1 is implicated in the muscle function protecting the cells from apoptosis (31,32), involved in red-ox system stability (33) and related to a hypersensitivity to oxidative stress of FSHD muscles (34). The present invention discloses the key endogenous factor responsible at the molecular level for the mechanism of BSR action and, more generally, for the abnormal expression ANT1 in various pathophysiological conditions. ZNF555, a trans-acting protein has been indeed shown by inventors to interact with the 4qAe enhancer. They investigated the expression level of ZNF555 and found that it was highly expressed in myogenic cells. They further discovered that depletion of ZNF555 strongly impacts the ANT1 gene transcription myoblasts, in particular in FSHD myoblasts. ZNF555 interaction with the ANT1 gene promoter was demonstrated by ChIP.

The results disclosed in this application show that inhibition of ZNF555 was able to correct the abnormal ANT1 expression at least partly responsible for the musculoskeletal disease subjects and can thus be used to prevent or treat musculoskeletal diseases in a subject in need thereof.

More particularly, the invention provides a method for decreasing or inhibiting ANT1 expression in a subject in need thereof, comprising modulating ZNF555 expression or activity in said subject.

Definitions

As used herein, "treatment" or "treat" refers to clinical intervention in an attempt to alter the natural course of the individual being treated, and can be performed either for preventive (prophylactic) or curative purpose. Desirable effects of treatment include, but are not limited to, preventing occurrence or recurrence of disease, alleviation of symptoms, diminishment of any direct or indirect pathological consequences of the disease, decreasing the rate of disease progression, amelioration or palliation of the disease state, and remission or improved prognosis. In some embodiments, compositions and methods of the invention are used to delay development of a musculoskeletal disease or disorder or to slow the progression of a musculoskeletal disease or disorder.

The treatment is intended for a subject. "Subject" refers to an animal, typically a mammal. Examples of mammals include humans and non-human animals such as, without limitation, domesticated animals (e.g., cows, sheep, cats, dogs, and horses), non-human primates (such as monkeys), rabbits, and rodents (e.g., mice and rats). The treatment is preferably intended for a human being in need thereof. Are considered as such, the subjects suffering from a disease, disorder or dysfunctional state leading to the overexpression of ANT1 in muscle cells, or those considered "at risk of developing" such a disease, disorder or dysfunctional state, in which this has to be prevented. A specific example of such a disease is a musculoskeletal disease or disorder such as the Facioscapulohumeral Dystrophy (FSHD).

A "therapeutically affective amount" of a product is an amount of the product allowing the treatment, as previously defined, of a subject. It is typically an amount that is effective to inhibit ZNF555 in the treated subject.

The term "isolated", as used herein, refers to molecules (e.g., nucleic or amino acid) that are removed from a component of their natural environment, isolated or separated, and are at least 60% free, preferably 75% free, and most preferably 90% free from other components with which they are naturally associated. An "isolated" polypeptide (or protein) is for instance a polypeptide separated from a component of its natural environment and, preferably purified to greater than 90% or 95% purity as determined by, for example, electrophoretic (e.g., SDS-PAGE, isoelectric focusing (IEF), capillary electrophoresis) or chromatographic (e.g., ion exchange or reverse phase HPLC) migration. An "isolated" nucleic acid refers to a nucleic acid molecule separated from a component of its natural environment and/or assembled in a different construct (e.g., a vector, expression cassette, recombinant host, etc.).

The term "sequence identity" as applied to nucleic acid or protein sequences, refers to the quantification (usually percentage) of nucleotide or amino acid residue matches between at least two sequences aligned using a standardized algorithm such as Smith-Waterman alignment (Smith and Waterman (1981) J Mol Biol 147:195-197), CLUSTALW (Thompson et al. (1994) Nucleic Acids Res 22:4673-4680), or BLAST2 (Altschul et al. (1997) Nucleic Acids Res 25:3389-3402). BLAST2 may be used in a standardized and reproducible way to insert gaps in one of the sequences in order to optimize alignment and to achieve a more meaningful comparison between them.

Within the context of the present invention, the term "ZNF555" (zinc finger protein 555) or "ZNF555 protein" designates any native ZNF555 protein from any vertebrate source, including mammals such as primates (e.g. humans) and rodents (e.g., mice and rats), unless otherwise indicated. The term encompasses "full-length," unprocessed ZNF555, as well as any form of ZNF555 that results from processing inside or outside a cell. The term also encompasses isoforms, naturally-occurring variants of ZNF555, e.g., splice variants or allelic variants.

The terms "ZNF555 isoform" designate three distinct isoforms of human ZNF555.

SEQ ID NO: 2 is the amino acid sequence of an exemplary human ZNF555 isoform (herein identified as "isoform 1" or "ZNF555 isoform 1"). ZNF555 isoform 1 contains 15 Zinc fingers (Position: 172-194, 200-222, 228-250, 256-278, 284-306, 312-334, 340-362, 368-390, 396-418, 424-446, 452-474, 480-502, 508-530, 536-558 and 564-586, length: 23AA) and a KRAB domain (Position:4-77; length: 74AA). SEQ ID NO: 2 is also identified in the art as Q8NEP9-1 (UniProt reference).

SEQ ID NO: 3 is the amino acid sequence of a second exemplary human ZNF555 isoform (herein identified as "isoform 2" or "ZNF555 isoform 2"). ZNF555 isoform 2 contains 11 Zinc fingers (Positions: 185-208, 213-236, 241-266, 270-294, 298-322, 325-350, 353-378, 381-406, 409-433, 437-461 and 469-490) and a KRAB domain (Position: 4-77). SEQ ID NO: 3 is also identified in the art as Q8NEP9-2 (UniProt reference).

SEQ ID NO: 4 is the amino acid sequence of a third exemplary human ZNF555 isoform (herein identified as "isoform 3" or "ZNF555 isoform 3"). ZNF555 isoform 3 contains X Zinc fingers (Positions: 171-193, 199-221, 227-

249, 255-277, 283-305, 311-333, 339-361, 367-389, 395-417, 423-445, 451-473, 479-501, 507-529, 535-557 and 563-585, length: 23AA) and a KRAB domain (Position: 4-77; length: 74AA). SEQ ID NO: 4 is also identified in the art as Q8NEP9-4 (UniProt reference).

ZNF555 has the ability to interact with the 4qAe enhancer and to activate or stimulate ex vivo or in vivo ANT1 transcription/expression in muscle cells, typically myoblasts. A preferred isoform for use in the context of the invention is ZNF555 isoform "2" as it exhibits the best ability to interact with the 4qAe enhancer and to activate or stimulate ex vivo or in vivo ANT1 transcription/expression in muscle cells, in particular myoblasts of a subject suffering of a musculoskeletal disease or disorder such as FSHD ("FSHD myoblasts") where ANT1 is abnormally overexpressed.

Variants, in particular naturally-occurring variants, include any protein comprising the sequence of SEQ ID NO: 3, or the sequence of amino acid residues 107, 137, 194, 304 and 515 of SEQ ID NO: 3, with one or more amino acid substitution (typically: Position 107, N to D; Position 137, P to L; Position 194: H to N, Position 304: I to T, and Position 515: K to T), addition and/or deletion of one or several (typically 1, 2 or 3) amino acid residues, preferably not more than 10 distinct amino acid substitution(s), addition(s), and/or deletion(s) of one or several (typically 1, 2 or 3) amino acid residues. Typical naturally-occurring variants retain a biological activity of SEQ ID NO: 3, typically the ability to interact with the 4qAe enhancer.

In a particular embodiment, the term ZNF555 designates a human protein, particularly a protein comprising or having SEQ ID NO: 3 or a naturally-occurring variant thereof. In a preferred embodiment, the term ZNF555 designates isoform "2".

ZNF555 according to the present description may be isolated, purified, and/or recombinant.

In certain embodiments, the invention may use, instead or in addition to a ZNF555 protein, a nucleic acid encoding ZNF555. "Nucleic acid encoding ZNF555" may be DNA or RNA, single- or double-stranded, as well as included in a vector or present at one or more locations in a host cell.

A typical deoxyribonucleic acid (DNA) sequence encoding ZNF555 is SEQ ID NO: 1.

A typical ribonucleic acid sequence (RNA) encoding ZNF555 can be encoded by a cDNA sequence selected from SEQ ID NO: 47 (NM_001172775.1), SEQ ID NO: 48 (NM_152791.4), SEQ ID NO: 49 (XM_011527714.1), SEQ ID NO: 50 (XM_011527715.1) and SEQ ID NO: 51 (XM_011527716.1), preferably by SEQ ID NO: 47, SEQ ID NO: 48 or a variant thereof.

Alternative nucleic acid molecules encoding a ZNF555 include any variant of anyone of the herein identified nucleic acid sequences, for example of SEQ ID NO:1, resulting from the degeneracy of the genetic code, as well as any sequence which hybridizes to said sequence (for example SEQ ID NO: 1) under stringent conditions, more preferably having at least 80%, 85%, 90%, 95% or more sequence identity to said sequence (for example SEQ ID NO; 1), and encoding a functional ZNF555.

"Nucleic acid encoding an anti-ZNF555 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

ZNF555 Production

ZNF555 can be produced by any conventionally known protein expression method and purification method. For example: (i) a method for synthesizing peptides; (ii) a method for purifying and isolating them from a living body or cultured cells; or (iii) a method for producing them with the use of genetic recombination techniques; and combinations thereof and the like (for example, the standard techniques described for example in Molecular Cloning (Sambrook, J., Fritsch, E. F., Maniatis, T., Cold Spring Harbor Laboratory Press) (1989) and Current Protocols in Molecular Biology (Ausubel, F. M., John Wiley and Sons, Inc. (1989)).

In a particular embodiment, the invention relates to a method for producing ZNF555 by expression of a coding nucleic acid in a host cell, and collection or purification of ZNF555. In this regard, the invention also described recombinant host cells comprising a nucleic acid encoding a ZNF555. Such cells may be prokaryotic (such as bacteria) or eukaryotic (such as yeast cells, insect cells, plant cells or mammalian cells). The nucleic acid may be placed under the control of any suitable regulatory sequence, such as a promoter, terminator, and the like. Alternatively, the nucleic acid may be inserted in the host cell in a location where expression is driven by an endogenous promoter. Techniques for inserting nucleic acids in cells are well known in the art.

ZNF555 Inhibition

The invention provides novel methods which comprise an inhibition of ZNF555 expression (e.g. ZNF555 mRNA or protein amount) or activity in a subject in need thereof. The term "inhibition" designates any decrease of the expression (e.g., amount or level) or activity of ZNF555 in a subject. A decrease more preferably designates a change by at least 10%, 20%, 30%, 40%, 50%, 60%, 70%, 80% or more as compared to non-decreased situation. As a result, inhibiting ZNF555 designates reducing by at least 10%, 20%, 30%, 40%, 50%, 60%, 70%, 80% or more ZNF555 expression or activity, as well as completely blocking or suppressing ZNF555 expression or activity. Depending on the situation, the inhibition may be transient, sustained or permanent. Also inhibiting the activity includes decreasing the amount of ZNF555 in the subject, particularly in muscle cells, diminishing the potency of the protein (for instance by modulating the level of co-factors or substrate in the subject), and decreasing the level or activity of degradation products produced by ZNF555.

ZNF555 expression can be easily measured by the skilled person of the art thanks to well-known techniques. ZNF555 mRNA expression can typically be measured by reverse Transcription Polymerase Chain Reaction (RT-qPCR) or by any equivalent method and ZNF555 protein expression can typically be measured by Western Blot or Mass-Spectroscopy.

ZNF555 activity can be detected and measured in vivo using for example ANT1 as a downstream target. ZNF555 activity can thus typically be detected and measured in vivo by a method including a step of measuring ANT1 mRNA or protein expression level (using anyone of the herein above identified well-known methods). The ZNF555 transcriptional activity (production of mRNA transcripts) can also be detected in vitro thanks to conventional methods well known by the skilled person, such as a luciferase assay (cf. experimental part).

In a particular embodiment, the invention provides products, compositions and methods for inhibiting ZNF555 in a subject. ZNF555inhibition may be obtained by the use of ZNF555 inhibitors, i.e., any compound that inhibit the expression or activity of ZNF555. ZNF555 inhibitors include expression inhibitors, antagonists, sequestrators, or target masking compounds. Preferred types of ZNF555 inhibitors include ZNF555 ligands (covalent or non-covalent), anti-ZNF555 antibodies (and fragments and derivatives thereof), nucleic acids encoding anti-ZNF555 antibodies (or fragments and derivatives thereof), inhibitory nucleic acids [antisense nucleic acids, short interfering RNAs (siRNAs or esiRNAs), small hairpin RNAs (shRNA), microRNAs, aptamers, or ribozymes], peptides, or small drugs, or combination(s) thereof. Alternatively, or in addition, ZNF555 inhibition can be obtained by vaccinating a subject against a ZNF555 antigen, so that antibodies are produced by the subject in need of ZNF555 inhibition.

ZNF555 Inhibitors

Specific examples of ZNF555 inhibitors are selected from ADAM12 (A Disintegrin And Metalloproteinase Domain 12), FGF20 (Fibroblast Growth Factor 20), ZNF484 (Zinc Finger Protein 484), ZNF550 (Zinc Finger Protein 550), ZNF585A (Zinc Finger Protein 585A), FAM149B1 (Family with sequence similarity 149, member B1), LRRC17 (Leucine Rich Repeat Containing 17), PLBD2 (Phospholipase B Domain Containing 2), SVOPL (Synaptic Vesicle 2 Related Protein Homolog-Like), TAF13 (TATA Box Binding Protein-Associated Factor), TTC9C (Tetratricopeptide Repeat Domain 9C), C2orf74 (Chromosome 2 Open Reading Frame 74), ZNF420 (Zinc Finger Protein 420), ZNF432 (Zinc Finger Protein 432), ZNF285 (Zinc Finger Protein 285), FAM170B (Family With Sequence Similarity 170, Member B), FNTA (Farnesyltransferase, CAAX Box, Alpha), ZNF670 (Zinc Finger Protein 670), ZNF790 (Zinc Finger Protein 790), ZNF793 (Zinc Finger Protein 793), ZNF879 (Zinc Finger Protein 879), and a fragment thereof. A preferred inhibitor is ADAM12.

Antibodies Against ZNF555

Specific examples of ZNF555 inhibitors are antibodies that specifically bind to ZNF555.

Antibodies can be synthetic, monoclonal, or polyclonal and can be made by techniques well known in the art. Such antibodies specifically bind via the antigen-binding sites of the antibody (as opposed to non-specific binding). ZNF555 polypeptides, fragments, variants, fusion proteins, etc., can be employed as immunogens in producing antibodies immunoreactive therewith. More specifically, the polypeptides, fragments, variants, fusion proteins, etc. contain antigenic determinants or epitopes that elicit the formation of antibodies.

These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon protein folding (C. A. Janeway, Jr. and P. Travers, Immuno Biology 3:9 (Garland Publishing Inc., 2nd ed. 1996)). Because folded proteins have complex surfaces, the number of epitopes available is quite numerous; however, due to the confoniiation of the protein and steric hindrances, the number of antibodies that actually bind to the epitopes is less than the number of available epitopes (C. A. Janeway, Jr. and P. Travers, Immuno Biology 2:14 (Garland Publishing Inc., 2nd ed. 1996)). Epitopes can be identified by any of the methods known in the art. Both polyclonal and monoclonal antibodies can be prepared by conventional techniques.

Preferred antibodies of the invention are directed to a ZNF555 epitope and/or have been generated by immunization with a polypeptide comprising a ZNF555 epitope selected from: the mature ZNF555 protein, a fragment of ZNF555 comprising at least 8 consecutive amino acid residues of SEQ ID NO: 3 (or the corresponding residues of a natural variant of SEQ ID NO: 3). Preferred antibodies of the invention bind an epitope of the Zn finger domain, typically an epitope comprised between amino acid residues 576-625 of SEQ ID NO: 3 or the corresponding residues of a natural variant of SEQ ID NO: 3.

The term "antibodies" is meant to include polyclonal antibodies, monoclonal antibodies, fragments thereof, such as F(ab')2 and Fab fragments, single-chain variable fragments (scFvs), single-domain antibody fragments (VHHs or Nanobodies), bivalent antibody fragments (diabodies), as well as any recombinantly and synthetically produced binding partners, human antibodies or humanized antibodies.

ZNF555 Antibodies are defined to be specifically binding preferably if they bind to ZNF555 with a Ka of greater than or equal to about $10^7$ M-1. Affinities of antibodies can be readily determined using conventional techniques, for example those described by Scatchard et al., Ann. N.Y. Acad. Sci., 51:660 (1949).

Polyclonal antibodies can be readily generated from a variety of sources, for example, horses, cows, donkeys, goats, sheep, dogs, chickens, rabbits, mice, or rats, using procedures that are well known in the art. In general, purified ZNF555 or a peptide based on the amino acid sequence of ZNF555 that is appropriately conjugated is administered to the host animal typically through parenteral injection. The immunogenicity of ZNF555 can be enhanced through the use of an adjuvant, for example, Freund's complete or incomplete adjuvant. Following booster immunizations, small samples of serum are collected and tested for reactivity to ZNF555 polypeptide. Examples of various assays useful for such determination include those described in Antibodies: A Laboratory Manual, Harlow and Lane (eds.), Cold Spring Harbor Laboratory Press, 1988; as well as procedures, such as countercurrent immuno-electrophoresis (CIEP), radioimmunoassay, radio-immunoprecipitation, enzyme-linked immunosorbent assays (ELISA), dot blot assays, and sandwich assays. See U.S. Pat. Nos. 4,376,110 and 4,486,530.

Monoclonal antibodies can be readily prepared using well known procedures. See, for example, the procedures described in U.S. Pat. Nos. RE 32,011, 4,902,614, 4,543, 439, and 4,411,993; Monoclonal Antibodies, Hybridomas: A New Dimension in Biological Analyses, Plenum Press, Kennett, McKcam, and Bechtol (eds.), 1980.

For example, the host animals, such as mice, can be injected intraperitoneally at least once and preferably at least twice at about 3 week intervals with isolated and purified wild-type or mutant ZNF555 protein or conjugated ZNF555 peptide, optionally in the presence of adjuvant. Mouse sera are then assayed by conventional dot blot technique or antibody capture (ABC) to determine which animal is best to fuse. Approximately two to three weeks later, the mice are given an intravenous boost of protein or peptide. Mice are later sacrificed and spleen cells fused with commercially available myeloma cells, such as Ag8.653 (ATCC), following established protocols. Briefly, the myeloma cells are washed several times in media and fused to mouse spleen cells at a ratio of about three spleen cells to one myeloma cell. The fusing agent can be any suitable agent used in the art, for example, polyethylene glycol (PEG). Fusion is plated out into plates containing media that allows for the selective growth of the fused cells. The fused cells can then be allowed to grow for approximately eight days. Supernatants from resultant hybridomas are collected and added to a plate that is first coated with goat anti-mouse Ig. Following washes, a label, such as a labeled ZNF555 polypeptide, is added to each well followed by incubation. Positive wells can be subsequently detected. Positive clones can be grown in bulk culture and supernatants are subsequently purified over a Protein A column (Pharmacia).

The monoclonal antibodies of the disclosure can be produced using alternative techniques, such as those described by Alting-Mees et al., "Monoclonal Antibody Expression Libraries: A Rapid Alternative to Hybridomas", Strategies in Molecular Biology 3:1-9 (1990), which is incorporated herein by reference. Similarly, binding partners can be constructed using recombinant DNA techniques to incorporate the variable regions of a gene that encodes a specific binding antibody. Such a technique is described in Larrick et al., Biotechnology, 7:394 (1989).

Antigen-binding fragments of such antibodies, which can be produced by conventional techniques, are also encompassed by the present invention. Examples of such fragments include, but are not limited to, Fab and F(ab')2 fragments. Antibody fragments and derivatives produced by genetic engineering techniques are also provided.

The monoclonal antibodies of the present disclosure include chimeric antibodies, e.g., humanized versions of murine monoclonal antibodies. Such humanized antibodies can be prepared by known techniques, and offer the advantage of reduced immunogenicity when the antibodies are administered to humans. In one embodiment, a humanized monoclonal antibody comprises the variable region of a murine antibody (or just the antigen binding site thereof) and a constant region derived from a human antibody. Alternatively, a humanized antibody fragment can comprise the antigen binding site of a murine monoclonal antibody and a variable region fragment (lacking the antigen-binding site) derived from a human antibody. Procedures for the production of chimeric and further engineered monoclonal antibodies include those described in Riechmann et al. (Nature 332:323, 1988), Liu et al. (PNAS 84:3439, 1987), Larrick et al. (Bio/Technology 7:934, 1989), and Winter and Harris (TIPS 14:139, May, 1993). Procedures to generate antibodies transgenically can be found in GB 2,272,440, U.S. Pat. Nos. 5,569,825 and 5,545,806.

Antibodies produced by genetic engineering methods, such as chimeric and humanized monoclonal antibodies, comprising both human and non-human portions, which can be made using standard recombinant DNA techniques, can be used. Such chimeric and humanized monoclonal antibodies can be produced by genetic engineering using standard DNA techniques known in the art, for example using methods described in Robinson et al. International Publication No. WO 87/02671; Akira, et al. European Patent Application 0184187; Taniguchi, M., European Patent Application 0171496; Morrison et al. European Patent Application 0173494; Neuberger et al. PCT International Publication No. WO 86/01533; Cabilly et al. U.S. Pat. No. 4,816,567; Cabilly et al. European Patent Application 0125023; Better et al., Science 240:1041 1043, 1988; Liu et al., PNAS 84:3439 3443, 1987; Liu et al., J. Immunol 139:3521 3526, 1987; Sun et al. PNAS 84:214 218, 1987; Nishimura et al., Canc. Res. 47:999 1005, 1987; Wood et al., Nature 314:446 449, 1985; and Shaw et al., J. Natl. Cancer Inst. 80:1553 1559, 1988); Morrison, S. L., Science 229: 1202 1207, 1985; Oi et al., BioTechniques 4:214, 1986; Winter U.S. Pat. No. 5,225,539; Jones et al., Nature 321:552 525, 1986; Verhoeyan et al., Science 239:1534, 1988; and Beidler et al., J. Immunol 141:4053 4060, 1988.

In connection with synthetic and semi-synthetic antibodies, such terms are intended to cover but are not limited to antibody fragments, isotype switched antibodies, humanized antibodies (e.g., mouse-human, human-mouse), hybrids, antibodies having plural specificities, and fully synthetic antibody-like molecules.

For therapeutic applications, "human" monoclonal antibodies having human constant and variable regions are often preferred so as to minimize the immune response of a patient against the antibody. Such antibodies can be generated by immunizing transgenic animals which contain human immunoglobulin genes. See Jakobovits et al. Ann NY Acad Sci 764:525-535 (1995).

Human monoclonal antibodies against ZNF555 polypeptides can also be prepared by constructing a combinatorial immunoglobulin library, such as a Fab phage display library or a scFv phage display library, using immunoglobulin light chain and heavy chain cDNAs prepared from mRNA derived from lymphocytes of a subject. See, e.g., McCafferty et al. PCT publication WO 92/01047; Marks et al. (1991) J. Mol. Biol. 222:581 597; and Griffths et al. (1993) EMBO J 12:725 734. In addition, a combinatorial library of antibody variable regions can be generated by mutating a known human antibody. For example, a variable region of a human antibody known to bind ZNF555, can be mutated by, for example, using randomly altered mutagenized oligonucleotides, to generate a library of mutated variable regions which can then be screened to bind to ZNF555. Methods of inducing random mutagenesis within the CDR regions of immunoglobin heavy and/or light chains, methods of crossing randomized heavy and light chains to form pairings and screening methods can be found in, for example, Barbas et al. PCT publication WO 96/07754; Barbas et al. (1992) Proc. Nat'l Acad. Sci. USA 89:4457 4461.

An immunoglobulin library can be expressed by a population of display packages, preferably derived from filamentous phage, to form an antibody display library. Examples of methods and reagents particularly amenable for use in generating antibody display library can be found in, for example, Ladner et al. U.S. Pat. No. 5,223,409; Kang et al. PCT publication WO 92/18619; Dower et al. PCT publication WO 91/17271; Winter et al. PCT publication WO 92/20791; Markland et al. PCT publication WO 92/15679; Breitling et al. PCT publication WO 93/01288; McCafferty et al. PCT publication WO 92/01047; Garrard et al. PCT publication WO 92/09690; Ladner et al. PCT publication WO 90/02809; Fuchs et al. (1991) Bio/Technology 9:1370 1372; Hay et al. (1992) Hum Antibod Hybridomas 3:81 85; Huse et al. (1989) Science 246:1275 1281; Griffths et al. (1993) supra; Hawkins et al. (1992) J Mol Biol 226:889 896; Clackson et al. (1991) Nature 352:624 628; Gram et al. (1992) PNAS 89:3576 3580; Garrad et al. (1991) Bio/Technology 9:1373 1377; Hoogenboom et al. (1991) Nuc Acid Res 19:4133 4137; and Barbas et al. (1991) PNAS 88:7978 7982. Once displayed on the surface of a display package (e.g., filamentous phage), the antibody library is screened to identify and isolate packages that express an antibody that binds a ZNF555polypeptide. In a preferred embodiment, the primary screening of the library involves panning with an immobilized ZNF555 polypeptide and display packages expressing antibodies that bind immobilized ZNF555 polypeptide are selected.

In a particular embodiment, the invention relates to a composition comprising an anti-ZNF555 antibody (or a fragment or derivative thereof) and a pharmaceutically acceptable excipient.

A preferred polyclonal antibody usable in the context of the present invention binds each isoform of ZNF555. An example thereof is anti-ZNF555 (AB4, Sigma Aldrich).

Another preferred polyclonal antibody usable in the context of the present invention binds

SEQ ID NO: 21 (SSSLRRHVRIHTTEKQYKCNVGHP-PANEFMCSASEKSHQERDLIKVVNMV).

In an alternative embodiment, the invention relates to and uses a composition comprising a nucleic acid encoding an anti-ZNF555 antibody (or a fragment or derivative thereof) and a pharmaceutically acceptable excipient.

Inhibitory Nucleic Acids

In an alternative embodiment, the ZNF555 inhibitor is an inhibitory nucleic acid, i.e., any nucleic acid molecule which inhibits ZNF555 gene or protein expression. Preferred inhibitory nucleic acids include antisense nucleic acids, short interfering RNAs (siRNAs, such as endonuclease prepared siRNAs or esiRNAs), small hairpin RNAs (shRNA), microRNAs, aptamers, or ribozymes. In a particular embodiment, the inhibitory nucleic acid is a small interfering RNA that prevents translation of ZNF555 mRNA. In another particular embodiment, the inhibitory nucleic acid is an antisense oligonucleotide that prevents translation of ZNF555 mRNA. In another particular embodiment, the inhibitory nucleic acid is a small hairpin RNA that prevents translation of ZNF555 mRNA.

siRNA comprise a sense nucleic acid sequence and an anti-sense nucleic acid sequence of the polynucleotide of interest. siRNA are constructed such that a single transcript (double stranded RNA) have both the sense and complementary antisense sequences from the target gene. The nucleotide sequence of siRNAs may be designed using an siRNA design computer program available from, for example, the Ambion website on the world wide web.

In some embodiments, the length of the antisense oligonucleotide or siRNAs is less than or equal to 10 nucleotides. In some embodiments, the length of the antisense oligonucleotides and siRNAs is as long as the naturally occurring transcript. In some embodiments, the antisense oligonucleotides and siRNAs have 18-30 nucleotides. In some embodiments, the antisense oligonucleotides and siRNAs are less than 25 nucleotides in length.

Preferred inhibitory nucleic acid molecules comprise a domain having a nucleotide sequence that is perfectly complementary to a region of a ZNF555 gene or RNA. Such a domain contains typically from 25 to 404 nucleotides, for example 29 nucleotides, allowing specific hybridization and optimal inhibition the gene transcription or RNA translation. The sequence of the inhibitory nucleic acids may be derived directly from the sequence of a gene encoding ZNF555, such as SEQ ID NO: 1 (Position: 1410-1813). Alternatively, or in addition, inhibitory nucleic acids may hybridize to a regulatory element in a ZNF555 gene or nucleic acid sequence [typically a cDNA selected from SEQ ID NO: 47 (NM_001172775.1), SEQ ID NO: 48 (NM_152791.4), SEQ ID NO: 49 (XM_011527714.1), SEQ ID NO: 50 (XM_011527715.1) and SEQ ID NO: 51 (XM_011527716.1)] or RNA, such as a promoter, a splicing site, etc., and prevent effective regulation thereof.

Specific examples of inhibitory nucleic acid molecules of the present invention include isolated single strand nucleic acid molecules consisting of from 25 to 29 consecutive nucleotides of SEQ ID NO: 1. Specific examples of inhibitory nucleic acid molecules of the invention are antisense nucleic acids consisting in anyone of the following nucleotide sequence or the perfectly complementary strand thereof:

SEQ ID NO: 5:
TGTGAGAATGCACCCTGAAGACAAA

SEQ ID NO: 6:
TCCTATGAATGCAAGCTATGTGGGA

SEQ ID NO: 7:
AAGCTTTCTATTGCCACATATCCTT

SEQ ID NO: 8:
ACAAAAACATATGAGAAGACATACC

SEQ ID NO: 9:
GCAGAGAAACTCTATAAATGCAAGC

SEQ ID NO: 10:
AGTGTGGGAAAGCTTTCAGTTGGCC

SEQ ID NO: 11:
TGAACTTTTGCAACAACATGTGAGA

SEQ ID NO: 12:
ACGCACACTGTAGAGAAGCCCTATG

SEQ ID NO: 13:
AATGTAAGGAATGTGGGAAGGTCTT

SEQ ID NO: 14:
CAAATGGCCATCATCTTTACCAATA

SEQ ID NO: 15:
CATATGAGACTGCACACTGGAGAGA

SEQ ID NO: 16:
AACCTTATCAATGTAAGCATTGTGG

SEQ ID NO: 17:
GAAAGCATTCAATTGTTCCTCATCC

SEQ ID NO: 18:
TTAAGGCGACATGTGAGAATACACA

SEQ ID NO: 19:
CTACAGAAAAACAGTATAAGTGTAA

SEQ ID NO: 20:
TGTAGGACATCCTCCTGCAAATGAATTCA

Other specific examples of inhibitory nucleic acid molecules of the invention are small or short hairpin RNAs (shRNAs) consisting in anyone of the following nucleotide sequence:

SEQ ID NO: 44:
CCTTCAGTTATTCTTCGGCTT

SEQ ID NO: 45:
CCTGAAGACAAATCCTATGAA

SEQ ID NO: 46:
CCATCATCTTTACCAATACAT

Peptide and Small Drugs

In an alternative embodiment, the ZNF555 inhibitor is a peptide or small drug that inhibits the activity of ZNF555. The peptide or small drug is typically a molecule that selectively binds ZNF555, or a substrate of ZNF555, or a co-factor of ZNF555, or a degradation product or metabolite of ZNF555 pathway.

Peptides preferably contain from 3 to 20 amino acid residues, and their sequence may be identical to a domain of ZNF555 (bait peptide) or to a domain of a ZNF555 substrate, co-factor, degradation product or metabolite. Preferred peptides of the invention contain from 4 to 30 consecutive amino acid residues of SEQ ID NO: 3 (or of a corresponding sequence of a natural variant of SEQ ID NO:

3). Most preferred peptides of the invention comprise from 5 to 25 consecutive amino acid residues of SEQ ID NO: 3 (or of a corresponding sequence of a natural variant of SEQ ID NO: 3).

The peptides of the invention can comprise peptide, non-peptide and/or modified peptide bonds. In a particular embodiment, the peptides comprise at least one peptidomimetic bond selected from intercalation of a methylene ($-CH_2-$) or phosphate ($-PO_2-$) group, secondary amine ($-NH-$) or oxygen ($-O-$), alpha-azapeptides, alpha-alkylpeptides, N-alkylpeptides, phosphonamidates, depsipeptides, hydroxymethylenes, hydroxyethylenes, dihydroxyethylenes, hydroxyethylamines, retro-inverso peptides, methyleneoxy, cetomethylene, esters, phosphinates, phosphinics, or phosphonamides. Also, the peptides may comprise a protected N-ter and/or C-ter function, for example, by acylation, and/or amidation and/or esterification.

The peptides of the invention may be produced by techniques known per se in the art such as chemical, biological, and/or genetic synthesis.

Each of these peptides, in isolated form, represents a particular object of the present invention.

Preferred small drugs are hydrocarbon compounds that selectively bind ZNF555.

Small drugs and peptides are preferably obtainable by a method comprising: (i) contacting a test compound with ZNF555 or a fragment thereof, (ii) selecting a test compound which binds ZNF555 or said fragment thereof, and (iii) selecting a compound of (ii) which inhibits an activity of ZNF555.

Such a method represents a particular object of the invention.

Small drugs and peptides are also obtainable by a method comprising: (i) contacting a test compound with a ZNF555 substrate, co-factor, or degradation product, or a fragment thereof, (ii) selecting a test compound which binds to said ZNF555 substrate, co-factor, or degradation product, or a fragment thereof, and (iii) selecting a compound of (ii) which inhibits an activity of ZNF555. Such a method represents a particular object of the invention.

Vaccination

In an alternative (or cumulative) embodiment, inhibition of ZNF555 in a subject is obtained by vaccinating (or immunizing) the subject with a ZNF555 antigen. As a result of such a vaccination or immunization, the subject produces antibodies (or cells) which inhibit ZNF555. In particular, injection(s) of a ZNF555 antigen (e.g., an immunogenic ZNF555 essentially devoid of biological activity) can generate antibodies in the treated subject. These antibodies will protect against an excess of ZNF555 expression and can be used along as immunotherapy or a vaccination.

An object of the invention thus resides in a method of vaccinating a subject comprising administering to the subject a ZNF555 antigen.

A further object of the invention relates to a ZNF555 antigen for use to vaccinate a subject in need thereof.

In a particular embodiment, the ZNF555 antigen used for vaccination is an inactivated immunogenic molecule that induces an immune response against ZNF555 in a subject. Inactivation may be obtained e.g., by chemically or physically altering ZNF555 or by mutating or truncating the protein, or both; and immunogenicity may be obtained as a result of the inactivation and/or by further conjugating the protein to a suitable carrier or hapten, such as KLH, HSA, polylysine, a viral anatoxin, or the like, and/or by polymerization, or the like. The antigen may thus be chemically or physically modified, e.g., to improve its immunogenicity.

In a preferred embodiment, the ZNF555 antigen of the invention comprises ZNF555 or an epitope-containing fragment or mimotope thereof.

In a particular embodiment, the ZNF555 antigen comprises a full length ZNF555 protein. In a further particular embodiment, the ZNF555 antigen comprises a protein comprising SEQ ID NO: 3, or a sequence having at least 90% identity to SEQ ID NO: 3.

In an alternative embodiment, the ZNF555 antigen comprises a fragment of a ZNF555 protein comprising at least 6 consecutive amino acid residues and containing an immunogenic epitope, or a mimotope thereof. In a preferred embodiment, the ZNF555 antigen comprises at least from 6 to 20 amino acid residues. Preferred peptides of the invention contain from 4 to 30 consecutive amino acid residues of SEQ ID NO: 3 (or of a corresponding sequence of a natural variant of SEQ ID NO: 3). Most preferred peptides of the invention comprise from 5 to 25 consecutive amino acid residues of SEQ ID NO: 3 (or of a corresponding sequence of a natural variant of SEQ ID NO: 3).

The ZNF555 antigen may be in various forms such as in free form, polymerized, chemically or physically modified, and/or coupled (i.e., linked) to a carrier molecule. Coupling to a carrier may increase the immunogenicity and (further) suppress the biological activity of the ZNF555 polypeptide. In this regard, the carrier molecule may be any carrier molecule or protein conventionally used in immunology such as for instance KLH (Keyhole limpet hemocyanin), ovalbumin, bovine serum albumin (BSA), a viral or bacterial anatoxin such as toxoid tetanos, toxoid diphteric B cholera toxin, mutants thereof such as diphtheria toxin CRM 197, an outer membrane vesicle protein, a polylysine molecule, or a virus like particle (VLP). In a preferred embodiment, the carrier is KLH or CRM197 or a VLP.

Coupling of ZNF555 to a carrier may be performed by covalent chemistry using linking chemical groups or reactions, such as for instance glutaraldehyde, biotin, etc. Preferably, the conjugate or the ZNF555 protein or fragment or mimotope is submitted to treatment with formaldehyde in order to complete inactivation of ZNF555.

In a particular embodiment, the ZNF555 antigen comprises a full length ZNF555 protein, optionally coupled to a carrier protein. In a preferred embodiment, the ZNF555 antigen comprises a protein comprising SEQ ID NO: 3, or a sequence having at least 90% identity to SEQ ID NO: 3, coupled to a carrier protein.

In another particular embodiment, the ZNF555 antigen comprises an immunogenic peptide or mimotope of ZNF555, optionally coupled to a carrier protein. In a more preferred embodiment, the ZNF555 antigen comprises a polypeptide of at least 10 amino acids long.

The immunogenicity of the ZNF555 antigen may be tested by various methods, such as by immunization of a non-human animal grafted with human immune cells, followed by verification of the presence of antibodies, or by sandwich ELISA using human or humanized antibodies. The lack of biological activity may be verified by any of the activity tests described in the application. In a preferred embodiment, the ZNF555 antigen has less than 20%, more preferably less than 15%, 10%, 5% or even 1% of the activity of a wild-type ZNF555 protein in an in vitro method (see the Luciferase reporter assay of the experimental part). The constructs on the base of pGL3 vectors (Promega) containing the 4qA enhancer and a promoter (SV40 or ANT1 or FRG1) (FIG. 14) were used to test the effect of anti-ZNF555 antibody and will be compared with the effect of siZNF555 knockdown (see experimental part).

To construct the pANT1 and p4qAe_ANT1 plasmids expressing the endogenous luciferase under the control of the ANT1 promoter, a DNA fragment of 715 bp containing the wild type human ANT1 promoter was amplified by PCR using the following primers: FW: 5'-GCTAGATCTGAAT-TCACCTAGTGGCCC-3' (SEQ ID NO: 22) and RV: 5'-TCTAAGCTTCGCGCAGTCCCCGA-3' (SEQ ID NO: 23); the fragment was inserted into the pBasic and p4qAe vector backbones via BglII and HindIII sites.

The construct pFRG1 (FIG. 14) with the human FRG1 promoter was designed earlier (35) and the 4qAe PCR fragment was inserted in the MluI opened pFRG1 vector upstream from the FRG1 promoter (p4qAe_FRG1).

In a particular embodiment, the invention relates to an inactivated and immunogenic ZNF555.

In a further particular embodiment, the invention relates to a ZNF555 protein or a fragment or mimotope thereof conjugated to a carrier molecule.

In a further aspect, the invention relates to a vaccine comprising a ZNF555 antigen, a suitable excipient and, optionally, a suitable adjuvant.

Such molecules and conjugates and vaccines represent potent agents for use to immunize subjects, thereby causing a sustained ZNF555 inhibition. Upon repetition, such methods can be used to cause a permanent ZNF555 inhibition.

A further object of the invention relates to of a method for inducing the production of antibodies that neutralize the activity of endogenous ZNF555 in a subject in need thereof, the method comprising administering to said subject a therapeutically effective amount of a ZNF555 antigen or vaccine.

The ZNF555 antigen or vaccine may be used for treating any disease linked to an over-production of ZNF555. More specifically, this invention relates to a method for treating a musculoskeletal disease linked to an over-production of ANT1 in a subject in need thereof, comprising administering to the subject a therapeutically effective amount of a ZNF555 antigen or of a vaccine composition comprising a ZNF555 antigen.

Administration of a compound of the invention, such as an antigen or vaccine of the invention, may be by any suitable route, such as by injection, preferably by intramuscular, subcutaneous, transdermal, intravenous or intraarterial injection; or by nasal, oral, mucosal or rectal administration.

Therapeutic Compounds and Compositions

The invention also relates to compositions comprising as an active ingredient, typically as a therapeutic compound, a ZNF555 inhibitor or antigen as herein described, preferably together with a pharmaceutically acceptable carrier or excipient. A typical composition is for use for suppressing, repressing, inhibiting or decreasing ZNF555 and/or ANT1 transcription/expression in target cells, typically in diseased muscle cells.

The active ingredient of the present invention can be designed to increase the compatibility with a therapeutic or prophylactic use in a mammal, preferably a human being. It can be, for example, glycosylated, methylated, acetylated, phosphorylated, for targeting a specific type of tissue, in particular a pathological muscle tissue such as a FSHD muscle tissue.

A "pharmaceutical composition" refers to a formulation of a compound of the invention (active ingredient) and a medium generally accepted in the art for the delivery of biologically active compounds to the subject in need thereof. Such a carrier includes all pharmaceutically acceptable carriers, diluents, medium or supports therefore. Conventional pharmaceutical practice may be employed to provide suitable formulations or compositions to subjects, for example in unit dosage form.

The compounds or compositions according to the invention may be formulated in the form of ointment, gel, paste, liquid solutions, suspensions, tablets, gelatin capsules, capsules, suppository, powders, nasal drops, or aerosol, preferably in the form of an injectable solution or suspension. For injections, the compounds are generally packaged in the form of liquid suspensions, which may be injected via syringes or perfusions, for example. In this respect, the compounds are generally dissolved in saline, physiological, isotonic or buffered solutions, compatible with pharmaceutical use and known to the person skilled in the art. Thus, the compositions may contain one or more agents or excipients selected from dispersants, solubilizers, stabilizers, preservatives, etc. Agents or excipients that can be used in liquid and/or injectable formulations are notably methylcellulose, hydroxymethylcellulose, carboxymethylcellulose, polysorbate 80, mannitol, gelatin, lactose, vegetable oils, acacia, etc. The carrier can also be selected for example from methyl-beta-cyclodextrin, a polymer of acrylic acid (such as carbopol), a mixture of polyethylene glycol and polypropylene glycol, monoetrhanol amine and hydroxymethyl cellulose.

The compositions generally comprise an effective amount (dose) of a compound of the invention, e.g., an amount that is effective to inhibit ZNF555. The dose may be adjusted by the skilled person depending on the treated subject, the route of administration, the targeted tissue, any other biologically active compound possibly administered together with the compound of the invention, etc.

Generally, the compositions according to the invention comprise from about 1 µg to 1000 mg of a ZNF555 inhibitor, such as from 0.001-0.01, 0.01-0.1, 0.05-100, 0.05-10, 0.05-5, 0.05-1, 0.1-100, 0.1-1.0, 0.1-5, 1.0-10, 5-10, 10-20, 20-50, and 50-100 mg, for example between 0.05 and 100 mg, preferably between 0.05 and 5 mg, for example 0.05, 0.1, 0.2, 0.3, 0.4, 0.5, 1, 2, 3, 4 or 5 mg. The dosage may be adjusted by the skilled person depending on the inhibitor and the disease.

As previously indicated, the compositions of the invention can further comprise one or more additional active compounds or adjuvant, for simultaneous or sequential use.

Various protocols may indeed be used for the administration, such as simultaneous or sequential administration of any product(s) as defined previously, single or repeated administration, etc., which may be adjusted by the skilled person.

The invention also relates to a method for preparing a pharmaceutical composition, comprising mixing a ZNF555 inhibitor as previously described and a pharmaceutically acceptable excipient, and formulating the composition in any suitable form or container (syringe, ampoule, flask, bottle, pouch, etc.).

Also herein provided is a kit comprising (i) at least one biologically active product as herein described, typically a ZNF555 inhibitor or any composition comprising such an active product as previously described (ii) at least one container, and optionally (iii) written instructions for using the kit.

Treatment

The products (compounds and compositions) of the invention may be used to prevent or treat any disease related to an inappropriate ZNF555 or ANT1 expression, either as such (directly) or together with a distinct pharmaceutically active molecule or drug classically used by the physician for a particular disease.

In a particular aspect, the herein described compositions comprising ZNF555 comprise at least one distinct pharmaceutically active molecule or drug.

The invention also provides methods for preventing or treating a disease comprising inhibiting ZNF555 in the subject, preferably by administering a ZNF555 inhibitor, as herein above described, for example a ZNF555 inhibitory nucleic acid such as a shRNA, or vaccine to the subject.

Specific examples of diseases that can benefit from a treatment involving inhibition of ZNF555 according to the invention are all the clinical situations linked to an unwanted over-transcription or over-expression of ANT1 compared to standard values, typically a musculoskeletal disease ("MSD") or a cancer, preferably a myopathy such as Facioscapulohumeral Dystrophy (FSHD). The MSD can also be for example muscular cachexia.

Cancer that can benefit from a treatment involving inhibition of ZNF555 according to the invention are any kind of cancer or tumour, including a carcinoma, a sarcoma, a lymphoma, a melanoma, a paediatric tumour and a leukaemia tumour. In particular, the cancer is selected from a gastrointestinal sarcoma, a renal cancer, a breast cancer, a leukaemia, an Hodgkin lymphoma, a neuroblastoma, a prostate cancer, an oesophagus cancer, a colon cancer, a rectal cancer, an ovarian cancer, a pancreatic cancer, a testicular cancer, a bladder cancer, a lung cancer, a thyroid cancer, an osteosarcoma and a melanoma.

A typical cancer is selected for example from rhabdomyosarcoma, lymphoma and melanoma. A preferred cancer is rhabdomyosarcoma.

A particular object of the invention relates to a compound modulating, typically decreasing or inhibiting the expression or activity of ZNF555, typically a ZNF555 inhibitor, for use for modulating, typically decreasing or inhibiting, the expression or activity of ANT1 in a subject.

In a preferred embodiment, the invention comprises decreasing or inhibiting the expression or activity of ZNF555 in a subject, or exposing the subject to a ZNF555 inhibitor. Such embodiment is particularly suited to prevent or treat a subject at risk of, or who has been diagnosed with a musculoskeletal disease. In a particular embodiment, exposing the subject to an inhibitor comprises administering the inhibitor to the subject.

A further object of the invention relates to a compound that inhibits or decreases the expression or activity of ZNF555 for use for preventing or treating a musculoskeletal disease in a subject.

Another object of the invention relates to the use of a compound that modulates the expression or activity of ZNF555 for the manufacture of a composition for modulating, typically decreasing or inhibiting, the expression or activity of ANT1 in a subject.

A further object of the invention relates to the use of a compound that inhibits or decreases the expression or activity of ZNF555 for the manufacture of a composition for preventing or treating a musculoskeletal disease in a subject.

A further object of the invention relates to a method for modulating, typically decreasing or inhibiting, the expression of ANT1 in a subject, comprising exposing the subject to a compound that modulates the expression or activity of ZNF555.

A further object of the invention relates to a method for preventing or treating a musculoskeletal disease in a subject, comprising exposing the subject to a compound that modulates the expression or activity of ZNF555.

Another object of the invention relates to the use of a compound that modulates the expression or activity of ZNF555 for use in a method for modulating, typically decreasing or inhibiting, the expression or activity of ANT1 in a subject.

A further object of the invention relates to the use of a compound that inhibits or decreases the expression or activity of ZNF555 for use in a method for preventing or treating a musculoskeletal disease in a subject.

The duration, dosages and frequency of administering compounds or compositions of the invention may be adapted according to the subject and disease. The treatment may be used alone or in combination with other active ingredients, either simultaneously or separately or sequentially.

The compounds or compositions according to the invention may be administered in various ways or routes such as, without limitation, by systemic injection, intramuscular, intravenous, intraperitoneal, cutaneous, subcutaneous, dermic, transdermic, intrathecal, ocular (for example corneal) or rectal way, or by a topic administration on an inflammation site, and preferably by intramuscular or intravenous injection.

A typical regimen comprises a single or repeated administration of an effective amount of a ZNF555 inhibitor over a period of one or several days, up to one year, and including between one week and about six months. It is understood that the dosage of a pharmaceutical compound or composition of the invention administered in vivo will be dependent upon the age, health, sex, and weight of the recipient (subject), kind of concurrent treatment, if any, frequency of treatment, and the nature of the pharmaceutical effect desired. The ranges of effectives doses provided herein are not intended to be limiting and represent preferred dose ranges. However, the most preferred dosage will be tailored to the individual subject, as is understood and determinable by one skilled in the relevant arts (see, e.g., Berkowet et al., eds., The Merck Manual, 16$^{th}$ edition, Merck and Co., Rahway, N.J., 1992; Goodmanetna., eds., Goodman and Cilman's The pharmacological Basis of Therapeutics, 10$^{th}$ edition, Pergamon Press, Inc., Elmsford, N.Y., (2001)).

Methods of Identifying Candidate Therapeutic Compounds

The invention also provides methods for identifying candidate therapeutic compounds for use for preventing or treating a musculoskeletal disease, typically a MSD involving an unwanted expression of ANT1.

Herein described is more particularly a method for identifying and selecting a compound inhibiting or decreasing the expression or activity of ZNF555, preferably of a ZNF555 protein encoded by a nucleic acid sequence selected from SEQ ID NO: 1, SEQ ID NO: 47 (NM_001172775.1), SEQ ID NO: 48 (NM_152791.4), SEQ ID NO: 49 (XM_011527714.1), SEQ ID NO: 50 (XM_011527715.1), SEQ ID NO: 51 (XM_011527716.1) and any variant thereof, typically by a sequence selected from SEQ ID NO: 1, SEQ ID NO: 47, SEQ ID NO: 48 and any variant thereof, preferably by SEQ ID NO:1 or a variant thereof, the method comprising a step of detecting and/or measuring the level of expression of ZNF555 or ANT1 in a muscle cell in the presence of a test compound, wherein an absent or decreased expression of ZNF555 or ANT1 in comparison with a control muscle cell that has not been exposed to or contacted with the test compound, is indicative of the capacity of said compound to inhibit or decrease the expression or activity of ZNF555 in said cell.

As used herein a "candidate therapeutic compound" or "test compound" may be any chemical entity under evaluation as a potential therapeutic. In some embodiments the agent is an organic molecule. In some embodiments the agent is a peptide, a protein, a glyco-protein, or a lipoprotein. In some embodiments the agent is an antibody.

In some embodiments the agent has not been previously determined to have a biological activity implying a utility as a therapeutic agent for treatment of musculoskeletal disease. In some embodiments the agent has been previously determined to have a biological activity implying a utility as a therapeutic agent for treatment of musculoskeletal disease.

Further aspects and advantages of the present invention will be described in the following examples which are given for purposes of illustration and not by way of limitation.

LEGEND TO THE FIGURES

FIG. 1: Schematic presentation of 4qA allele and gene candidates in the 4q35 locus.

Figure 2:
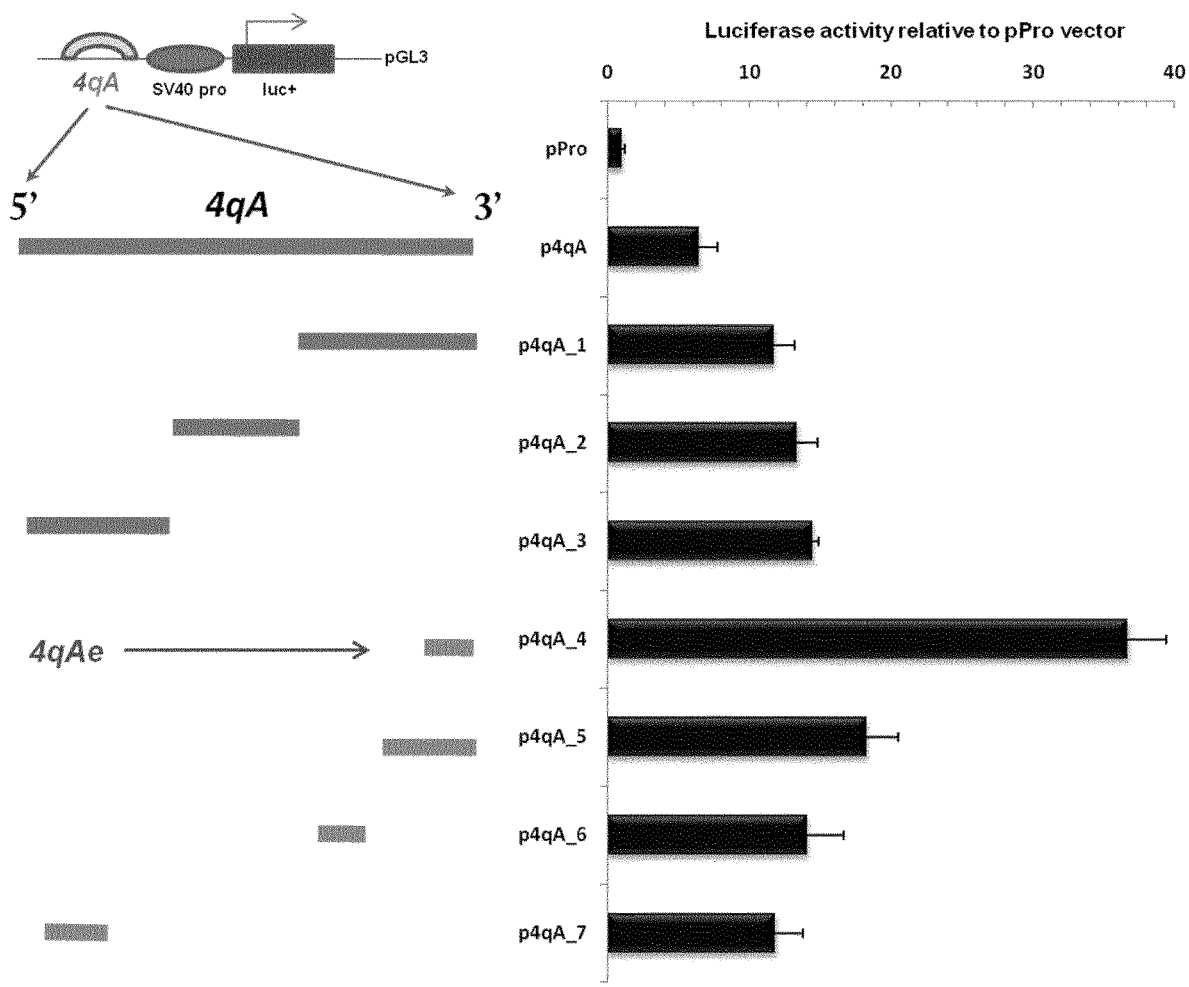

FIG. 2: A BSR repeat from 4qA allele holds a transcriptional activator property. The transcriptional effect of the fragments from 4qA allele was tested 48 hrs after transfection in rhabdomyosarcoma cells. The enhancer strength was quantified relative to the luciferase activity generated by the pGL3 plasmid with the SV40 promoter (pPro). The equal amounts of the plasmids were transfected. Luciferase signals were normalized to the total protein content in the extracts. All constructs were on the bases of pGL3 enhancerless vector (pPro) carrying an SV40 promoter. All inserts from the 4qA region were placed upstream of the SV40 promoter. Solid pink bar corresponds to the initial 4qA fragment of the 20 BSR inserted in pGL3, which was divided into three sub-fragments (p4q4_1, p4q4_2 and p4q4_3) in the second set of cloning. p4q4_4, p4q4_5, p4q4_6 and p4q4_7 correspond to the small fragments of 4qA (1-3 BSR). Error bars correspond to a standard deviation of the values of three independent experiments.

Figure 3:
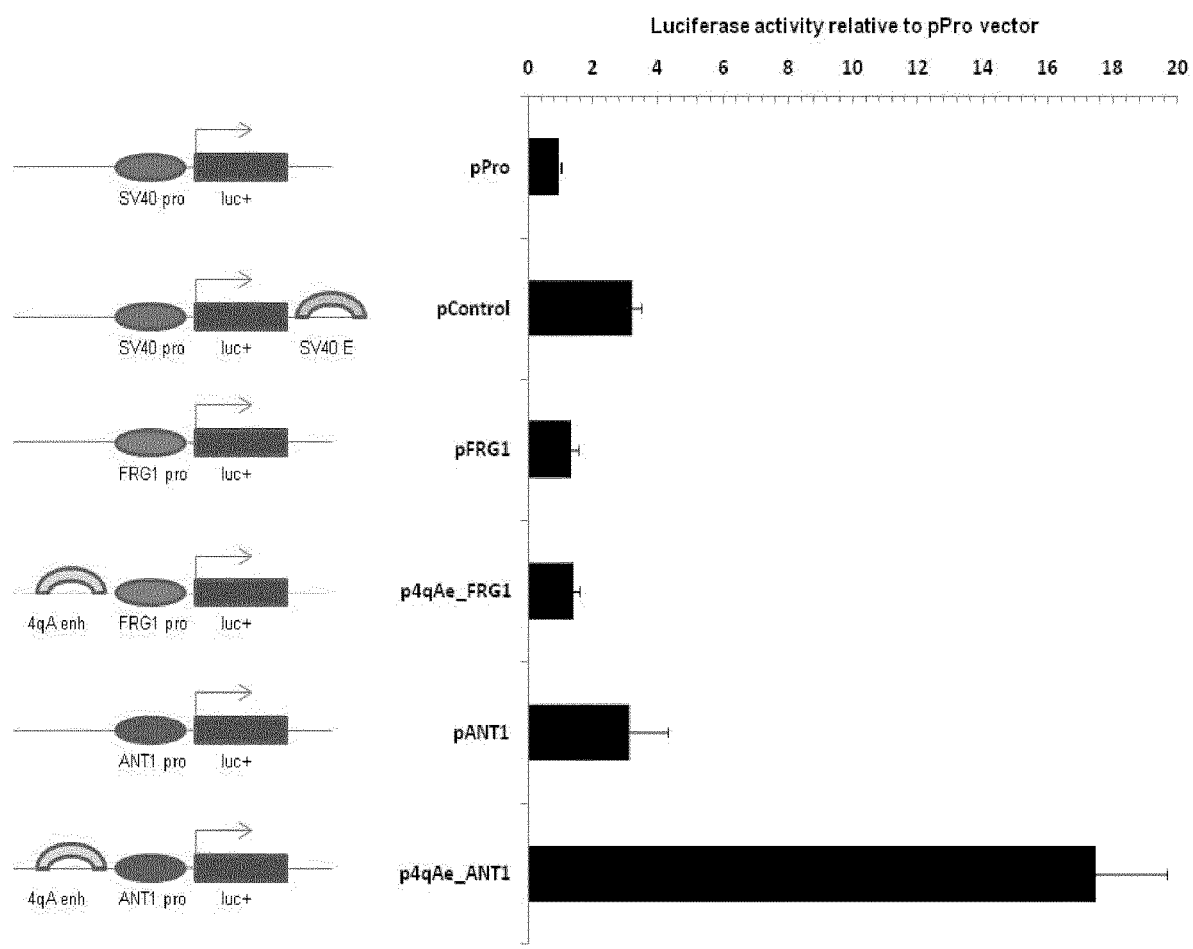

FIG. 3: A BSR repeat from 4qA allele can regulate the promoter activity of ANT1 gene. The transcriptional effect of the 4qAe was tested 48 hrs after transfection in rhabdomyosarcoma cells. The enhancer strength was quantified relative to the luciferase activity generated by the pGL3 plasmid with the SV40 promoter (pPro) referenced as 1. The equal amounts of the plasmids were transfected. Luciferase signals were normalized to the total protein content in the extracts. All our constructs were on the bases of pGL3 vector. Bars indicate the luciferase reporter gene from pGL3, ovals indicate the promoter regions (ANT1 pro, FRG1 pro and SV40 pro) that were placed upstream from the luciferase sequence and arches indicate an enhancer (4qAe, SV40 enh). Error bars correspond to a standard deviation of the values of three independent experiments.

Figure 4:
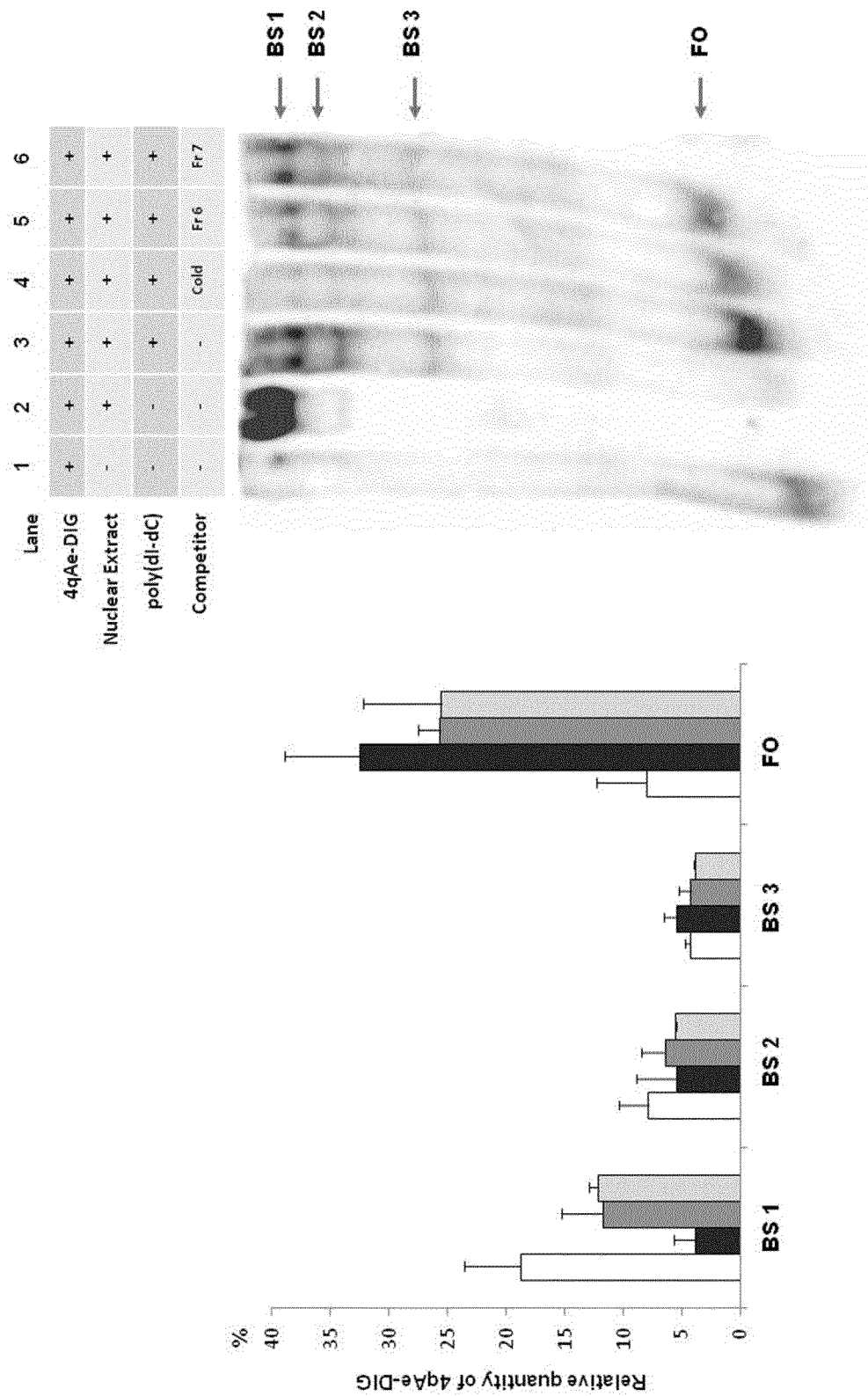
Figure 4:
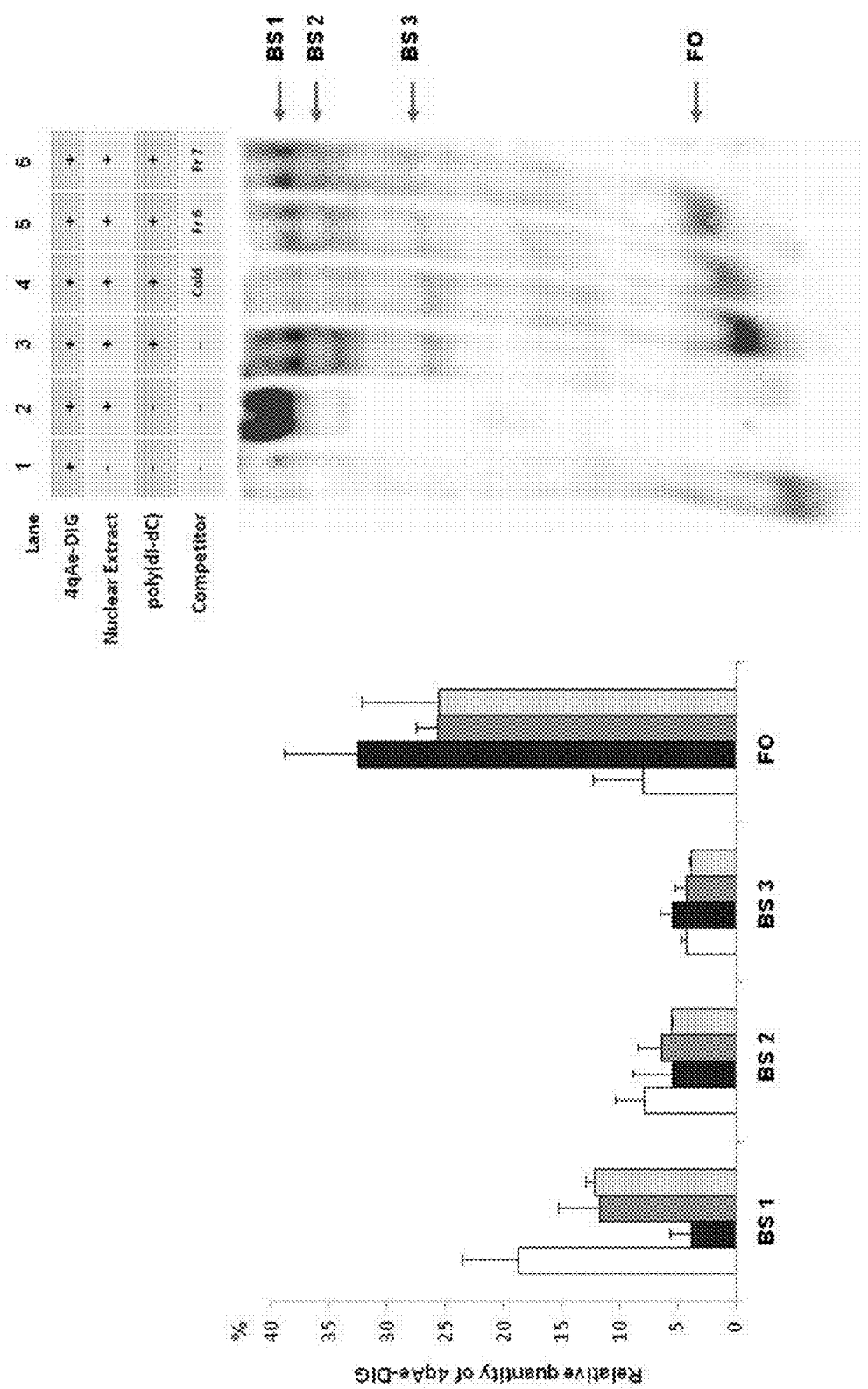

FIG. 4: Identification of 4qAe binding proteins. (A) DIG-EMSA indicates specific binding of 4qA enhancer (4qAe) with proteins from the nuclear extract of RMS cells. Lane 1 corresponds to the DIG-labelled 4qAe free oligo (FO), which was reacted with the nuclear extract (Lane 2) in the presence of poly(dI-dC) (Lane 3). The binding specificity of 4qAe was examined by the competition in binding reaction of nuclear proteins and the DIG-labelled 4qAe probe adding 200 fold molar excess of the unlabeled homologous 4qAe probe (cold competitor, Lane 4) or heterologous probes Fr 6 (Lane 5) or Fr 7 (Lane 6). The band shift 1 (BS 1) was specific for 4qAe. The relative quantity of 4qAe oligo was calculated as a percentage of total quantity (100%) of the oligo per lane. Error bars correspond to a standard deviation of the values of three independent experiments. (B) Schematic description of DIG-EMSA-MS approach. The gel shift experiment was run in double. One set of the samples (Exp 1, Ctl 1) was performed with the DIG labelled EMSA probe and the specific band was detected by anti-DIG antibodies. The resulting from the first set of the EMSA experiment film was superposed with the second set of samples (Exp 2, Ctl 2) and the corresponding bands were excised and analyzed by Mass spectrometry (MS). The nuclear extracts of control (Ctl 2) samples were run without an addition of the DNA probe as it was in experimental probe (Exp 2).

Figure 5:
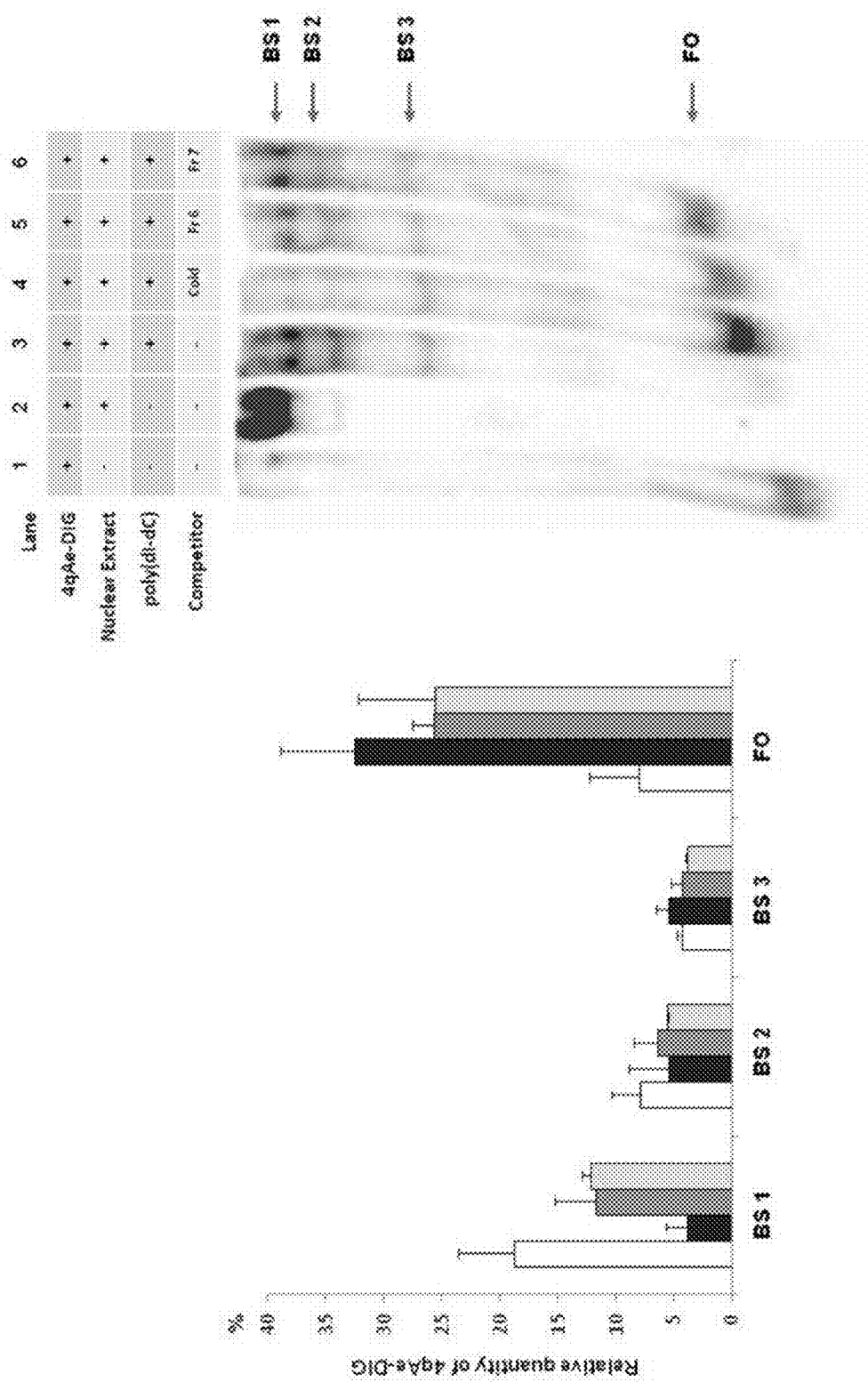

FIG. 5: ZNF555 expression is specific for myoblast cells. (A) Total mRNA from myogenic lineage cells: myoblasts, miPS (myoblast-derived iPS) cells and mMSC (miPS-derived mesenchymal stem cells) and non-myogenic: fibroblasts (fibro) and HeLa cells was tested for the ZNF555 expression by means of RT-PCR (n=4-8). Data are normalized against GAPDH mRNA level and the value for GAPDH was equated to 10. t-test for paired differences with HeLa cells was performed; *** $p<0.001$, *$p<0.05$. (B) ZNF555 protein expression analysis by Western blotting in FSHD (Myo_F), normal (Myo_N) and immortalized (Myo-i) myoblasts, rhabdomyosarcoma (RMS) and HeLa cells. B-actin was used as a control. The data present the results from two independent experiments.

FIG. 6: ZNF555 knockdown promotes the changes of luciferase expression in constructs with 4qAe enhancer. (A) Effect of 50 nm esiRNA-mediated knockdown of ZNF555 gene in RMS cells. mRNA quantification by qRT-PCR was done 72 h post transfection. Negative control (Ctl): esiRNA-targeting luciferase was used as a reference and set to 100%. The results represent three independent experiments measured in triplicate. (B) Western blotting validation of esiRNA-induced down-regulation of ZNF555 72 h post transfection. Negative control (Ctl): esiRNA-targeting luciferase. (C) Effect of ZNF555 knockdown using 50 nm esiRNA on 4qAe enhancer activity in RMS cells. The ZNF555 esiRNA was co-transfected with the set of luciferase reporter pGL3-based constructs, which contain the 4qAe enhancer and/or the promoters of ANT1 and FRG1 genes. The luciferase expression was analyzed 72 h post transfection. The data shown represent results of two experiments performed in triplicate and normalized against the luciferase expression of corresponding constructs without ZNF555 knockdown (set to 100%). The positive control (Ctl) performed with siRNA against luciferase gene. Data in A and C are shown as mean±SD.

Figure 7:
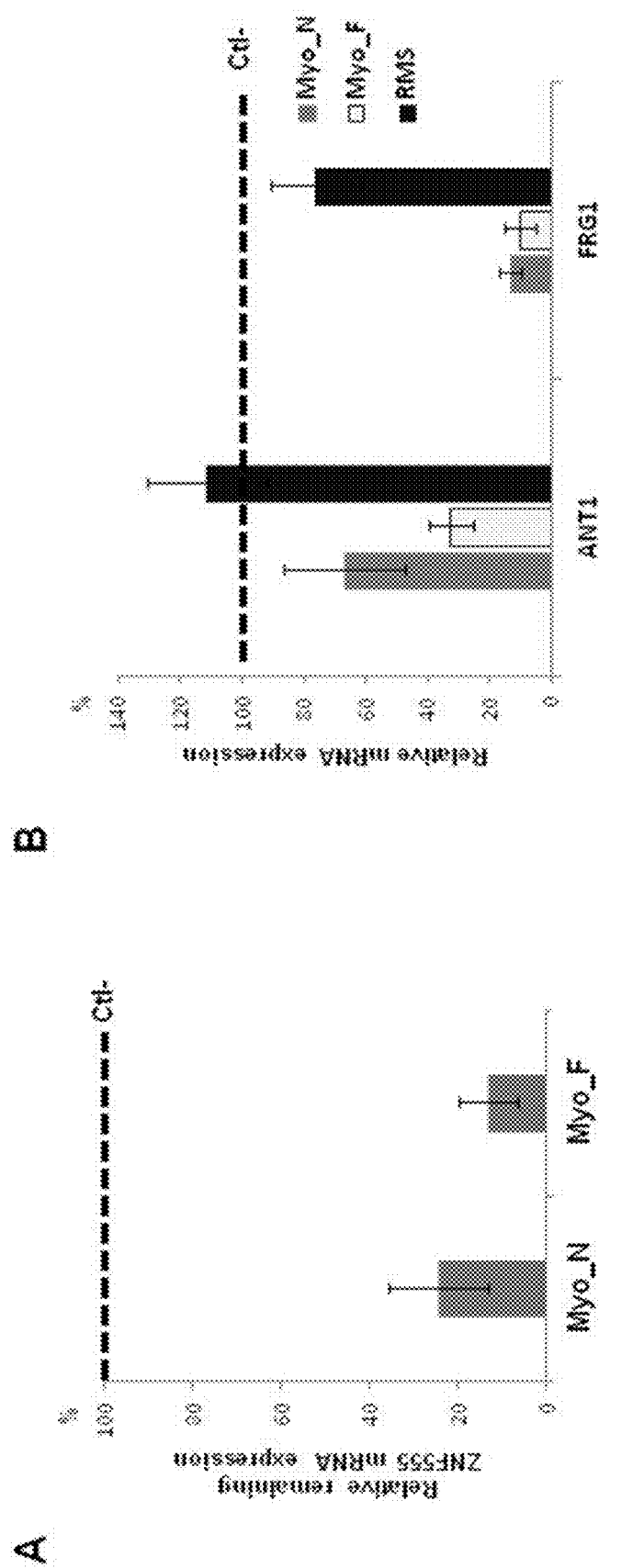

FIG. 7: ZNF555 knockdown promotes the changes of ANT1 and FRG1 expression. (A) Representative knockdown of ZNF555 in primary normal and FSHD myoblasts using esiRNA. Negative control (Ctl−): esiRNA-targeting luciferase. (B) Effect of 50 nm esiRNA$_{ZNF555}$ on ANT1 and FRG1 gene expression in the primary myoblasts of FSHD patients and healthy individuals and rhabdomyosarcoma cells (RMS). The extracted mRNA was analyzed by qPCR. Negative control (Ctl−): esiRNA-targeting luciferase. (A-B) Results represent two independent RT-qPCR experiments performed in triplicate and normalized against GAPDH and esiRNA$_{LUC}$ Ctl− referenced as 100%. t-test for paired differences with corresponding esiRNA$_{LUC}$ Ctl− was performed; ** $p<0.01$, * $p<0.05$. Myo-N: normal myoblasts, Myo-F: FSHD myoblasts, RMS: rhabdomyosarcoma cells.

Figure 8:
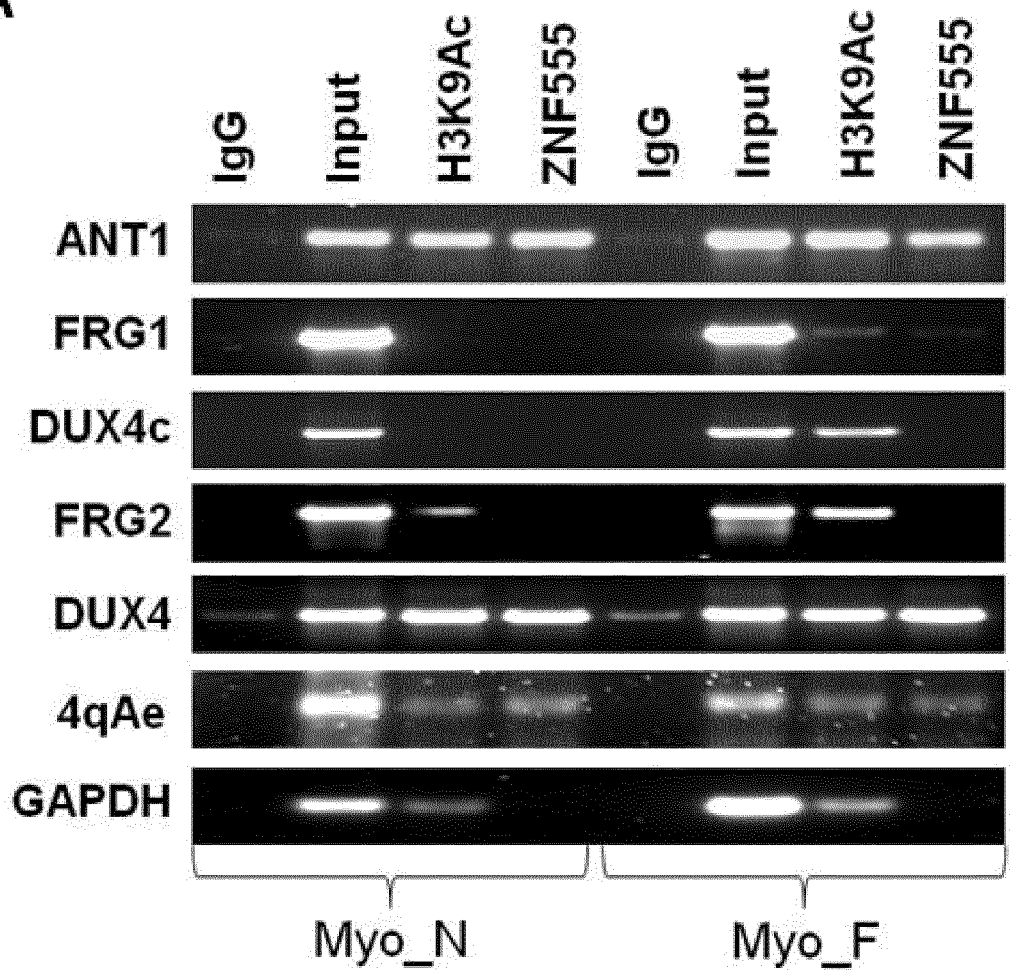
Figure 8:
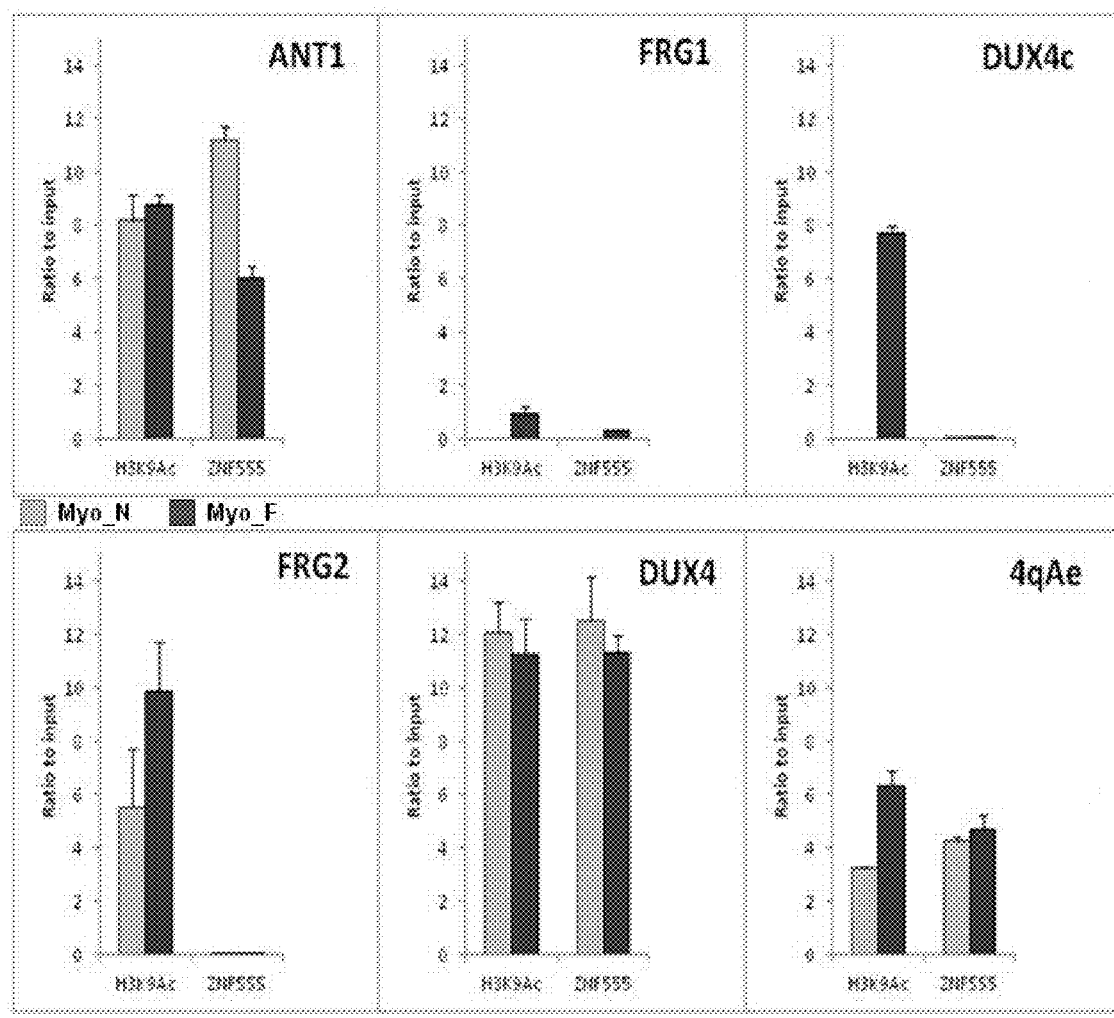

FIG. 8: ZNF555 is associated with the FSHD region 4q35 in vivo. (A) Chromatin immunoprecipitation (ChIP) performed in control (Ct) and facioscapulohumeral muscular dystrophy (FSHD) myoblasts using antibodies against ZNF555 and H3K9Ac. Input (positive control) DNA represents total chromatin and negative control represents the chromatin precipitated by normal rabbit IgG. (B) ChIP analysis of control (Ct) and FSHD myoblasts. ChIP results were normalized against Input=10 and the IgG negative control was subtracted. GAPDH was amplified as a positive control for H3K9Ac. All PCR experiments were performed in a linear range of amplification and the band intensities were measured by ImageJ software. Student deviation was calculated from the data of 2-3 independent experiments.

Figure 9:
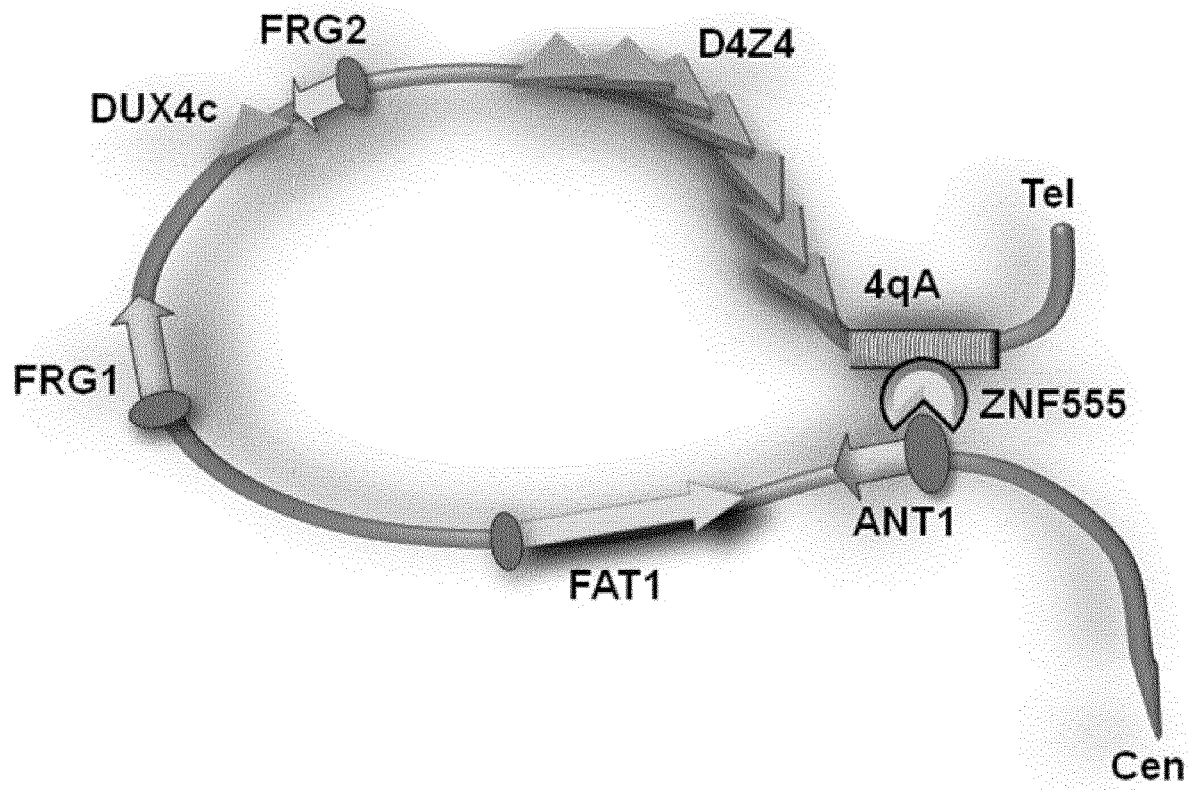

FIG. 9: Transcriptional control model of BSR 4qA allele through ZNF555 in the 4q35 locus.

FIG. 10: BSR homology. Exhaustive pairwise alignment using neighbor-joining phylogeny analysis by Clone Manager7 software shows the high homology of 12 monomers of the β-satellite repeats (BSR) inside the 4qA allele.

Figure 11:
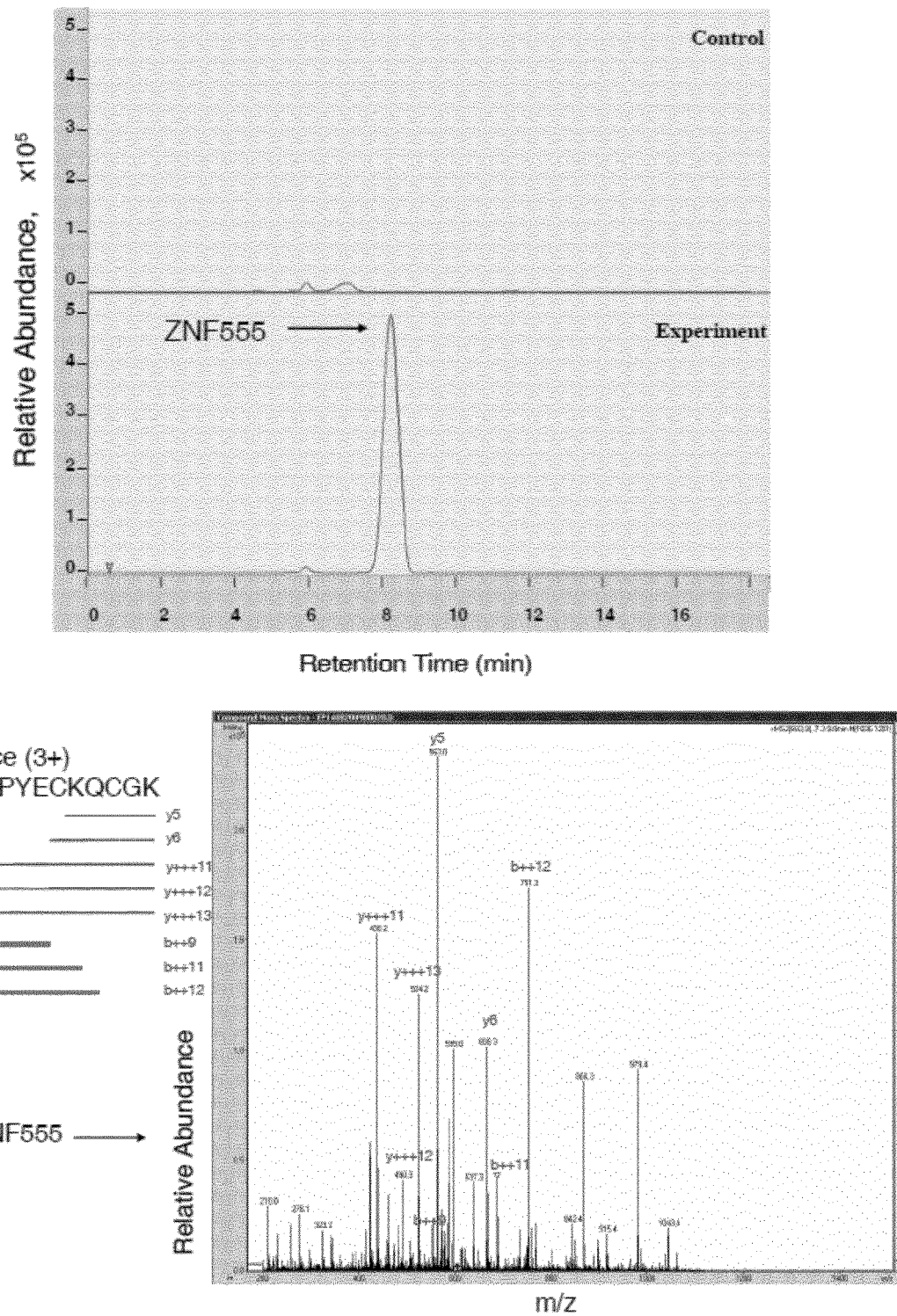
Figure 11:
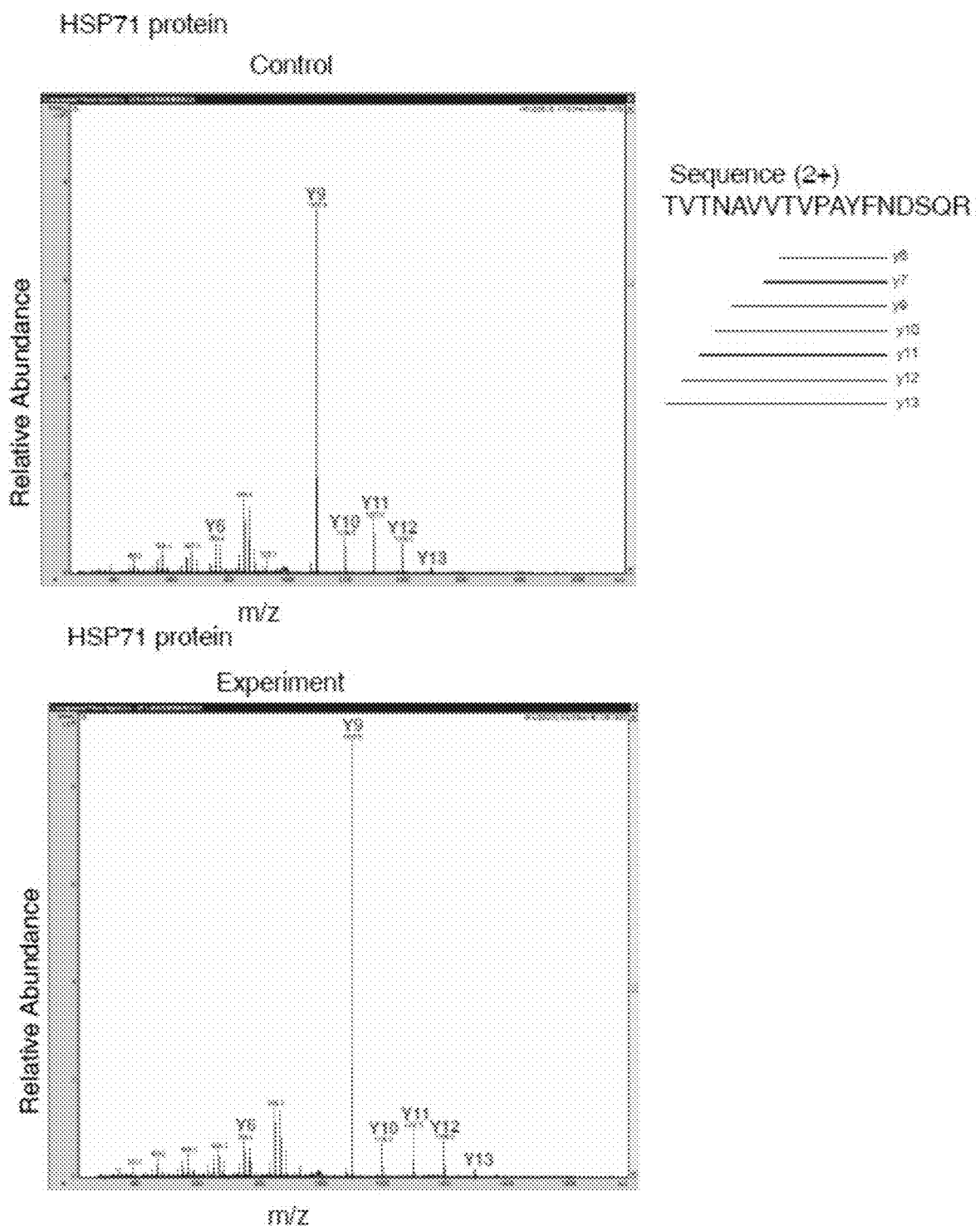

FIG. 11: ZNF555 specifically binds the 4qA enhancer (4qAe) from 4qA allele. (A) The protein composition between the EMSA with (experiment) and without (control) 4qAe-oligo was compared. The primary protein bands were excised from the gel, digested with trypsin, and analyzed by NanoLC-ESI-MS/MS for peptide mass fingerprint (PMF). The sequences obtained were screened against the SWISS-PROT database using the MASCOT search engine. The searches were carried out with a peptide mass accuracy tolerance of 100 ppm for external calibration. Extract Ion Chromatogram (EIC) on daughter ion m/z 438.2 belongs to parental ion m/z 603.8 of Zinc finger protein 555 (Q8NEP9). The data correspond to the experiment with 4qAe and to the control without 4qAe. (B) NanoLC-ESI-MS/MS spectrums of Heat shock protein 71 kDa. The MRM analysis of m/z 992.5 (2+) of HSP71 (P11142) in control (Ct) and in experiment samples (shifted to 4qAe enhancer).

Figure 12:
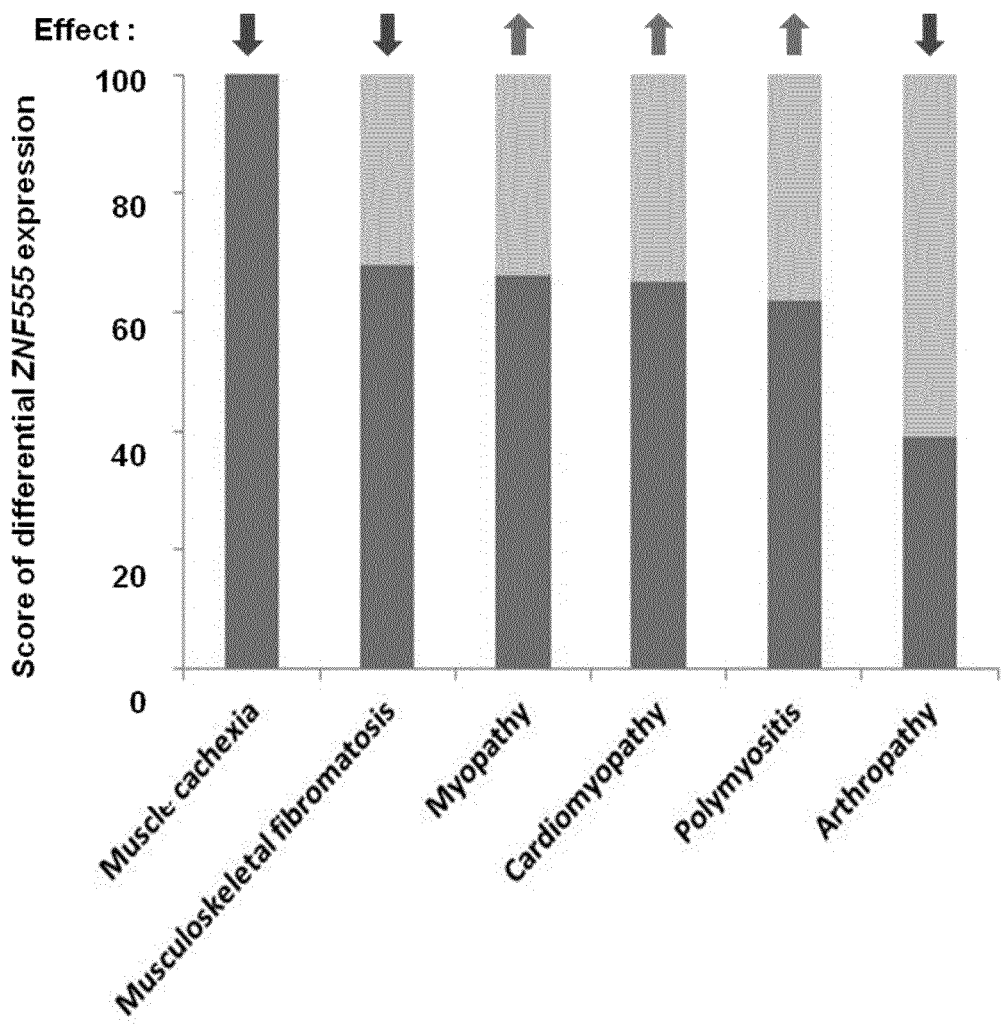

FIG. 12: Analysis of ZNF555 RNA expression under different pathologies showed the highest score for musculoskeletal and connective tissue diseases. Data were extracted from Disease Atlas (see Worldwide Website: nextbio.com). Disease Atlas ranks diseases, traits, conditions, and surrogate endpoints associated with a gene. Results are grouped by disease and ranked according to statistical significance. The Illumina (Illumina acquired NB) NextBio analysis tool was used to analyze ZNF555 at different pathologies. NextBio is a curated and correlated repository of experimental data derived from an extensive set of public sources (e.g., ArrayExpress and GEO) that allows the user to compare patterns of gene expression between thousands of genomic signatures derived from published datasets. Statistical analysis is carried out using rank-based enrichment analysis to compute pairwise correlation scores of the uploaded dataset and all studies contained in NextBio. The statistical analysis method used by NextBio is referred to as a "Running Fischer" (36). A numerical score of 100 corresponds to the most significant result for ZNF555 gene expression and the scores of the other results were noimalized to the top-ranked result. Query executed on date. All samples were compared with healthy control.

FIG. 13: ADAM12 is a predicted functional partner of ZNF555. The analysis was performed using the database of known and predicted protein-protein Interactions (http://string-db.org/).

FIG. 14: Constructs used in the experimental part.

FIG. 15: List of primers used in the experimental part.

FIG. 16: List of proteins identified by analyzing the specific for 4qAe band (with cold competitor) obtained from DIG-EMSA experiment on TE671 cells. The results presented in this figure were obtained by NanoLC-ESI-MS/MS for peptide mass fingerprint (PMF). The gray highlighted proteins were detected only in experimental samples.

FIG. 17: List of proteins identified by analyzing the control (Ctl) band without DNA obtained from DIG-EMSA experiment on TE671 cells. The results presented in this figure were obtained by NanoLC-ESI-MS/MS for peptide mass fingerprint (PMF).

Figure 18:
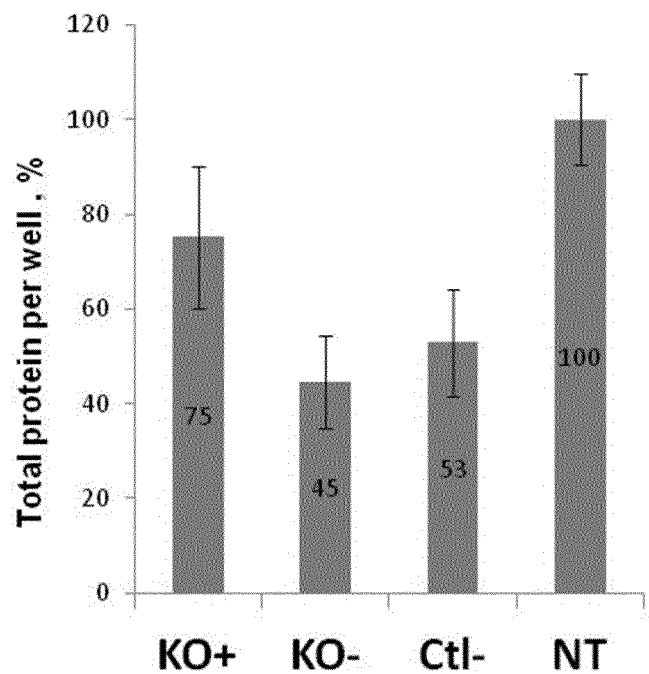

FIG. 18: ZNF555 knockdown increases the cell survival. Rhabdomyosarcoma cells were transfected with the set of plasmids without (KO−) and with (KO+) siRNA$_{ZNF555}$ Total protein (mg/ml) was extracted and measured 72 h post-transfection using QuantiPro BSA Assay Kit (Sigma-Aldrich). The results shown represent results of eight experiments performed in triplicate. They were normalized against non-transfected control cells (NT). Negative control (Ctl−): esiRNA-targeting luciferase. Data are shown as mean±SD.

Figure 19:
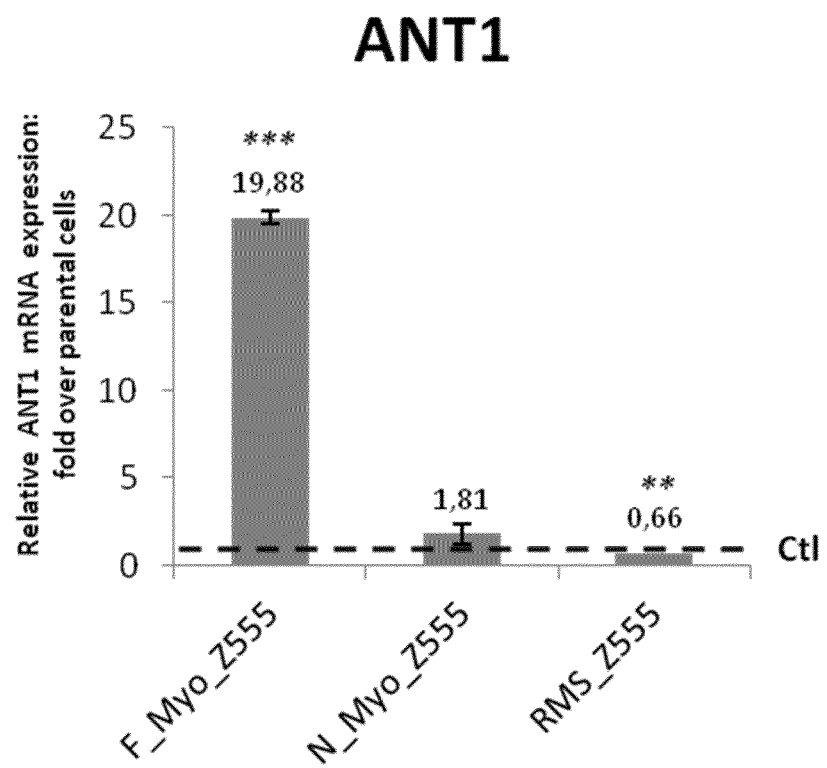

FIG. 19: ZNF555 overexpression promotes changes in the expression ANT1. Effect of pOZ-FHHN_YFP_ZNF555 retroviral vector on ANT1 gene expression in the immortalized myoblasts of FSHD patients (F_Myo_Z555) and healthy individuals (N_Myo_Z555) and RMS (RMS_Z555). The extracted mRNA was analyzed by qPCR. Results represent an independent RT-qPCR experiment performed in triplicate and normalized against GAPDH and parental cells (Ctl) referenced as 1. t-test for paired differences with corresponding parental cell Ctl was realized; *P<0.001, P<0.01.

EXAMPLES

Example 1

Material and Methods
Cell Culture

Inventors performed experiments on primary human myoblasts from three healthy individuals: Myo_N1, Myo_N2, Myo_N3 and three patients living with Facioscapulohumeral Dystrophy (FSHD): Myo_F1 (D4Z4$^4$), Myo_F2 (D4Z4$^7$) and Myo_F3 (D4Z4$^2$) (Myobank-AFM, Institute of Myology, Paris and CHU A. De Villeneuve, Montpellier) (34), the iPS cells were generated from myoblasts, and mesenchymal stem cells were differentiated from the iPS cells (37).

CD56-positive myoblasts were cultured in a growth medium consisting of 199 medium and DMEM (Invitrogen Carlsbad, Calif.) in a 1:4 ratio, supplemented with 20% FCS (Invitrogen), 2.5 ng/ml hepatocyte growth factor (Invitrogen), 0.1 µmol/l dexamethasone (Sigma-Aldrich, St. Louis, Mo., USA) and 50 µg/ml gentamycin (Invitrogen) at 37° C. with 5% CO2. Myoblasts were differentiated in myotubes in DMEM medium with 2% FCS for six days. The multinucleated myotubes formation was controlled by haematoxylin staining (Sigma-Aldrich) Immortalized myoblasts were generated at the Institute of Myology (Paris, France) (38).

The iPS cells were maintained on human foreskin fibroblast (BJ1) feeder cells, which were mytomycin-C growth-arrested (i-Stem). The hES culture medium was KO/DMEM (Invitrogen) supplemented with a 20% knockout serum replacement (KSR) (Invitrogen), 0.1 mM nonessential amino acids (Invitrogen), 2 mM glutamax (Invitrogen), 50 µM β-mercaptoethanol (Invitrogen), and 100 UI/ml penicillin/streptomycin (Invitrogen). The iPS cells were passaged every seven days.

The MSC cells were cultured in MSC medium containing KO/DMEM (Invitrogen) supplemented with 20% FCS, 0.1 mM nonessential amino acids (NEAA) (Invitrogen), 2 mM glutamax, 50 µM β-mercaptoethanol, and 100 UI/ml penicillin/streptomycin (Invitrogen). The medium was changed every 2-3 days.

The HeLa cell line has been purchased from the ATCC Bioresource centre. The TE671 rhabdomyosarcoma cells (Sigma-Aldrich) were maintained in a standard DMEM (Gibco, Life Technologies)/10% FBS (PAA Laboratories BmbH, Pasching, Austria) medium condition with 100 UI/ml penicillin/streptomycin (Invitrogen).

Plasmids and Constructs

The constructs on the base of pGL3 vectors (Promega, USA) were used for transient transfection studies (FIG. 14). The pGL3-SV40Pro (pPro) vector contains an SV40 promoter upstream of the luciferase gene in contrast to pGL3 (pBasic) without the promoter. The pGL3-SV40Pro-SV40enh (pControl) vector containing the sequences of the SV40 promoter and the SV40 enhancer was used as a positive control to identify a putative enhancer within the BSR sequence.

The p4qA plasmid containing the BSR fragment corresponding to the 4qA allelic variant was designed earlier (18). Inventors have designed a series of new constructions p4qA_1, p4qA_2 and p4qA_3 first cutting the BSR fragment on three fragments by BglII enzyme: Fr1 (564 bp), Fr2 (435 bp) and Fr (489 bp). Each of these fragments was subcloned into the pPro vector 'upstream of the SV40 promoter. In the second series of experiments, they amplified the smaller fragments Fr4-Fr7 from Fr1, Fr2 and Fr3 and inserted them in pPro via BglII sites to find out a minimal activator inside the BSR sequence. The size of fragments varies from 63 to 203 bps. All constructs were analyzed by sequencing.

To construct the pANT1 and p4qAe_ANT1 plasmids expressing the endogenous luciferase under the control of the ANT1 promoter, a DNA fragment of 715 bp containing a wild type of human ANT1 promoter was amplified by PCR using the following primers: FW: 5'-GCTAGATCTGAAT-TCACCTAGTGGCCC-3' and RV: 5'-TCTAAGCTTCGCGCAGTCCCCGA-3'; the fragment was inserted into the pBasic and p4qAe vector backbones via BglII and HindIII sites. The construct pFRG1 (FIG. 14) with the human FRG1 promoter was designed earlier (35) and the 4qAe PCR fragment was inserted in the MluI opened pFRG1 vector upstream from the FRG1 promoter (p4qAe_FRG1).

The sequences of the fragments used in these experiments are presented in FIG. 14.

Luciferase Assay

The transfection procedure and the preparation of the complexes were performed using the JetPEI™ reagent and 0.5 µg of DNA according to the manufacture recommended protocol (Polyplus transfection Inc, USA). HeLa and TE671 cells were seeded on 48-well culture vessel, $2.5 \times 10^4$ cells per well the day before the transfection. After a 48-h incubation period, the gene activity was assessed by reagents and supplied protocol (Promega, USA). Luminescence measuring was performed on a Microlumat LB96p device (EGG Berthold, Bad Wildbad, Germany). Protein concentration in the extracts was measured by QuantiPro BSA Assay Kit (Sigma-Aldrich).

Nuclear Extract Preparation and Olygonucleotide Labelling

Nuclear extracts from TE671 were prepared using high salt lysis/extraction buffer: 10 mM NaCl, 20 mM HEPES [pH 7.6], 1.5 mM $MgCl_2$, 1 mM $ZnSO_4$, 20% glycerol, 0.1% Triton X-100, 1 mM dithiothreitol, 1 mM phenylmethylsulfonyl fluoride (39). The oligonucleotides, corresponding to the BSR-fragments were annealed (sense and antisense) and DIG-end-labelled with terminal transferase (Roche) and DIG-ddUTP (Roche).

DIG Electrophoresis Mobility Shift Assay (DIG-EMSA)

Inventors based on the protocol from the DIG Gel Shift Kit manual (Roche Applied Science) adding their modifications. Briefly, binding assay was carried out in 25 mM Hepes pH7.6, 1 mM EDTA, 10 mM $(NH_4)_2SO_4$, 1 mM DTT, 0.2% (w/v) Tween20, 30 mM KCl, and 0.5 mg poly(dI-dC) as a non-specific competitor, with 0.2 pmoles of DIG-labelled ds-oligo and 0.25 mg nuclear protein extract in a final volume of 5.5 µl. All samples were incubated for 15 min at room temperature. After the PAAG electrophoresis the DIG-labelled oligo was transferred to the positively charged nylon membrane (Hybond N+, Amersham) equilibrated in 0.5× TBE (Euromedex) by electro-blotting. The transfer was performed at 300 mA, 30V for one hour. Next, the membrane was rinsed in 2×SSC (Euromedex), air-dried during 15 min and baked at 80° C. for 30 min without UV-cross-linking. The blot was incubated with the anti-DIG antibodies (Roche Applied Science) and revealed using the ECLplus kit (Amersham). The films were scanned and developed using Kodak X-OMAT 2000 device. The sequences of oligonucleotides corresponding to Fr 4 (4qAe), Fr 6 and Fr 7 are presented in FIG. 14. The DIG-EMSA experiment was performed in triplicate and the results were treated using the ImageJ software (NIH, USA).

Detection of 4qA Enhancer-Binding Proteins

The PCR product corresponding to the strongest enhancer from BSR region was incubated with the nuclear extracts (2.5 mg protein) from TE671 cells and was shifted by the DIG-EMSA procedure. The samples were performed in double. One part of the gel was separated and subjected to DIG-EMSA in order to check for the presence of DNA-protein bands. The other part of the gel was visualized using the Coomassie Brilliant Blue 8250 (Thermo Scientific Pierce). The bands of interest were determined by the superposition of the film from DIG-EMSA and excised.

NanoLC-ESI-MS/MS for Peptide Mass Fingerprint Analysis

The protein bands corresponding to the proteins bound to the 4qAe oligo (Fr 4) were excised from the gel and processed as in (40). The gel slices were dehydrated with 300 µl of 50% acetonitrile followed by 300 µl of 100% acetonitrile, and then re-hydrated with 300 µl of 50 mM ammonium bicarbonate. A final dehydration was performed with 2 washes of 300 µl of 50% acetonitrile, followed by 2 washes of 300 µl of 100% acetonitrile. Each wash was carried out for 10 min at 25° C. with shaking at 1400 rpm. The gel slices were dried in a SpeedVac at 35° C. for 10 min. For trypsin digestion, the gel slices were pre-incubated with 7 ml of 15 ng/ml trypsin (Promega #V5280) at room temperature for 10 min. Afterwards, 25 µl of 50 mM ammonium bicarbonate was added, and the gel slices were incubated at 37° C. for 16 h. The peptide-containing supernatants were dried at 56° C. by SpeedVac for 30 min, then resuspended in 20 µl of solution containing 0.05% formic acid and 3% acetonitrile for mass spectrometry experiments. The resulting peptides were analyzed with a nano-HPLC (Agilent Technologies 1200) directly coupled to an ion-trap mass spectrometer (Bruker 6300 series) equipped with a nano-electrospray source. The separation gradient was 7 min from 5% to 90% acetonitrile. The fragmentation voltage was 1.3 V. The ion trap acquired successive sets of 4 scan modes consisting of: full scan MS over the ranges of 200-2000 m/z, followed by 3 data-dependent MS/MS scans on the 3 most abundant ions in the full scan. The analysis of the spectra was performed with the DataAnalysis for the 6300 Series Ion Trap LC/MS Version 3.4 software package and the proteins were identified with Spectrum Mill Software package (Agilent).

The sequences obtained were screened against the SWISS-PROT database using a MASCOT search engine. The searches were carried out with a peptide mass accuracy tolerance of 100 ppm for external calibration.

Total RNA Extraction and Quantitative RT-PCR Analysis

Total RNA was extracted using the Illustra Triple Prep Kit (GE Healthcare Life Sciences). The cDNA was synthesized from 500 ng of total RNA using the RevertAid H Minus First Strand cDNA Synthesis Kit (Fermentas) for RT-PCR analysis according to the manufacturer's instructions. The qPCR was performed on a real-time PCR detection system Step One Plus (Applied Biosystems), using the KiCqStart SYBR Green qPCR Ready Mix (Sigma-Aldrich). The sequences of the oligonucleotides used in this study are listed in FIG. 15.

Protein Isolation and Western Blot

The sample pellets were diluted in 150-300 µl of 1× PBS with a Protease inhibitor cocktail (Sigma-Aldrich) and sonicated. A NuPAGE® LDS Sample Buffef (Life Technologies) and 5 mM DTT were added and the samples were subjected to the 30 min incubation at 50° C. Alternatively, total proteins were extracted using the Illustra Triple Prep Kit (GE Healthcare Life Sciences). The Western blot was carried out according to a standard procedure using pre-cast gel cassettes (Life Technologies). Inventors used anti-ZNF555 (Ab4) (Sigma-Aldrich), anti-Actin (Sigma-Aldrich) and anti-Lamin A/C (Abcam) antibodies in 1/1000 dilution and anti-rabbit secondary antibodies (Sigma-Aldrich) in 1/1000 dilution. The SeeBlue Plus2 Protein Standard (Life Technologies) was used to detect the size of analysed protein. The detection solutions were the SuperSignal West Pico Chemiluminescent Substrate (Pierce Thermo Scientific) or Chemicon (Millipore).

ZNF555 Knockdown

Cultured human TE671 cells, myoblasts from FSHD patients (Myo_F3) and normal individuals (Myo_N3) were transfected with an esiRNA-targeting ZNF555 (Sigma-Aldrich) as described previously (41) using a Lipofectamine RNAiMAX transfection reagent (Invitrogen, Life Technologies). Briefly, before 24 h of transfection, the cells were trypsinized, collected, diluted with fresh medium and seeded in 6-well plates. Initial transfections for identifying effective esiRNAs were carried out in 24-well cell culture plates. Each sample was assayed in triplicate 72 h post-transfection. A non-specific esiRNA-targeting firefly luciferase was included as a negative control (Sigma-Aldrich). The cotransfection experiments were performed with the luciferase reporter pGL3 plasmids and esiRNA-targeting ZNF555 using a DNA (µg) to Lipofectamine™ 2000 (µl) transfection reagent (Invitrogen, Life Technologies) ratio of 1:2, followed by luciferase assay 72 h post-transfection. The esiRNA were used at a final concentration of 50 nM in all experiments.

ChIP Assay

A ChIP assay was performed in primary myoblasts (Myo_N3 and Myo_F3) using anti-ZNF555 (Sigma-Aldrich), antibodies against acetylated H3K9 histone (Abcam) and mouse IgG (Sigma-Aldrich). 1 µg of each antibody was used per each precipitation well. We used an Imprint Chromatin Immunoprecipitation Kit (Sigma-Aldrich) and followed the manufacture's instruction. The GAPDH (Sigma-Aldrich) and BSR, 4qAe-f (5'-TCCCCTGTAGGCAGAGA-3') and 4qAe-r (5'-CACTGATAACCCAGGTGA-3') primers were used in these experiments. The sequences of all oligonucleotides used in this study are listed in FIG. 15.

Results 1

The β-Satellite Repeat (BSR) from 4qA Allele Possess an Enhancer Activity

The 4qA sequence is represented by 6.2 kb of β-satellite repeat region (BSR) that is not present in the 4qB allele (FIG. 1). An individual BSR is a 67-69 bp repeat that includes a Sau3AI restriction site and exhibits a nucleotide polymorphism (42) that could influence the activation capability of each repeat (FIG. 10). All our constructs were based on the pGL3 vector containing the SV40 promoter (pPro). The construct p4qA (18) contains approximately 20 BSR (total 1474 bp, FIG. 2, pink bars) from the 4qA allele. First, inventors divided the 4qA fragment to three 4qA fragments, Fr 1, Fr 2 and Fr 3, and subcloned each of them in the pPro vector upstream from the SV40 promoter (FIG. 2, FIG. 14). The corresponding constructs, p4qA_1, p4qA_2 and p4qA_3, respectively (FIG. 2), were transiently transfected into rhabdomyosarcoma cells. Inventors found that each fragment increased to the same extent the reporter gene activity relative to the pPro control. Thus, they hypothesized that the presence of any BSR could induce the activation of transcription.

In order to verify the minimal size of activation unit necessary for the activation of reporter gene expression, they have designed several constructs derived from these vectors, shortening again the size of the fragments and inserting. They generated constructs containing the fragments Fr 4, 5, 6 and 7 of different size of BSR sequence, from 63 bp to 203 bp (FIG. 14, FIG. 2, p4qA_4-7). The maximum activation (36×) of luciferase expression was achieved with the p4qA_4 construct that contained an insertion fragment of 67 bp. It was at least twice as high comparing to the constructions with other sizes of the 4qA repeat fragments. Interestingly, the 63 bp fragment (less than one BSR) maintained the enhancer activity that was 14 times higher than a control vector (pPro).

These results show that the highest enhancer activity corresponds to one BSR from 4qA region. The fragment Fr4 of 67 bp, which inventors named 4qAe has been used in their further experiments.

The 4qAe Enhancer Regulates the Gene Expression of 4q35 Locus Ex Vivo

As inventors postulated previously from their 3C data, the 4qA region may be involved in the regulation of the transcriptional activity of the FRG1 and ANT1 genes (18). To confirm the hypothesis, they proceeded to investigate if the enhancer from 4qA (4qAe) would be able to activate the promoters of the ANT1 and FRG1 genes.

To this end, they designed several constructs on the basis of pBasic vector backbone placing 4qAe together with the promoters of the ANT1 or FRG1 genes (715 and 577 bp, respectively; FIG. 14) and compared them with the constructs missing the enhancer. As shown in FIG. 3, the transient transfection of the vector containing the 4qAe enhancer and the ANT1 promoter (p4qAe_ANT1) caused, on average, fivefold augmentation of reporter gene expression as compared with the corresponding enhancerless vectors (pANT1). The result of this experiment shows that the 4qAe sequence may contribute to the ANT1 gene activation, if it is put in a physical proximity to its promoter.

Intriguingly, they did not observe the same effect for 4qAe on the FRG1 promoter (p4qAe_FRG1) (FIG. 3, FIG. 14). There was no significant difference as compared with the vector containing the FRG1 promoter without an enhancer (pFRG1).

The formation of 4qA-Enhancer Specific Protein Complex

In order to better understand the mechanism of the transcriptional activation of the genes situated in the 4q35 region associated with FSHD, inventors decided to test if there are nuclear proteins specifically binding to the 4qAe sequence. The DIG-EMSA essay with nuclear extracts from rabdomiosarcoma (TE671) revealed several slowly migrating complexes. One complex (BS1) appeared to be specific for the 4qA-enhancer fragment (Lane 3, FIG. 4A). Its formation was 80% inhibited by the excess copies of the unlabeled 4qAe fragment, a cold competitor (Lane 4, FIG. 4A). This loss of the DIG-labeled 4qA fragment from specific protein complex was compensated by its equivalent enrichment in the free-oligo fraction FO (Lane 4, FIG. 4A).

Next, they used different BSR sequences in competition assays to understand whether the intrinsic differences in BSR could influence the binding capacity of the 4qA-enhancer. The inclusion of the excess of heterologous competitors corresponding to Fr 6 and Fr 7 (FIG. 14) that were used in previous experiments with luciferase assay partially diminished (about 35% in comparison with the experiment without competitors) the amount of DIG-4qAe-protein complex formation in the band shift 1 (Lane 5 and 6, FIG. 4A). These results indicate the presence of 4qAe-specific protein(s) that do not interact with other BSR sequences.

ZNF555 Protein Specifically Binds to the 4qA-Enhancer

In the next part of their work, inventors decided to identify the protein candidates that could be involved in the 4qAe-binding and thus in the 4qA allele function.

For this purpose, they combined the DIG-EMSA and mass-spectrometry approaches, which would allow them to 'fish out' such proteins (FIG. 4B). Two sets of probes were run in parallel in the gel shift experiment. In both cases, the 4qAe oligo (Fr 4), cold or DIG-labeled, and an unspecific competitor poly(dI-dC) were used. In order to render the location of the EMSA bands detectable by chemiluminescence, the samples were spiked with a small amount of the DIG-labeled 4qAe probe in the first set of probes (Exp 1, Ctl 1). The control "cold" EMSA (Ctl 1) was performed with the addition of excess 4qAe in order to detect the specific displaced band. The revealed DIG-EMSA film was superposed with the Coomassie stained gel of second set of probes. The band corresponding to the shift with 4qAe oligo (Exp 1) was excised from the second set of probes performed in triplicate and analyzed by NanoLC-ESI-MS/MS. The second set of experiments (Exp 2) was performed using "cold" 4qA. Importantly, in parallel, the nuclear extracts of control samples (Ctl 2) were run without an addition of the DNA probe, and the control band of the size of the specific band was also excised and analyzed. Thus, the protein composition between the experiment (Exp 2) and the control (Ctl 2) was compared.

Inventors identified several proteins presented in the experiment (FIG. 16) and control (FIG. 17) bands. Among these proteins some of them were identified in both bands, whereas others were found only in the experiment band, and thus, were presumably associated with the DNA probe. From the set of proteins, a Zinc finger protein 555 (ZNF555-Q8NEP9) was the most prominent candidate corresponding to search criteria. An MRM analysis confirmed the absence of ZNF555 in the control bands (FIG. 11A), whereas the non-specific control protein HSP71 (P11142) was present in both samples (FIG. 11B).

Thus, by the combination of DIG-EMSA and mass-spectrometry approach inventors identified a zinc finger protein ZNF555, which specifically binds to the 4qAe sequence.

mRNA and Protein Expression of ZNF555 in Myoblasts

Inventors analyzed the transcriptional profile of the ZNF555 gene during myogenesis by RT-PCR. All experiments were performed on 4 samples from induced pluripotent (iPS) cells derived from human primary myoblasts, 4 samples from mesenchymal stem cells (MSC) differentiated from the iPS cells and 4 samples from myoblast primary cell lines (37).

They observed an augmentation (200 and 240%) of ZNF555 mRNA expression level in muscle-committed unipotent cells (myoblasts), as compared with pluripotent (iPS cells) and multipotent precursors (MSC), respectively (FIG. 5, A). They did not find any difference in the expression of ZNF555 in FSHD myoblast cells as compared with the cells from healthy individuals (data not shown).

Furthermore, they analyzed the transcriptional level of ZNF555 in non-myogenic cells, fibroblasts and HeLa. The level of ZNF555 mRNA in HeLa cells was statistically lower as compared with all cells of myogenic lineage. The ZNF555 expression in fibroblasts showed no statistically significant difference from that in HeLa cells.

Inventors investigated the ZNF555 protein expression level in order to confirm the data of transcriptome analysis. The ZNF555 protein has not yet been characterized; the antibodies against ZNF555 have been validated only in few cell types including HeLa cells. The purpose of this experiment was to analyze the level of ZNF555 in myoblast cells from normal and FSHD patients (FIG. 5, B). Consistent with the ZNF555 mRNA expression data, inventors did not find any difference in the ZNF555 expression between the cells obtained from healthy and affected individuals on the stage of myoblasts.

Further, they compared the ZNF555 protein level between tumor rhabdomyosarcoma and HeLa cells. They observed high ZNF555 protein expression in the tumor cells of myogenic origin as compared with HeLa cells, which are of epithelial origin. Surprisingly, unlike myoblasts, which did not undergo immortalization, the immortalized myoblasts cells showed a trace level of the ZNF555 protein expression.

Thus, the data of transcriptional and protein level analysis were consistent with each other. This part of the results reveals a myogenic specificity of ZNF555 expression.

ZNF555 is a Transcriptional Regulator of 4qAe

ZNF555 is an uncharacterized protein with a predicted function of transcriptional regulator according to its structure, which has not been previously experimentally validated. Therefore, inventors performed the ZNF555 knockdown in order to (i) experimentally determine the size of protein and (ii) provide the mechanistic insights into the ZNF555 contribution to functional region, related to the FSHD disease. RMS cells were transfected with enzymatically prepared siRNA, as described previously (41) and analyzed for the gene and protein expression. An esiRNA-targeting firefly luciferase was used as a negative control. As shown in FIG. 6A, inventors observed that the esiRNA against ZNF555 efficiently knocked down the ZNF555 transcription. Next, they performed a Western blot analysis and confirmed the knockdown effect on the level of protein expression. They observed a strong band reduction, which corresponds to the size of 60 kDa, approximately (FIG. 6B). In this experiment, they used a polyclonal antibody against ZNF555 provided by Sigma-Aldrich.

Next, they addressed whether the siRNA-mediated depletion of ZNF555 affected the expression of constructs with 4qAe enhancer in RMS cells. They used the same set of constructs as in previous experiments of lusiferase assay. The results from experiments with and without ZNF555 knockdown were compared. They found a significant reduction of luciferase gene expression in the constructs containing the 4qAe enhancer: p4qAe_SV40, p4qAe_FRG1 and p4qAe_ANT1 (FIG. 6C). They did not observe the changes of luciferase expression in the corresponding enhancerless constructs containing the promoters of SV40, FRG1 and ANT1 genes (pSV40, pFRG1 and pANT1). These results are consistent with the EMSA-MS analysis regarding the specific interaction of ZNF555 with 4qAe. Together, these data established ZNF555 as a transcriptional regulator of 4qAe enhancer, which plays an important role in the transcriptional control of the activity of ANT1 and FRG1 genes through 4qAe.

ZNF555 Knockdown Changes the Transcription Level of ANT1 and FRG1

Inventors next determined whether the suppression of ZNF555 expression could influence the activity of gene candidates ANT1 and FRG1. They performed the ZNF555 knockdown in FSHD and control primary myoblasts and RMS cells and analyzed the transcriptional level of ANT1 and FRG1 (FIG. 6A, FIG. 7A). They found that the ZNF555 depletion inhibited the mRNA level of the ANT1 gene in both control and disease cases (FIG. 7B). Importantly, the ANT1 gene was more sensitive to ZNF555 knockdown in FSHD myoblasts: the inhibition of ANT1 was considerably stronger in FSHD myoblasts in comparison with luciferase control ($p<0.05$) and normal myoblasts ($p<0.05$), while the changes of ANT1 expression were not statistically significant. Additionally, they observed a drastic reduction of FRG1 activity ($p<0.01$) in both FSHD and normal myoblasts. While the effect of ZNF555 knockdown impacted the FRG1 and ANT1 genes, in RMS cells the expression level of these genes stayed practically unmodified, as can be seen from FIG. 7B. Therefore, these results provide the first evidence of a functional role of ZNF555 in 4q35 locus via implication in the transcriptional gene regulation.

ZNF555 Association with 4qA BCR in FSHD and Normal Individuals

Inventors' finding of the ZNF555 interaction with the 4qA beta-satellite repeat region relied on in vitro binding during EMSA assay, and thus needed to be confirmed by experiments in living cells. The most suitable approach to analyze the ZNF555 interaction with BSR from the 4qA allele in living cells is to perform a Chromatin Immunoprecipitation assay, which provides a rapid and reliable method to investigate protein-DNA interactions in vivo in order to functionally validate the results obtained from the EMSA-MS analysis.

Accordingly, they performed the ZNF555-specific ChIP assay in human myoblasts from control and FSHD patients. Using sets of specific primers, they analyzed a relative presence of different relevant parts of the 4q35 region in the ZN555 precipitates in FSHD myoblasts and control myoblasts (FIG. 15).

First of all, they analyzed the ZNF555 precipitation in BSR region containing the 4qAe enhancer in FSHD and control myoblasts. As can be seen from FIG. 8, A-B the enrichment of ZNF555 was remarkably high in both samples. Further, they were interested in examining the transcriptionally functional regions corresponding to the known gene-candidates from 4q35 locus. Intriguingly, they found that ZNF555 binds the ANT1 promoter in both normal and FSHD individuals, but with different level of association (FIG. 8). Regarding the FRG1 gene, they did not detect significant association of ZNF555 with the FRG1 promoter region in myoblasts neither from FSHD patients nor from healthy individuals. This is consistent with the observation that the FRG1 promoter was not activated by the 4qAe presence in their reporter assay data. They did not find the ZNF555 binding to the FRG2 promoter neither in normal nor in FSHD myoblasts.

Next, inventors analyzed the association of ZNF555 to D4Z4 repeats. Intriguingly, they observed a strong interaction of ZNF555 with DUX4-containing canonical D4Z4 repeats, the reduction of which is associated with the disease. Then, they tested a short version of D4Z4 that contains a homologous DUX4c gene, located in the truncated and inversed D4Z4 unit. They did not find the presence of ZNF555 in DUX4c in both normal and diseased myoblasts.

In addition to the ZNF555 binding to the relevant regions of the 4q35 locus, they were also interested in the association of these regions with active state of chromatin. For this purpose, they analyzed the enrichment in H3K9 acetylated (H3K9Ac) histone, a mark of transcriptionally active chromatin. They observed that the presence of ZNF555 in the 4q35 region was constantly associated with this modified histone (FIG. 8).

Together, these results demonstrate the association of ZNF555 with the FSHD region. Moreover, they confirmed the interaction of the 4qAe enhancer from the 4qA BSR region and the ZNF555 protein in myoblasts from FSHD patients and normal individuals.

Discussion

Facioscapulohumeral Dystrophy (FSHD) is an epi/genetic satellite DNA related disease associated with at least two satellite repeats in 4q35: (1) macrosatellite (D4Z4) and (2) β-satellite (4qA allele) repeats. The slow progress in FSHD research could be explained by the lack of a functional model. The straightforward analysis using in vivo animal model, which would replicate the symptoms of the FSHD disease in humans, cannot be used since the D4Z4 homologous sequences were identified only in higher primates. Moreover, linked D4Z4-BSR clusters from the FSHD region are found only in chimpanzees, and even this primate never suffers from FSHD (43).

Exacerbating the difficulties in the FSHD studies, recent publications emphasize the complexity of the FSHD disease (27,30,44-46), pointing out that no gene candidate proposed so far is sufficient to explain the FSHD development. Most of the current FSHD studies have been focused on the DUX4 transcript inside D4Z4 and its contraction (7,47). However, the inappropriate expression of the DUX4 stable transcript that takes place in FSHD pathogenesis was observed in FSHD fibroblasts (27), which are not affected in FSHD, as well as in muscles and myogenic cells of some unaffected individuals without D4Z4 deletion (46). These somewhat controversial observations suggest that the role of DUX4 expression in FSHD and its potential role as a therapeutic target require a more thorough exploration. An additional complexity has been demonstrated by a recent study that identified healthy individuals (2.1% of healthy population) carrying the contracted D4Z4 with 4qA-PAS sequence (30). Accordingly, the role of the genetic regions other than 4q35 cannot be ruled out, as has been shown for the phenotypic form of FSHD (24,25).

However, concerning the role of 4q35, the contribution of the BSR region has not been explored so far. It is known that the reduction of macrosatellite tandem is associated with the presence of BSR downstream of macrosatellite in the patients with canonical FSHD, or FSHD1. Nevertheless, without the BSR-containing 4qA allele the D4Z4-contraction alone is not pathological. Importantly, the presence of BSR is associated with phenotypic FSHD, or FSHD2, which is not related to the D4Z4 contraction (22). These observations strongly suggest the significance of the BSR presence in FSHD development. Therefore, in the present study inventors focused on the second satellite related to FSHD and studied (i) its functional role, (ii) its molecular targets and (iii) the mechanism of its transcriptional control in the FSHD-related 4q35 region.

Beta-Satellite Repeat is a Transcriptional Regulator

The beta-satellite DNA is presented by tandem arrays of divergent Sau3A 67-69 pb monomer repeat units (53% G+C) (42,48). Beta satellite repeats (BSR) show a predominant heterochromatic distribution, which includes the short arm of acrocentric chromosomes and the pericentromeric part of chromosomes 1, 3 and 9 [38, 39]. In these regions, the beta satellite arrays are adjacent to LSau 3.3 kb macrosatellites (D4Z4-like repeats). The D4Z4 macrosatellite repeats and BSR are also located in the subtelomeric region of chromosomes 4 and 10 [40, 41]. Recently, the presence of BSR next to a newly created telomere has been shown to retard its replication timing [42]. Intriguingly, inventors' experiments demonstrate the presence of a sequence capable of the transcriptional activation inside an individual BSR from the 4qA allele, suggesting that each BSR could have this property. Among those repeats, they identified one, 4qAe, which exhibited particularly strong activation property.

Additionally, the reporter assays show that if 4qAe is put in a physical proximity to the promoter of the ANT1 gene (gene located 5 Mbp distal to the 4qA region in the genome), it could strongly activate this promoter. Importantly, ANT1 is the only muscle-specific gene out of several known FSHD gene candidates. It has been reported that ANT1 is overexpressed in FSHD cells (9,10). ANT1 is implicated in the muscle function protecting the cells from apoptosis (31,32). Additionally, the ANT1 protein is involved in red-ox system stability (33) and related to a hypersensitivity to oxidative stress of FSHD muscles (34).

It appears from this evidence that the role of BSR in the transcriptional control of the 4q35 locus might be other than heterochromatinization. Taking into account the GC-reach structure of BSR, their methylation state remains to be identified.

BSR Polymorphism Leads to the Polymorphism of Transcriptional Activity

The comparison between 12 BSR sequences reveals a highly conserved Sau3A-containing part and a low homology part (FIG. 10). The presence of the conserved part might explain why all analysed BSR fragments could similarly act as transcriptional enhancers in their experiments. One might expect, however, that the sequence differences between individual BSR could influence the degree of enhancer activity, either by changing the affinity to transcriptional activators or else by binding of transcriptional repressors. In addition, the fact that, as compared to the individual repeats, the whole 4qA has a lower transcription activation potential, could be explained by the tendency of repeats to form heterochromatin, inhibitory for transcription (49).

Inventors' further experiments (EMSA data) provided additional evidence that an individual BSR has specific protein partners. At the same time, they do not rule out the possibility of common transcriptional factors shared by all repeats. Therefore, they suggest that a variety of transcription factors could be involved in transcriptional regulation by the 4qA allele. Further work is needed to clarify the role of sequence variability in the 4qA allele function, for example, by identifying the proteins that bind to different BSR sequences.

Overall, the present results provide the first experimental evidence that BRS from 4qA allele act as transcription regulatory elements with different degree of enhancer activity, which could be a starting point for the future study concerning the BSR polymorphism in FSHD patients and healthy individuals. A cloning of additional 4qA alleles from FSHD patients and their analysis could be envisaged.

ZNF555 is a Trans-Acting Element for BSR

To understand the mechanism of transcriptional activation by 4qAe and the role of BSR in the FSHD genesis, inventors searched for the proteins binding to 4qAe (the strongest BSR enhancer that they found) using a combination of two technologies: DIG-EMSA and Mass-Spectrometry. This approach was developed by their team and allowed them to identify ZNF555, a protein that specifically interacts with BSR (4qAe). The knockdown of this protein leads to a significant reduction of 4qAe enhancer activity for the ANT1 promoter in the reporter assay. Moreover, they observed a similar reduction effect with other promoters (SV40 and FRG1) when 4qAe was present. Given that the SV40 enhancer is not sensitive to the ZNF555 knockdown effect the data indicate that ZNF555 specifically interacts with 4qAe enhancer. The ChIP data verify that ZNF555 is associated with the 4qAe region.

ZNF555 is an uncharacterised protein. The analysis of the ZNF555 expression profile provides evidence for its strong presence in myoblasts as compared with the cells of non-muscular origin, fibroblasts and HeLa cells. Moreover, they demonstrate that its expression is related to the muscle committed cells as compared with their pluripotent and multipotent precursors. Thus, they hypothesize that ZNF555 could play a role in myogenesis. Supporting this suggestion, the Disease Atlas application of NextBio library (Nextbio.com) to the transcriptome Meta-Analysis (36) reveals significant transcriptional changes in the ZNF555 level in musculoskeletal diseases such as muscular cachexia, musculoskeletal fibromatosis and myopathies (Nextbio.com) (FIG. 12). Additionally, they analysed the sequence homology of human ZNF555 protein with other species and determined the highest score for chimpanzee (628 AA), rhesus macaque (628 AA), horse (624 AA) and cattle (624 AA). According to the database of known and predicted protein-protein Interactions (http://string-db.org/), a predicted functional partner available for the ZNF555 protein is ADAM12 (FIG. 13). Interestingly, this cell surface protein is involved in muscle development, namely in skeletal muscle regeneration and myotube formation, muscle stability and survival (50,51).

With respect to the potential molecular functions of ZNF555, this protein contains DNA-binding domains and thus could have a wide variety of functions, most of which encompassing some form of transcriptional activation or repression. It could be a transcriptional activator due to the presence of 15 "zinc fingers" of the Cys2-His2 type and a transcriptional repressor due to the presence of KRAB (Krüppel associated box) domain, which is known to be an effective repressor of transcription and shown to interact with KAP1 (KRAB-associated protein 1, TRIM28) recruiting histone modifying proteins and inducing long-range repression through the propagation of heterochromatin-associated modifications (52). In inventors' study, the ZNF555 presence in the 4q35 locus was associated with active chromatin marker and behaved rather as a transcriptional activator in luciferase assay. How these regulatory functions are exerted remains to be explored.

Intriguingly, inventors did not observe a difference in the ZNF555 expression between FSHD and normal individuals, thus they hypothesized that the permissive chromatin structure could play a role in the interaction of ZNF555 in the 4q35 region. Their data provide an additional information concerning the histone modifications of 4q35 locus associated with repressed and active chromatin that have been demonstrated elsewhere (53-55) and are consistent with their data. The first studies of post-translational modifications of histones showed that the D4Z4 macrosatellite, DUX4c and FRG2 have the features of 'unexpressed euchromatin' (54,55). D4Z4 chromatin contains both euchromatic and heterochromatic histone modifications (56) in normal cells and FSHD myoblasts (53,55). The FRG1 promoter in both normal and FSHD myoblasts was characterized by H3K27 trimethylation and Polycomb repressor complex binding (53), consistent with their data, showing that this promoter is depleted in H3K9Ac. Furthermore, the BSR region is remarkably enriched in H3K9Ac in FSHD myoblasts in comparison with the control. This is in line with the model of epigenetic activation in the 4q35 locus in FSHD (19,23,57).

The 4q35.2 region presents high homology with chromosome 10, and the 4qA allele is also present in 10q region (26,58). However, taking together the proteomic and transcriptomic data, as well as the absence of potential myogenic genes in 10q26 and the low level of pairing between homologous regions of 4q and 10q in interphase nuclei (18,59), inventors' data strongly implicate ZNF555 in the function of the 4q35 locus. It remains to be explored, however, whether BSR and ZNF555 interaction could have broader implications, not restricted to 4q35.

Distant Regulation in 4q35 Locus

Inventors' data reveal the first evidence of 4qA-BSR implication in the transcriptional regulation of 4q35 locus and precisely, in ANT1 gene transcriptional activity. On the one hand, the 4qA BSR can interact with ZNF555 transcription factor, which impacts the activity of the ANT1 promoter in FSHD myoblasts. On the other hand, ZNF555 influences the promoter activity of the ANT1 gene via the 4qAe enhancer. Inventors' results are in general agreement with the study of abnormal chromatin conformation changes in FSHD myoblasts (19,21,60) leading to the direct interactions between the 4qA region and the long distance genes in 4q35 (18). They are also consistent with the current most popular DNA-looping model of enhancer action, based on the formation of topologically closed looped chromatin domains leading to the direct enhancer-promoter interactions, otherwise distantly located from each other (61-63).

According to their data the ZNF555 depletion is involved in the FRG1 transcriptional control, but probably neither directly since it was not found (trace level) in the FRG1 promoter by ChIP, nor via BSR since the FRG1 promoter was not sensitive to the presence of 4qAe. Further study is needed to understand the 4q35 network and ZNF555 function in it.

Accordingly, they propose a working model (FIG. 9) of the functional role of the 4qA allele in transcriptional control of the ANT1 gene in FSHD patients, where the cooperative BSR binding with the ZNF555 transcriptional factor could be a critical step in the formation of a transcriptionally productive complex.

Originally considered "junk" DNA, satellite DNA has more recently been reconsidered as having various functions, implicating it in different "satellite diseases", including neurological, developmental disorders and cancers (56). Satellite repeats could be overrepresented in transcription regulatory modules, and may have an impact on replication, epigenetic regulation and genomic instability (64-67). A role of BSR in pathology has been demonstrated (68,69). Therefore, the manipulation of the BSR activity is expected by inventors be beneficial in the treatment of FSHD.

Results 2:

Effects of ZNF KO on Apoptosis

Inventors observed an additional ZNF555 property (FIG. 18). The cells in the experiments with ZNF555 knockdown that was performed using $siRNA_{ZNF555}$ (KO+) were compared with the cells transfected with siRNA targeting luciferase (Ctl−) and with the cells transfected with the plasmids (FIG. 14) (KO−). All experiments were performed under the same conditions (see Materials and Methods section). The cells were washed three times in PBS in order to eliminate the dead cells. The total protein quantity corresponding to the living cells was measured 72h post transfection. Intriguingly, a strong increase of the total protein from survived cells (about 40% and 30% in comparison with KO− and Ctl−, correspondingly) was observed after the ZNF555 knockdown. This effect was confirmed by cell counting (data not shown).

Therefore, these results provide the first evidence of ZNF555 possible implication in cell apoptosis or/and cell proliferation.

Results 3:

ZNF555 Induces the ANT1 Up-Regulation in FSHD Myoblasts

The ANT1 expression level in the cells of ZNF555-induced overexpression was examined and compared with that of parental non-transduced counterparts cultured under the same conditions. As can be seen in FIG. 19, in the FSHD myoblasts the level of ANT1 expression was dramatically impacted (20-fold increase) by ZNF555. This is consistent with inventors experiments of ZNF555-knockdown when the level of ANT1 was significantly reduced due to the ZNF555 depletion. Therefore, these results reinforce the inventors' demonstration of the ZNF555 role as an upstream regulator of ANT1 expression.

Example 2

Inventors designed lentiviral vector constructs (pLKO.1-blast) using the pLKO.1-puro (Sigma) containing shRNA against ZNF555.

Sequences of shRNA used in this study are identified below:

```
shRNA-1:
                                  (SEQ ID NO: 44)
CCTTCAGTTATTCTTCGGCTT shRNA-2:
                                  (SEQ ID NO: 45)
CCTGAAGACAAATCCTATGAA shRNA-3:
                                  (SEQ ID NO: 46)
CCATCATCTTTACCAATACAT
```

They observed the morphological, proliferative and cell survival changes of RMS cells (rhabdomyosarcoma cells) and FSHD cells due to the inhibition of ZNF555.

REFERENCES

1. Theadom, A., Rodrigues, M., Roxburgh, R., Balalla, S., Higgins, C., Bhattacharjee, R., Jones, K., Krishnamurthi, R. and Feigin, V. (2014) Prevalence of muscular dystrophies: a systematic literature review. *Neuroepidemiology*, 43, 259-268.
2. Padberg, G. W., Lunt, P. W., Koch, M. and Fardeau, M. (1991) Diagnostic criteria for facioscapulohumeral muscular dystrophy. *Neuromuscul Disord*, 1, 231-234.
3. Tawil, R., Figlewicz, D. A., Griggs, R. C. and Weiffenbach, B. (1998) Facioscapulohumeral dystrophy: a distinct regional myopathy with a novel molecular pathogenesis. FSH Consortium. *Ann Neurol*, 43, 279-282.
4. Lemmers, R. J., O'Shea, S., Padberg, G. W., Lunt, P. W. and van der Maarel, S. M. (2012) Best practice guidelines on genetic diagnostics of Facioscapulohumeral muscular dystrophy: workshop 9th June 2010, LUMC, Leiden, The Netherlands. *Neuromuscul Disord*, 22, 463-470.
5. Tassin, A., Laoudj-Chenivesse, D., Vanderplanck, C., Barro, M., Charron, S., Ansseau, E., Chen, Y. W., Mercier, J., Coppee, F. and Belayew, A. (2013) DUX4 expression in FSHD muscle cells: how could such a rare protein cause a myopathy? *J Cell Mol Med*, 17, 76-89.
6. Lemmers, R. J., van der Vliet, P. J., Klooster, R., Sacconi, S., Camano, P., Dauwerse, J. G., Snider, L., Straasheijm, K. R., van Ommen, G. J., Padberg, G. W. et al. (2010) A unifying genetic model for facioscapulohumeral muscular dystrophy. *Science*, 329, 1650-1653.
7. Stadler, G., Rahimov, F., King, O. D., Chen, J. C., Robin, J. D., Wagner, K. R., Shay, J. W., Emerson, C. P., Jr. and Wright, W. E. (2013) Telomere position effect regulates DUX4 in human facioscapulohumeral muscular dystrophy. *Nat Struct Mol Biol*.
8. van der Maarel, S. M., Tawil, R. and Tapscott, S. J. (2011) Facioscapulohumeral muscular dystrophy and DUX4: breaking the silence. *Trends Mol Med*, 17, 252-258.
9. Gabellini, D., Green, M. R. and Tupler, R. (2002) Inappropriate gene activation in FSHD: a repressor complex binds a chromosomal repeat deleted in dystrophic muscle. *Cell*, 110, 339-348.
10. Laoudj-Chenivesse, D., Carnac, G., Bisbal, C., Hugon, G., Bouillot, S., Desnuelle, C., Vassetzky, Y. and Fernandez, A. (2005) Increased levels of adenine nucleotide translocator 1 protein and response to oxidative stress are early events in facioscapulohumeral muscular dystrophy muscle. *J Mol Med*, 83, 216-224.
11. Rijkers, T., Deidda, G., van Koningsbruggen, S., van Geel, M., Lemmers, R. J., van Deutekom, J. C., Figlewicz, D., Hewitt, J. E., Padberg, G. W., Frants, R. R. et al. (2004) FRG2, an FSHD candidate gene, is transcriptionally upregulated in differentiating primary myoblast cultures of FSHD patients. *J Med Genet*, 41, 826-836.
12. Bosnakovski, D., Lamb, S., Simsek, T., Xu, Z., Belayew, A., Perlingeiro, R. and Kyba, M. (2008) DUX4c, an FSHD candidate gene, interferes with myogenic regulators and abolishes myoblast differentiation. *Exp Neurol*, 214, 87-96.
13. Ansseau, E., Laoudj-Chenivesse, D., Marcowycz, A., Tassin, A., Vanderplanck, C., Sauvage, S., Barro, M., Mahieu, I., Leroy, A., Leclercq, I. et al. (2009) DUX4c is up-regulated in FSHD. It induces the MYF5 protein and human myoblast proliferation. *PLoS One*, 4, e7482.
14. Liu, Q., Jones, T. I., Tang, V. W., Brieher, W. M. and Jones, P. L. (2010) Facioscapulohumeral muscular dystrophy region gene-1 (FRG-1) is an actin-bundling protein associated with muscle-attachment sites. *J Cell Sci*, 123, 1116-1123.
15. Gabellini, D., D'Antona, G., Moggio, M., Prelle, A., Zecca, C., Adami, R., Angeletti, B., Ciscato, P., Pellegrino, M. A., Bottinelli, R. et al. (2006) Facioscapulohumeral muscular dystrophy in mice overexpressing FRG1. *Nature*, 439, 973-977.
16. Caruso, N., Herberth, B., Bartoli, M., Puppo, F., Dumonceaux, J., Zimmermann, A., Denadai, S., Lebosse, M., Roche, S., Geng, L. et al. (2013) Deregulation of the protocadherin gene FAT1 alters muscle shapes: implications for the pathogenesis of facioscapulohumeral dystrophy. *PLoS Genet*, 9, e1003550.
17. Puppo, F., Dionnet, E., Gaillard, M. C., Gaildrat, P., Castro, C., Vovan, C., Karine, B., Bernard, R., Attarian, S., Goto, K. et al. (2015) Identification of variants in the 4q35 gene FAT1 in patients with a Facioscapulohumeral dystrophy (FSHD)-like phenotype. *Hum Mutat*.
18. Pirozhkova, I., Petrov, A., Dmitriev, P., Laoudj, D., Lipinski, M. and Vassetzky, Y. (2008) A functional role for 4qA/B in the structural rearrangement of the 4q35 region and in the regulation of FRG1 and ANT1 in facioscapulohumeral dystrophy. *PLoS One*, 3, e3389.
19. Petrov, A., Pirozhkova, I., Carnac, G., Laoudj, D., Lipinski, M. and Vassetzky, Y. S. (2006) Chromatin loop domain organization within the 4q35 locus in facioscapulohumeral dystrophy patients versus normal human myoblasts. *Proc Natl Acad Sci USA*, 103, 6982-6987.
20. Krom, Y. D., Thijssen, P. E., Young, J. M., den Hamer, B., Balog, J., Yao, Z., Maves, L., Snider, L., Knopp, P., Zammit, P. S. et al. (2013) Intrinsic epigenetic regulation of the D4Z4 macrosatellite repeat in a transgenic mouse model for FSHD. *PLoS Genet*, 9, e1003415.
21. Xu, X., Tsumagari, K., Sowden, J., Tawil, R., Boyle, A. P., Song, L., Furey, T. S., Crawford, G. E. and Ehrlich, M. (2009) DNaseI hypersensitivity at gene-poor, FSH dystrophy-linked 4q35.2. *Nucleic Acids Res*, 37, 7381-7393.
22. de Greef, J. C., Lemmers, R. J., Camano, P., Day, J. W., Sacconi, S., Dunand, M., van Engelen, B. G., Kiuru-Enari, S., Padberg, G. W., Rosa, A. L. et al. (2010) Clinical features of facioscapulohumeral muscular dystrophy 2. *Neurology*, 75, 1548-1554.
23. van Overveld, P. G., Lemmers, R. J., Sandkuijl, L. A., Enthoven, L., Winokur, S. T., Bakels, F., Padberg, G. W., van Ommen, G. J., Frants, R. R. and van der Maarel, S. M. (2003) Hypomethylation of D4Z4 in 4q-linked and non-4q-linked facioscapulohumeral muscular dystrophy. *Nat Genet*, 35, 315-317.
24. Larsen, M., Rost, S., El Hajj, N., Ferbert, A., Deschauer, M., Walter, M. C., Schoser, B., Tacik, P., Kress, W. and Muller, C. R. (2014) Diagnostic approach for FSHD revisited: SMCHD1 mutations cause FSHD2 and act as modifiers of disease severity in FSHD1. *Eur J Hum Genet*.
25. Lemmers, R. J., Tawil, R., Petek, L. M., Balog, J., Block, G. J., Santen, G. W., Amell, A. M., van der Vliet, P. J., Almomani, R., Straasheijm, K. R. et al. (2012) Digenic inheritance of an SMCHD1 mutation and an FSHD-permissive D4Z4 allele causes facioscapulohumeral muscular dystrophy type 2. *Nat Genet*, 44, 1370-1374.

26. Lemmers, R. J., de Kievit, P., Sandkuijl, L., Padberg, G. W., van Ommen, G. J., Frants, R. R. and van der Maarel, S. M. (2002) Facioscapulohumeral muscular dystrophy is uniquely associated with one of the two variants of the 4q subtelomere. *Nat Genet,* 32, 235-236.

27. Snider, L., Geng, L. N., Lemmers, R. J., Kyba, M., Ware, C. B., Nelson, A. M., Tawil, R., Filippova, G. N., van der Maarel, S. M., Tapscott, S. J. et al. (2010) Facioscapulohumeral dystrophy: incomplete suppression of a retrotransposed gene. *PLoS Genet,* 6, e1001181.

28. Dixit, M., Ansseau, E., Tassin, A., Winokur, S., Shi, R., Qian, H., Sauvage, S., Matteotti, C., van Acker, A. M., Leo, O. et al. (2007) DUX4, a candidate gene of facioscapulohumeral muscular dystrophy, encodes a transcriptional activator of PITX1. *Proc Natl Acad Sci USA,* 104, 18157-18162.

29. van Geel, M., Dickson, M. C., Beck, A. F., Bolland, D. J., Frants, R. R., van der Maarel, S. M., de Jong, P. J. and Hewitt, J. E. (2002) Genomic analysis of human chromosome 10q and 4q telomeres suggests a common origin. *Genomics,* 79, 210-217.

30. Scionti, I., Greco, F., Ricci, G., Govi, M., Arashiro, P., Vercelli, L., Berardinelli, A., Angelini, C., Antonini, G., Cao, M. et al. (2012) Large-scale population analysis challenges the current criteria for the molecular diagnosis of fascioscapulohumeral muscular dystrophy. *Am J Hum Genet,* 90, 628-635.

31. Lynn, E. G., Stevens, M. V., Wong, R. P., Carabenciov, D., Jacobson, J., Murphy, E. and Sack, M. N. (2010) Transient upregulation of PGC-1alpha diminishes cardiac ischemia tolerance via upregulation of ANT1. *J Mol Cell Cardiol,* 49, 693-698.

32. Heger, J., Abdallah, Y., Shahzad, T., Klumpe, I., Piper, H. M., Schultheiss, H. P., Schluter, K. D., Schulz, R., Euler, G. and Dorner, A. (2012) Transgenic overexpression of the adenine nucleotide translocase 1 protects cardiomyocytes against TGFbeta1-induced apoptosis by stabilization of the mitochondrial permeability transition pore. *J Mol Cell Cardiol,* 53, 73-81.

33. Lena, A., Rechichi, M., Salvetti, A., Vecchio, D., Evangelista, M., Rainaldi, G., Gremigni, V. and Rossi, L. (2010) The silencing of adenine nucleotide translocase isoform 1 induces oxidative stress and programmed cell death in ADF human glioblastoma cells. *FEBS J,* 277, 2853-2867.

34. Barro, M., Carnac, G., Flavier, S., Mercier, J., Vassetzky, Y. and Laoudj-Chenivesse, D. (2010) Myoblasts from affected and non-affected FSHD muscles exhibit morphological differentiation defects. *J Cell Mol Med,* 14, 275-289.

35. Petrov, A., Allinne, J., Pirozhkova, I., Laoudj, D., Lipinski, M. and Vassetzky, Y. S. (2008) A nuclear matrix attachment site in the 4q35 locus has an enhancer-blocking activity in vivo: implications for the facio-scapulo-humeral dystrophy. *Genome Res,* 18, 39-45.

36. Kupershmidt, I., Su, Q. J., Grewal, A., Sundaresh, S., Halperin, I., Flynn, J., Shekar, M., Wang, H., Park, J., Cui, W. et al. (2010) Ontology-based meta-analysis of global collections of high-throughput public data. *PLoS One,* 5.

37. Pirozhkova, I., Barat, A., Dmitriev, P., Kim, E., Robert, T., Guegan, J., Bilhou-Nabera, C., Busato, F., Tost, J., Carnac, G. et al. (2013) Differences in transcription patterns between induced pluripotent stem cells produced from the same germ layer are erased upon differentiation. *PLoS One,* 8, e53033.

38. Mamchaoui, K., Trollet, C., Bigot, A., Negroni, E., Chaouch, S., Wolff, A., Kandalla, P. K., Marie, S., Di Santo, J., St Guily, J. L. et al. (2011) Immortalized pathological human myoblasts: towards a universal tool for the study of neuromuscular disorders. *Skelet Muscle,* 1, 34.

39. Klochkov, D., Rincon-Arano, H., Ioudinkova, E. S., Valadez-Graham, V., Gavrilov, A., Recillas-Targa, F. and Razin, S. V. (2006) A CTCF-dependent silencer located in the differentially methylated area may regulate expression of a housekeeping gene overlapping a tissue-specific gene domain. *Mol Cell Biol,* 26, 1589-1597.

40. Shevchenko, A., Wilm, M., Vorm, O. and Mann, M. (1996) Mass spectrometric sequencing of proteins silver-stained polyacrylamide gels. *Anal Chem,* 68, 850-858.

41. Kolas, N. K., Chapman, J. R., Nakada, S., Ylanko, J., Chahwan, R., Sweeney, F. D., Panier, S., Mendez, M., Wildenhain, J., Thomson, T. M. et al. (2007) Orchestration of the DNA-damage response by the RNF8 ubiquitin ligase. *Science,* 318, 1637-1640.

42. Meneveri, R., Agresti, A., Della Valle, G., Talarico, D., Siccardi, A. G. and Ginelli, E. (1985) Identification of a human clustered G+C-rich DNA family of repeats (Sau3A family). *J Mol Biol,* 186, 483-489.

43. Kramer, H., Han, C., Post, W., Goff, D., Diez-Roux, A., Cooper, R., Jinagouda, S. and Shea, S. (2004) Racial/ethnic differences in hypertension and hypertension treatment and control in the multi-ethnic study of atherosclerosis (MESA). *Am J Hypertens,* 17, 963-970.

44. Ricci, G., Zatz, M. and Tupler, R. (2014) Facioscapulohumeral muscular dystrophy: more complex than it appears. *Curr Mol Med.*

45. Ricci, G., Scionti, I., Sera, F., Govi, M., D'Amico, R., Frambolli, I., Mele, F., Filosto, M., Vercelli, L., Ruggiero, L. et al. (2013) Large scale genotype-phenotype analyses indicate that novel prognostic tools are required for families with facioscapulohumeral muscular dystrophy. *Brain,* 136, 3408-3417.

46. Jones, T. I., Chen, J. C., Rahimov, F., Homma, S., Arashiro, P., Beermann, M. L., King, O. D., Miller, J. B., Kunkel, L. M., Emerson, C. P., Jr. et al. (2012) Facioscapulohumeral muscular dystrophy family studies of DUX4 expression: evidence for disease modifiers and a quantitative model of pathogenesis. *Hum Mol Genet,* 21, 4419-4430.

47. Kowaljow, V., Marcowycz, A., Ansseau, E., Conde, C. B., Sauvage, S., Matteotti, C., Arias, C., Corona, E. D., Nunez, N. G., Leo, O. et al. (2007) The DUX4 gene at the FSHD1A locus encodes a pro-apoptotic protein. *Neuromuscul Disord,* 17, 611-623.

48. Waye, J. S. and Willard, H. F. (1989) Human beta satellite DNA: genomic organization and sequence definition of a class of highly repetitive tandem DNA. *Proc Natl Acad Sci USA,* 86, 6250-6254.

49. Khobta, A., Anderhub, S., Kitsera, N. and Epe, B. (2010) Gene silencing induced by oxidative DNA base damage: association with local decrease of histone H4 acetylation in the promoter region. *Nucleic Acids Res,* 38, 4285-4295.

50. Galliano, M. F., Huet, C., Frygelius, J., Polgren, A., Wewer, U. M. and Engvall, E. (2000) Binding of ADAM12, a marker of skeletal muscle regeneration, to the muscle-specific actin-binding protein, alpha-actinin-2, is required for myoblast fusion. *J Biol Chem,* 275, 13933-13939.
51. Kronqvist, P., Kawaguchi, N., Albrechtsen, R., Xu, X., Schroder, H. D., Moghadaszadeh, B., Nielsen, F. C., Frohlich, C., Engvall, E. and Wewer, U. M. (2002) ADAM12 alleviates the skeletal muscle pathology in mdx dystrophic mice. *Am J Pathol,* 161, 1535-1540.
52. Groner, A.C., Meylan, S., Ciuffi, A., Zangger, N., Ambrosini, G., Dénervaud, N., Bucher, P. and Trono, D. (2010) KRAB-Zinc Finger Proteins and KAP1 Can Mediate Long-Range Transcriptional Repression through Heterochromatin Spreading. *PLoS Genet,* 6, e1000869.
53. Bodega, B., Ramirez, G. D., Grasser, F., Cheli, S., Brunelli, S., Mora, M., Meneveri, R., Marozzi, A., Mueller, S., Battaglioli, E. et al. (2009) Remodeling of the chromatin structure of the facioscapulohumeral muscular dystrophy (FSHD) locus and upregulation of FSHD-related gene 1 (FRG1) expression during human myogenic differentiation. *BMC Biol,* 7, 41.
54. Jiang, G., Yang, F., van Overveld, P. G., Vedanarayanan, V., van der Maarel, S. and Ehrlich, M. (2003) Testing the position-effect variegation hypothesis for facioscapulohumeral muscular dystrophy by analysis of histone modification and gene expression in subtelomeric 4q. *Hum Mol Genet,* 12, 2909-2921.
55. Yang, F., Shao, C., Vedanarayanan, V. and Ehrlich, M. (2004) Cytogenetic and immuno-FISH analysis of the 4q subtelomeric region, which is associated with facioscapulohumeral muscular dystrophy. *Chromosoma,* 112, 350-359.
56. Zeng, W., de Greef, J. C., Chen, Y. Y., Chien, R., Kong, X., Gregson, H. C., Winokur, S. T., Pyle, A., Robertson, K. D., Schmiesing, J. A. et al. (2009) Specific loss of histone H3 lysine 9 trimethylation and HP1gamma/cohesin binding at D4Z4 repeats is associated with facioscapulohumeral dystrophy (FSHD). *PLoS Genet,* 5, e1000559.
57. Cabianca, D. S., Casa, V., Bodega, B., Xynos, A., Ginelli, E., Tanaka, Y. and Gabellini, D. (2012) A long ncRNA links copy number variation to a polycomb/trithorax epigenetic switch in FSHD muscular dystrophy. *Cell,* 149, 819-831.
58. Giussani, M., Cardone, M. F., Bodega, B., Ginelli, E. and Meneveri, R. (2012) Evolutionary history of linked D4Z4 and Beta satellite clusters at the FSHD locus (4q35). *Genomics,* 100, 289-296.
59. Stout, K., van der Maarel, S., Frants, R. R., Padberg, G. W., Ropers, H. H. and Haaf, T. (1999) Somatic pairing between subtelomeric chromosome regions: implications for human genetic disease? *Chromosome Res,* 7, 323-329.
60. Tsumagari, K., Qi, L., Jackson, K., Shao, C., Lacey, M., Sowden, J., Tawil, R., Vedanarayanan, V. and Ehrlich, M. (2008) Epigenetics of a tandem DNA repeat: chromatin DNaseI sensitivity and opposite methylation changes in cancers. *Nucleic Acids Res,* 36, 2196-2207.
61. Kulaeva, O. I., Nizovtseva, E. V., Polikanov, Y. S., Ulianov, S. V. and Studitsky, V. M. (2012) Distant activation of transcription: mechanisms of enhancer action. *Mol Cell Biol,* 32, 4892-4897.
62. Schatt, M. D., Rusconi, S. and Schaffner, W. (1990) A single DNA-binding transcription factor is sufficient for activation from a distant enhancer and/or from a promoter position. *EMBO J,* 9, 481-487.
63. Petrascheck, M., Escher, D., Mahmoudi, T., Verrijzer, C. P., Schaffner, W. and Barberis, A. (2005) DNA looping induced by a transcriptional enhancer in vivo. *Nucleic Acids Res,* 33, 3743-3750.
64. Erliandri, I., Fu, H., Nakano, M., Kim, J. H., Miga, K. H., Liskovykh, M., Earnshaw, W. C., Masumoto, H., Kouprina, N., Aladjem, M. I. et al. (2015) Replication of alpha-satellite DNA arrays in endogenous human centromeric regions and in human artificial chromosome. *Nucleic Acids Res,* 42, 11502-11516.
65. Jurka, J., Kapitonov, V. V., Kohany, O. and Jurka, M. V. (2007) Repetitive sequences in complex genomes: structure and evolution. *Annu Rev Genomics Hum Genet,* 8, 241-259.
66. Zhu, Q., Pao, G. M., Huynh, A. M., Suh, H., Tonnu, N., Nederlof, P. M., Gage, F. H. and Verma, I. M. (2011) BRCA1 tumour suppression occurs via heterochromatin-mediated silencing. *Nature,* 477, 179-184.
67. Li, Y., Miyanari, Y., Shirane, K., Nitta, H., Kubota, T., Ohashi, H., Okamoto, A. and Sasaki, H. (2013) Sequence-specific microscopic visualization of DNA methylation status at satellite repeats in individual cell nuclei and chromosomes. *Nucleic Acids Res,* 41, e186.
68. Ting, D. T., Lipson, D., Paul, S., Brannigan, B. W., Akhavanfard, S., Coffman, E. J., Contino, G., Deshpande, V., Iafrate, A. J., Letovsky, S. et al. (2011) Aberrant overexpression of satellite repeats in pancreatic and other epithelial cancers. *Science,* 331, 593-596.
69. Scott, H. S., Kudoh, J., Wattenhofer, M., Shibuya, K., Berry, A., Chrast, R., Guipponi, M., Wang, J., Kawasaki, K., Asakawa, S. et al. (2001) Insertion of beta-satellite repeats identifies a transmembrane protease causing both congenital and childhood onset autosomal recessive deafness. *Nat Genet,* 27, 59-63.

The invention claimed is:

1. A method for treating rhabdomyosarcoma in a subject comprising a step of transfecting said rhabdomyosarcoma with an inhibitory nucleic acid comprising SEQ ID NO: 46 to a subject in need of treatment.

2. A composition comprising a pharmaceutically acceptable carrier or excipient and an inhibitory nucleic acid comprising SEQ ID NO: 46.

* * * * *

UNITED STATES PATENT AND TRADEMARK OFFICE
CERTIFICATE OF CORRECTION

PATENT NO. : 10,954,515 B2
APPLICATION NO. : 15/568009
DATED : March 23, 2021
INVENTOR(S) : Iryna Pirozhkova and Vasily Ogryzko It is certified that error appears in the above-identified patent and that said Letters Patent is hereby corrected as shown below:

In the Specification

Column 9,
Line 58, "confoniiation" should read --conformation--.

Column 22,
Line 53, "of 50 nm" should read --of 50nM--.

Signed and Sealed this
Twelfth Day of July, 2022

Katherine Kelly Vidal
*Director of the United States Patent and Trademark Office*